United States Patent [19]
Werp et al.

[11] Patent Number: 6,015,414
[45] Date of Patent: Jan. 18, 2000

[54] METHOD AND APPARATUS FOR MAGNETICALLY CONTROLLING MOTION DIRECTION OF A MECHANICALLY PUSHED CATHETER

[75] Inventors: Peter R. Werp, Los Gatos, Calif.; Walter M. Blume, Webster Groves; Francis M. Creighton, IV, St. Louis, both of Mo.; Rogers C. Ritter, Charlottesville, Va.

[73] Assignee: Stereotaxis, Inc., St. Louis, Mo.

[21] Appl. No.: 08/920,446

[22] Filed: Aug. 29, 1997

[51] Int. Cl.$^7$ ................................................. A61F 11/00
[52] U.S. Cl. ........................................... 606/108; 606/130
[58] Field of Search ............................. 600/12; 604/276, 604/95; 606/108, 130

[56] References Cited

U.S. PATENT DOCUMENTS

| | | | |
|---|---|---|---|
| 3,358,676 | 12/1967 | Frei et al. ................................. | 128/1.3 |
| 3,674,014 | 7/1972 | Tillander ............................ | 128/2.05 R |
| 3,941,119 | 3/1976 | Corrales ................................ | 128/2 M |
| 4,244,362 | 1/1981 | Anderson . | |
| 4,445,501 | 5/1984 | Bresler . | |
| 4,869,247 | 9/1989 | Howard, III et al. ................ | 128/303.1 |
| 5,125,888 | 6/1992 | Howard et al. ........................... | 600/12 |
| 5,332,987 | 7/1994 | Hennessy et al. ...................... | 335/216 |
| 5,334,207 | 8/1994 | Gay, Jr. ....................................... | 606/7 |
| 5,353,807 | 10/1994 | DeMarco ................................. | 128/772 |
| 5,415,617 | 5/1995 | Kraus . | |
| 5,425,382 | 6/1995 | Golden et al. . | |
| 5,558,091 | 9/1996 | Acker et al. .......................... | 128/653.1 |
| 5,622,169 | 4/1997 | Golden et al. . | |
| 5,624,430 | 4/1997 | Eton et al. . | |
| 5,654,864 | 8/1997 | Ritter et al. ............................. | 361/141 |

FOREIGN PATENT DOCUMENTS

| | | | |
|---|---|---|---|
| WO 96/037955 | 2/1996 | WIPO ............................ | H02N 15/00 |

OTHER PUBLICATIONS

"Characteristics of an Improved Magnetic–Implant Guidance System," Robert G. McNeil et al., IEEE Trans. Biomed. Eng., vol. 42, No. 8, Aug. 1995, pp. 802–808.

"Functional Design Features and Initial Performance Characteristics of a Magnetic–Implant Guidance System for Stereotactic Neurosurgery," Robert G. McNeil et al., IEEE Trans. Biomed. Eng., vol. 42, No. 8, Aug. 1995, pp. 793–801.

"Magnetic Manipulation Instrumentation for Medical Physics Research," G. T. Gillies et al, Rev.Sci.Instrum., (65)3:533–562 (1994).

"Goniometric Motion Controller for the Superconducting Coil in a Magnetic Stereotaxis System," Elizabeth G. Quate et al., IEEE Trans. Biomed. Eng., vol. 38, No. 9, Sep. 1991, pp. 899–905.

"Nonlinear magnetic stereotaxis: Three–dimensional, in vivo remote magnetic manipulation of a small object in canine brain," M.S. Grady et al., Med. Phys. 17(3), May/Jun. 1990, pp. 405–415.

(List continued on next page.)

*Primary Examiner*—Michael Buiz
*Assistant Examiner*—Julian W. Woo
*Attorney, Agent, or Firm*—Howell & Haferkamp, LC

[57] ABSTRACT

The movement of a catheter through a medium, which may be living tissue such as a human brain, is controlled by mechanically pushing a flexible catheter having a magnetic tip through the medium and applying a magnetic field having a magnitude and a direction that guides the mechanically-pushed catheter tip stepwise along a desired path. The magnetic field is controlled in a Magnetic Stereotaxis System by a processor using an adaptation of a PID (proportional, integral, and derivative) feedback method. The magnetic fields are applied by superconducting coils, and the currents applied through the coils are selected to minimize a current metric.

37 Claims, 3 Drawing Sheets

OTHER PUBLICATIONS

"A New Magnet System for 'Intravascular Navigation', " Shyam B. Yodh, et al., Med and Biol. Engrg. (6):143–147 (1968).

"Symposium on BioEngineering: Magnetic Forces for Medical Applications," D. Bruce Montgomery and R. J. Weggel, Journal of Applied Physics 40:1039–1041, (1969).

"Superconducting Magnet System for Intravascular Navigation," D. B. Montgomery et al, Journal of Applied Physics 40:2129–2132 (1969).

"Laboratory Experience with a Magnetically Guided Intravascular Catheter System," Herbert L. Cares, M.D., et al, J. Neurosurg. (38):145–154 (1973).

"Electromagnetic Bougienage to Lengthen Esophageal Segments in Congenital Esophageal Atresia," W. Hardy Hendren and J. Richard Hale, New England Journal of Medicine, (293):428–432, (1975).

"The Design of a 2T Superconducting Solenoid for Magnetic Catheter Guidance," J.R. Hale, et al. IEEE Transactions on Magnetics, (MAG–11)2:563–564 (1975).

"Medical Applications of Magnet Devices," J.R. Hale, IEEE Transactions on Magnetics, (Mag–11) 5:1405–1407 (1974).

"Magnetic Probe for the Stereotactic Thrombosis of Intracranial Aneurysms," John Alksne et al, J. Neurol. Psychiat., (30):159–162 (1967).

"Magnetically Controlled Intravascular Catheter," John Alksne, Surgery, (61)1:339–345 (1968).

"Current Status of Metallic Thrombosis of Intracranial Aneurysms," J.F. Alkense and R.W. Rand, Progr. Neurol. Surg., (3):212–229 (1969).

"Stereotactic Thrombosis of Intracranial Aneurysms," New England Jour. Medicine, (284)4: 171–174 (1971).

"Progress in the Magnetically Controlled Stereotactic Thrombosis of Intracranial Aneurysms," J.F. Alksne, Confin. Neurol, (34):368–373 (1972).

"Ferromagnetic Embolization," Jane Barry et al, Radiology, (138):341–349 (1981).

"The Pod, a New Magnetic Device for Medical Applications," E.H. Frei et al, in Proceedings of 16th Ann. Conference on Engineering in Medicine and Biology, (5):156–157 (1963).

"Development of the "Pod" and Experiments on Dogs," E.H. Frei et al., in Proceedings of 17th Ann. Conference on Engineering in Medicine and Biology, (6):89 (1964).

"A Magnetic Device for Use in Exploration of the Cardiovascular System," Henry Neufeld et al, Israel J. Med. Sci. 921–924 (1965).

"The Pod and its Applications," E.H. Frei et al, in Proceedings of Ann. Conference on Engineering in Medicine and Biology, (8):65 (1966).

"The Pod and its Applications," E.H. Frei et al, Med. Res. Eng., (5)4:11–18 (1966).

"POD Catheter: A Means for Small Vessel Exploration," S.K. Hilal et al, Jour. Applied Physics, (40):1046–1048 (1969).

"Development and Use of the POD Catheter in the Cerebral Vascular System," J. Driller et al, Med. Res.Engrg, (8):11–16 (1969).

"The Magnetically Guided Bronchial Catheter of Modified POD Design," William Casarella et al, Radiology, (93):930–932 (1969).

"Selective Cerebral Catheterization," Johnathan Molcho et al, IEEE Transactions on Bio–Medical Engineering, (BME–17)2:134–140 (1970).

"The POD Bronchial Catheter," Jack Driler et al, IEEE Transactions on Magnetics, (Mag–6) 2:353–355 (1970).

"Selective Angiography with a Catheter Guided by a Magnet," H. Tillander, IEEE Transactions on Magnetics, (Mag–6)2:355–358 (1970).

"Kinetics of Magnetically Guided Catheters," Jack Driller, IEEE Transactions on Magnetics, (Mag–6)2:467–471 (1970).

"The POD Bronchial Catheter and Associated Biopsy Wire," J. Driller et al, Med & Biol Engrg., (8):15–18 (1970).

"Cerebral Arteriovenous Malformations Treated with Magnetically Guided Emboli," Jack Driller et al, in Proc. of 25th Ann Conf on Engineering and Biology, (14):306 (1972).

"Intravascular Intracranial EEG Recording," Richard Penn et al, J. Neurosurg., (38):239–243 (1973).

"Magnetic Materials as Biological Implants—Criteria for Selection," Jack Driller and Victor Parsonnet, IEEE Trans. on Magnetics, (Mag–9)3:444–447 (1973).

"Design Aids for Simple Magnet Systems Useful in Biomedical Applications," Jack Driller and Bruce Sollish, IEEE Trans. on Biomedical Engineering, (BME–20)6:459–464 (1973).

"Magnetically Guided Devices for Vascular Exploration and Treatment," Sadek K. Hilal et al, Radiology, (113):529–540 (1974).

"A Rotating D.C. Superconducting Magnet System for Guidance of Intravascular Catheters," S.R. Savitz et al, in Proc. of 28th Ann Conf on Engineering and Biology, (17):422 (1975).

"Magnetics for Power and Control of Body Implants," George D. Summers, in Proc of Fifth National Biomedical Sciences Instrumentation Symposium, (4):293–302 (1967).

"A Flying Superconducting Magnet and Cryostat for Magnetic Suspension of Wind–Tunnel Models," C. Britcher et al, Cryogenics, 185–189 (1984) (p. 188 not available).

"Off–Axis Helmoltz Field," J. Higbie, Am J. Phys. (46)10:1075–1076 (1978).

"Maximum Current in a Superconducting Wire," E. Yu. Klimenko et al, Sov. Phys. Dokl (30)6:518–520 (1985).

"Magnetic Guidance of a Catheter with Articulated Steel Tip," Hans Tillander, Acta Radiologica, (35):62–64 (1951).

"Duodenal Intubation," John W. Devine, et al. Surgery, (33):513–515 (1953).

"Selective Angiography of the Abdominal Aorta with a Guided Catheter," Hans Tillander, Acta Radiologica, (45):21–26 (1956).

"External Magnetic Guidance of Endovascular Catheters with a Superconducting Magnet: Preliminary Trials," A. Gaston et al, J. Neuroradiol., (15):137–147 (1988).

"A Review Of Medical Applications Of Magnet Attraction And Detection," Driller et al., (11)6:271–277 (1987).

Howard, III et al., "Magnetic Neurosurgery," *Stereotact. Funct. Neurosurg*; 1996, 66, pp. 102–107.

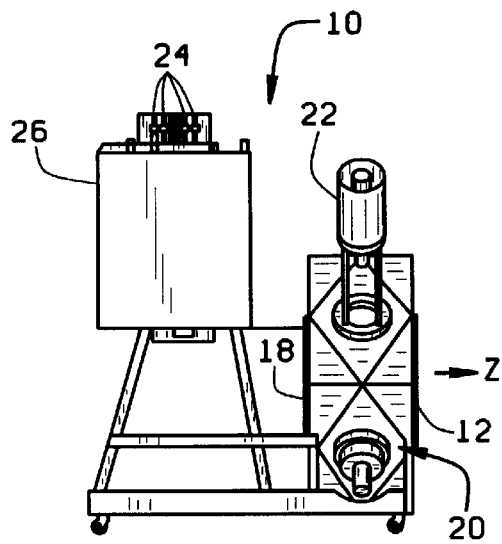
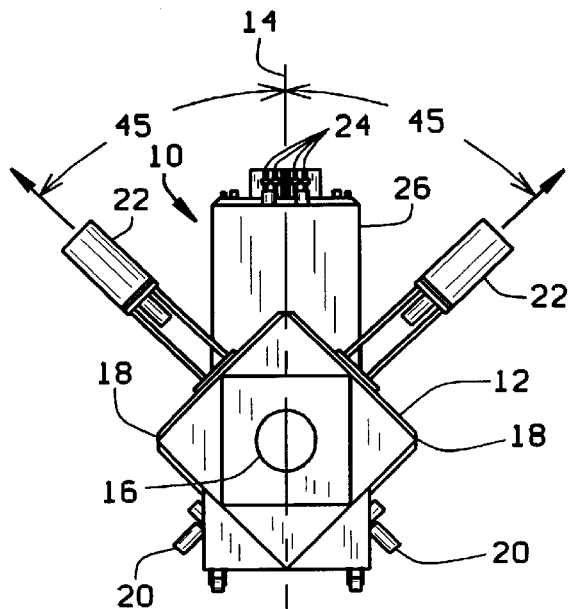
FIG. 1A
FIG. 1B
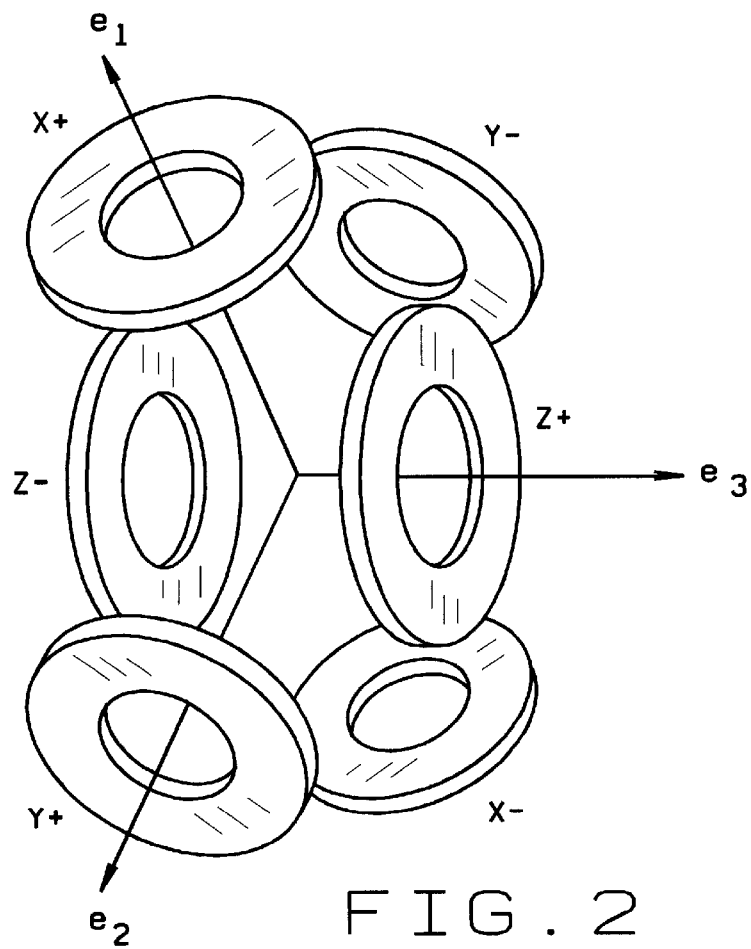
FIG. 2

METHOD AND APPARATUS FOR MAGNETICALLY CONTROLLING MOTION DIRECTION OF A MECHANICALLY PUSHED CATHETER

BACKGROUND OF THE INVENTION

1. Field of the Invention

This invention relates to devices and methods for moving an implant in a body, and more particularly to such devices and methods that apply pushing forces with a flexible attachment and that magnetically steer the implant in the body with high accuracy.

2. Description of Related Art

There is a large body of conventional (nonmagnetic) stereotactic prior art, in which a frame (e.g., a so-called "BRW Frame") is attached to the skull to provide a navigation framework. Such a frame has arcs to determine an angle of an "insertion guide" which is usually a straight tube through which some medical therapeutic agent is passed, such as a biopsy tool. These methods have been confined to straightline approaches to a target.

There is also a smaller body of prior art in which a handheld permanent magnet or an electromagnet is used to move a metallic implant.

Previous implants for delivering medication or therapy to body tissues, and particularly brain tissue, have generally relied upon the navigation of tethered implants within vessels, or navigation of tethered or untethered implants moved intraparenchymally (in general brain tissue) by magnetic force.

Navigation of untethered implants, in the past, has generally comprised finding ways to apply magnetic force optimally, including both magnitude and direction, for a given step of "free" motion. However, difficulty in finding a set of currents to accomplish a move step is encountered because of the complexity of calculating the magnetic forces resulting from multiple coils.

It is well-known that two like coils on a common axis, having like currents, provide a highly uniform magnetic field on their axis at the midpoint between them. In addition, it is known that the field is approximately uniform for an appreciable region around the midpoint, and relatively strong, as compared with any other two-coil arrangement having the same coil currents. This arrangement of coils and currents meets the need for an accurate, strong guiding torque applied to a magnetic implant near the midpoint between the coils. Because the field is quite uniform near the midpoint, undesired magnetic forces on the implant are negligible. However, this arrangement is less suitable for a moving implant when the implant is some distance from the midpoint between the coils or not on the axis, or when the implant axis is not along the coil axis. In these important cases, this simple coil arrangement cannot provide accurate directional guidance. Furthermore, simple vector combinations of three such coil pair arrangements cannot provide accurate guidance in an arbitrary direction, except at one spot at the center of the arrangement.

The Magnetic Stereotaxis System (MSS) originated from the hopes that a less-invasive methodology could be developed which would allow neurosurgeons to operate in previously inaccessible regions of the brain. By introducing a small permanent magnetic implant into the brain through a small "burr hole" drilled through the skull prior to the operation, large superconducting coils could be used in conjunction with a pushing mechanism to magnetically guide the implant and overlaying catheter through the brain's parenchyma, all the while avoiding the important structures of the brain. The operational methodology of the MSS was, and continues to be, expected to be less destructive to the tissues of the brain than the shunts, straight tubes, and other devices associated with conventional techniques in neurosurgery.

The first MSS was conceptually developed in 1984 as the Video Tumor Fighter (VTF), and is shown in U.S. Pat. No. 4,869,247 issued Sep. 26, 1989. This system specifically focused on the eradication of deep-seated brain tumors via hyperthermia-based treatment. It was envisioned that the magnetic coils of the VTF would guide a small (~3 mm diameter) magnetic thermosphere through the brain into a tumor. Rastering the implant throughout the volume of the growth, the tumor cells could be destroyed by inductively heating the implant with radio-frequency radiation.

Further studies revealed that the reality of a magnetomotive based system used to direct a small implant promised numerous applications other than the hyperthermia-based treatment of brain tumors by induction. These included: biopsy, pallidotomy, delivery of precision radiation therapy, magnetically placed implants that deliver chemotherapy to otherwise inaccessible tumor locations, and (by attaching a semi-permeable catheter to the implant) the delivery of chemicals to specific sites in the brain without the need for penetrating the blood-brain barrier which has complicated contemporary systemic chemical delivery. This means of chemical delivery seemed particularly hopeful in the treatment of Parkinson's disease, where the catheter could be used to deliver dopamine to the affected regions of the brain with minimal indiscriminate distribution of the neurotransmitter to the surrounding tissue, thereby lessening attendant side effects. It was in the light of these possible broadened applications of the VTF that the system became known as the MSS.

Referring now to FIG. 1A and FIG. 1B, the most recent MSS apparatus 10 included six superconducting coils (not visible in FIG. 1A and FIG. 1B) located in a rectangular box or helmet 12. With the z-axis defined in the direction of the axial component of the head, the x- and y-coil axes are rotated 45° from the sagittal plane 14 of the head, which would be positioned in opening 16. The x- and y-coil axes are symmetrically located such that the horizontal extensions 22 of the MSS apparatus 10 away from the patient's body is minimized. Because the lower edge of the treatable part of the brain is typically located 10 cm above the shoulder line for an average adult, the z-coils (located on the body-axis of the supine patient) were compressed to allow for a maximum extension of the head into helmet 12.

The vision component of the MSS consists of a superposition of pre-operative MRI images referenced by biplanar fluoroscopy cameras 20 linked to a real-time host system (not shown in FIG. 1A and FIG. 1B). Both cameras 20 are calibrated to the MSS six-coil helmet design. X-ray generators for cameras 20 are located inside magnetic shields 22. Using x-ray visible fiducial markers located on the skull of the conscious patient, the coordination of the implant's position inside the cranial volume to the helmet's reference system (and hence the corresponding preoperative MRI scan) is done through a series of coordinate transformations executed by a host system and displayed for the surgeon on a workstation.

The central problem to the inductively-based guidance of a magnetic implant pertains to the inverse problem of electromagnetism as influenced by Earnshaw's theorem.

The conventional problem of electromagnetism centers on the evaluation of the gradient and magnetic field given established magnetomotive sources. For the MSS, however, the situation is reversed in that the magnetic field and its gradient are specified at a point in space while the strengths of the six actuators are to be determined. Control of the motion and position of an untethered implant would be difficult in the MSS, given the fundamental instability of a non-diamagnetic moment in a static or quasi-static magnetic field as related to Earnshaw's theorem for static/quasi-static magnetic fields, if it were not for the resistive nature of the parenchyma. In early tests, small cylindrical (up to 5 mm in length and 5 mm in diameter) permanently magnetized NdBFe objects were used. The relatively strong moment of these objects (0.016 A-m$^2$ to more than 0.04 A-m$^2$) facilitated the creation of the necessary aligning torque without the requirement of a strong magnetizing field, resulting in lower current values.

The permanent magnetization of the implant requires a predetermined magnetic field in order to ensure that the implant is oriented in the desired direction. While it is possible to generate a magnetic force to displace the implant, it was found that the requirement of specific force and field alignment could result in unobtainable currents (as high as thousands of amperes). It was also found that even for viable solutions, the equilibrium state was sometimes unstable to such an extent that the implant tended to be difficult to control.

SUMMARY OF THE INVENTION

The invention is an apparatus and method for moving an implant in the body by applying pushing forces with a flexible attachment and magnetically steering the implant in the body with high accuracy and controllability. Because the intended moving force is applied non-magnetically, it is possible and desirable to apply currents in the magnetic steering apparatus in such combinations as to maximize the magnetic field at a body location inside the coil array to thereby provide optimal directional guidance torque on an implant while minimizing undesired translational force on the implant.

According to one aspect of the invention, there is provided a method for controlling movement of a catheter through a medium, in which a flexible catheter having a magnetic tip is pushed through a medium, and a magnetic field having a magnitude and orientation effective to guide the mechanically-pushed catheter tip in a predetermined direction is applied.

According to another aspect of the invention, a method for providing stepwise movement of a catheter having a magnetic tip is provided, in which the method includes the steps of selecting a desired path of the catheter through living tissue, inserting the catheter tip into the living tissue, determining actual positions of the magnetic tip and correction vectors (the correction vectors representing differences between locations on the desired path and the actual positions of the magnetic tip), storing values of correction vectors in a memory, and applying a magnetic field adjusted to achieve movement of the magnetic tip at least approximately along the desired path, the adjustment depending upon at least one stored set of values of correction vectors.

Also provided is a device for guiding a catheter having a magnetic tip through a medium, the device comprising a helmet having a cavity configured to encompass a medium through which a catheter is to be guided, a magnetic field generator generating a magnetic field within the cavity, a position sensor sensing a location of a magnetic tip of a catheter in the cavity and generating a signal indicative of the sensed location, an advancement mechanism pushing the magnetic tip of the catheter through the medium, and a processor responsive to the signal from the position sensor and having an operator control input, the processor being configured to control the magnetic field generated by the magnetic field generator in response to commands input via the operator control input and the signal received from the position sensor.

The above embodiments may also incorporate significant additional improvements, including, for example, the minimization of a current metric, so that the proper magnetic field to guide the magnetic tip through the medium is generated with a near-minimum amount of current.

The methods and apparatuses of this invention provide the ability to more accurately direct a seed or catheter in the brain or other parts of the body, including the path to that position. Highly accurate directional guidance of implants is possible over arbitrary nonlinear paths, and the implant can be guided freely through tissues such as brain tissue, without being limited to the interior of vessels.

Additional advantages of the present invention over prior art systems are that:

(1) Solutions applicable to guiding an implant on a predetermined path are simpler, and thus, are found more rapidly and with less likelihood of error for a given step of motion.

(2) Solutions are much more stable than with prior art systems, and are free of runaway conditions.

(3) Currents applied by the new method are generally considerably smaller than with previous methods; therefore, the current changes between steps are smaller, allowing changes to be made much more rapidly and accurately between steps, and with less possibility of quenching superconducting magnets.

(4) Guidance force occurs without skid, which is a condition in which the magnetic field that orients the implant and the magnetic force are in different directions so that the axis of the implant skids along the path.

(5) Currents are applied in a simple temporal fashion, moving directly from one set to another set between two steps of motion. The actual force impulse causing each step of motion is from the duration and distance of the externally applied non-magnetic force during that step. (Prior art systems ramped currents from conditions for subthreshold force to that of a moving force and then back down below threshold at the appropriate time, which is a complex dynamic sequence subject to substantial error in step length due to the tribological nature of the implant and tissue.

(6) Navigation can now occur continuously rather than in steps.

It is thus an object of the invention to provide a method for controlling the motion of a catheter in any predetermined direction.

It is a further object of the invention to control the motion of a catheter by applying a torque to the catheter to guide its direction with a reliable, predictable strength.

It is yet another object of the invention to control the motion of a catheter rapidly, accurately, and reliably, even when the magnetic system used in conjunction with the catheter includes superconducting coils that are vulnerable to misoperation from too rapid current changes.

BRIEF DESCRIPTION OF THE DRAWINGS

FIGS. 1A and 1B are views along the Z-axis and into the cavity of one embodiment of a Magnetic Stereotaxis System (MSS), respectively;

DESCRIPTION OF THE PREFERRED EMBODIMENTS

The invention is described herein in the context of guiding an implant inside a brain because tests have been performed for this case. However, those skilled in the art will recognize that the invention is applicable to other parts of the body and to other media through which a magnetic tip at the end of a flexible catheter can be pushed.

Figure 2:
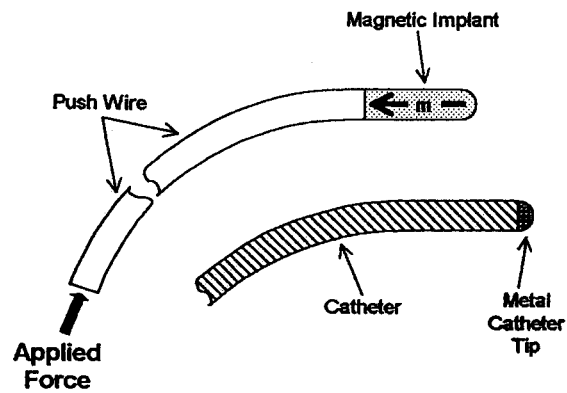
FIG. 2 is a simplified representation showing the orientation of superconducting coils within the helmet of an MSS.

In the present example, a system of six coils is provided. Referring to FIG. 2, which is a simplified representation of the coil geometry, the coils X+, X−, Y+, Y−, Z+, and Z− are operated in unbalanced pairs (X+, X−), (Y+, Y−), (Z+, Z−) acting approximately as three vectors X, Y, and Z having mutually perpendicular directions, but different magnitudes. The operation is achieved in a manner that is effective at positions off the axis of any or all of the three pairs of coils (X+, X−), (Y+, Y−), (Z+, Z−) constituting the helmet (or other coil support arrangement).

Figure 3A:
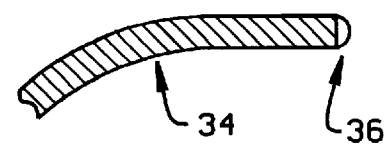
FIG. 3A is drawing of a portion of a catheter having a metal tip.
Figure 3B:
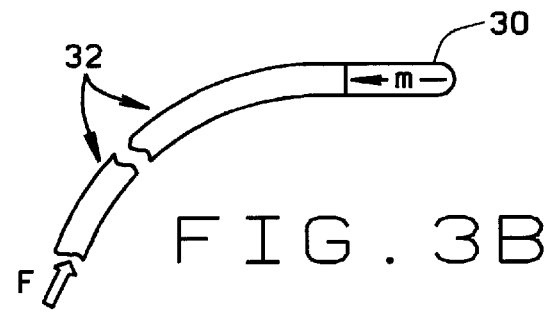
FIG. 3B is a drawing of a magnetic element and push wire within the catheter of FIG. 3A.

The method for controlling the path in the Magnetic Stereotaxis System (MSS) includes calculations involving vectors that represent desired path steps and corrective feedback vectors in an inventive adaptation of a well-known PID (proportional, integral, and derivative) feedback method. However, the operations here are on the motion of a magnetic implant. Referring to FIGS. 3A and 3B, the magnetic implant 30 acts as a leading element (the "directing train engine," which is called a magnetic delivery vehicle or MDV) and which is only part of the overall moving unit which also includes a pushing stylette 32 driven by a motor (not shown) which supplies a force F. Stylette 32 and implant 30 are surrounded by flexible catheter 34, which has a metal tip 36 at the end within which MDV 30 is located. The method and apparatus of this invention controls the curving elements of the catheter.

Figure 4:
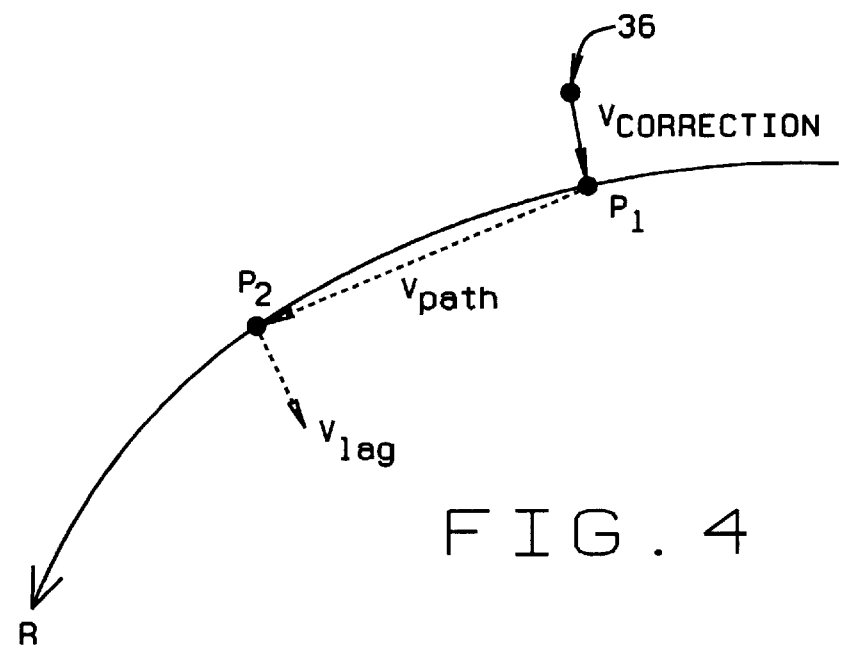
FIG. 4 is a diagram showing various points and vectors along a desired path of a catheter tip, in which the points and vectors shown are significant for the calculation of the magnetic field needed to guide the tip in accordance with the invention.

For the purposes of this discussion of the invention, the term "lag" is applied to the angle by which the catheter would fall outside a curve that would be followed by a completely limp catheter. During magnetic navigation, the MSS system monitors the position of the catheter tip (the MDV) versus a desired position in accordance with a planned path. Referring to FIG. 4, corrections are made in accordance with a feedback/lag model that is given by the equation $$V_{step} = V_{path} + V_{lag} + g \frac{V_{correction}}{|V_{correction}|}, \qquad (1)$$

in which:

$V_{lag}$ is a lag-correction vector pointing to an inside of a local curvature of the planned path indicated by R at point $p_2$; and g is a gain factor; and $V_{path}$ is constructed by finding a point $p_1$ on the planned path closest to the present actual position, and then finding a point $p_2$ further along the planned path which matches the length of the intended step. Then $V_{path} = p_2 - p_1$;

$V_{correction}$ is a vector from the actual position to the point on the path closest to the present actual position (i.e., a direction opposite an "error vector"); and $V_{step}$ is the resultant direction that the next step should take, corrected for lag.

The direction of $V_{step}$ is constrained to vary from move to move in a manner so that sudden changes in $V_{step}$ result in a path having a specified minimum radius of curvature or a less curved trajectory. The value of g is computed and adjusted for each step by means of a PID model in which $$g = ||k_p V_{c(n)} + k_i(V_{c(n)} + V_{c(n-1)} + V_{c(n-2)}) + k_d(V_{c(n)} - V_{c(n-1)})||,$$

where:

$k_p$, $k_i$, and $k_d$ are predetermined constants that may be found by experiment; and $V_{c(n)}$, $V_{c(n-1)}$, and $V_{c(n-2)}$ are the correction vectors at the nth step (present step), the previous (n−1)th step, and the (n−2)th steps, respectively.

It is noted that what here is called a "correction vector" is the negative of what is often called an "error vector." The term "correction vector" rather than "error vector" has been used throughout this description for convenience. However, this usage is not intended to be limiting in any way, because those skilled in the art will recognize the equivalence of "correction vectors" and "error vectors" and the notational changes that would be required by the substitution of one for the other.

When the correction vectors at the nth, (n−1)th, and (n−2)th steps are used in the correction vector $V_{step}$, they become an approximation to an integral mode of control. That is, a correction is made proportional to the integral of the recent path errors. Similarly, an approximate derivative or rate correction is made when the difference $(V_{c(n)} - V_{c(n-1)})$ of the present and most recent correction vectors is used as a term in $V_{step}$.

In one exemplary MSS implementation, vector $V_{lag}$ was determined experimentally by attempting to drive a magnetic catheter tip (such as tip 36 in FIG. 3A) in a circle of predetermined radius, but setting $V_{lag} = 0$. The catheter was driven by a motor providing a constant advancement rate through a phantom gel, which provided some friction. Where there is such friction, an equilibrium arises because the force from the gel counteracts the force from the magnetic field and tends to balance it at some point before alignment of movement with the magnetic field is achieved. In this case, the counterbalancing force of the gel simulated the counterbalancing force of actual brain tissue, and as expected, the magnetic tip spiraled outward from the circle in a direction a few degrees out of alignment with the magnetic field. $V_{lag}$ was then experimentally set to be the vector correction that would have been necessary to provide to counteract the deviation from the circular path.

By increasing the magnitude of the field, the magnitude of $V_{lag}$ can be reduced. However, it is also desirable to at least approximately minimize the coil currents required to generate the magnetic field. Experiments have shown that, for the particular set of coils in one MSS apparatus, with a motor pushing a catheter along the magnetic field at a rate of about 0.5 mm/s, there was little decrease in $V_{lag}$ for fields greater than about 0.3 Tesla. Therefore, in the experiment to determine $V_{lag}$, as well as in other tests, the magnetic field was constrained to have a magnitude no greater than 0.3 Tesla. This value has been found, by experiment, to be sufficient to orient the direction of movement of a magnetic tip of a catheter being pushed by a motor at 0.5 mm/s through a phantom gel. It will be understood that the necessary magnetic field magnitude may vary if different catheters, motors, or magnetic tips are used, or if a different advancement rate is applied.

Correction according to $V_{lag}$ is a single-parameter means of anticipating error that would occur due to restoring torques from an attached pushing element. A person skilled in the art would recognize the close relationship of this action to the concept of "feed-forward" in the field of control theory. It is intended, according to one aspect of the invention, that the inventive apparatuses and techniques may be useful for applications in which a simple feed-forward correction is not adequate. In such applications, a computer or processor will have a representation of a planned or predetermined path stored in its memory. At any location or locations where the planned path deviates from a straight line in front of a then-present location of the seed, a program stored in the computer provides an added correction vector, which may be a function of several different parameters, to provide a better correction than $V_{lag}$ by anticipating future error in the absence of such correction. As one example, if a planned path curves in more than one plane, a correction vector can contain terms which have correction vector components in each of the planes. The weighting of these components preferably varies as the inverses of the individual radii of curvature, and are also preferably weighted inversely according to the distance from the present seed position at which the particular curvatures occur. These parameters can be readily calculated by a program stored in the memory of the computer. It is thus possible, and may be preferable, to use information related to a future location of the seed to guide the seed, and/or a determined rate of change in the observed correction vectors in addition to information stored in memory about its past position and errors.

With respect to the gain parameters $k_p$, $k_i$, and $k_d$, it has been experimentally determined that, for the tested MSS apparatus, it is sufficient to set $k_p=0.5$, $k_i=0.5$, and $k_d=0$. The parameter $k_d$, which effectively adjusts the speed of response of the system, can be set to zero because the system response obtained has been satisfactory for the relatively slow tip advancement rate of 0.5 mm/s. In addition, setting $k_d=0$ has the advantage of reducing noise in the system, because the imaging method used to locate the magnetic tip (biplanar x-ray imaging) has provided an accuracy only within about ±1.0 mm. Adjusting the system gain by increasing the magnitude of $k_d$ would result in significant noise amplification without a concomitant increase in position sensing accuracy. If more accurate methods of determining the location of the seed were used, it would be practical to use a nonzero value of $k_d$ to provide more rapid system response. This more rapid system response could permit an increase of the tip advancement rate above 0.5 mm/s in appropriate medical procedures, which may shorten the time necessary to perform such procedures.

Once the vector $V_{step}$ is determined, representing a vector corresponding to a motion of the magnetic tip at least approximately in the direction of the desired path, the coil currents necessary to generate the required field must be determined. In general, this problem is underdetermined in that many different sets of coil currents could be used to generate the required field, and, without the addition of further constraints, solutions can be obtained that require impractical amounts of currents in some or all of the coils. A method of determining practical values of coil currents that generate a sufficient magnitude magnetic field in the correct direction at the location of the magnetic tip has been found, and is described herein.

For controlling superconducting or normally conducting coils, the root-mean-square value of the coil currents (the coil-current metric) is minimized while the strength and direction of the magnetic field remain at the desired values. (The magnetic field is linear with respect to the coil currents.) This constraint removes three of the six degrees of freedom in selecting the six coil currents, leaving a quadratic equation for the current metric. This metric is minimized to compute the optimal coil currents. While minimizing the current metric does not necessarily correspond to minimizing the individual current magnitudes, it is a useful and efficient way of ensuring that the current magnitudes are kept at a sufficiently low level for purposes of the invention.

The m equality, linearly constrained quadratic problem is stated as $$\left.\begin{aligned}\text{Maximize}\quad & z = \sum_{i=1}^{n} x_i c_i + \sum_{i,j=1}^{n} \dot{x}_i P_{ij} x_j \\ \text{Subject to}\quad & \sum_{j=1}^{n} D_{ij} x_j = e_j \quad (i=1,\ldots,m)\end{aligned}\right\} \text{or} \quad (2)$$

$$\left.\begin{aligned}\text{Maximize}\quad & z = x^T c + x^T P x \\ \text{Subject to}\quad & Dx = e\end{aligned}\right\}$$

where $x \in \Re^n$. We assume that the conditions $Dx=e$ comprise a non-degenerate set with $m<n$. If $m>n$, then the system is over specified and no solution may occur. In the case that $m=n$, then one solution exists at the point $x_0=D^{-1}e$ providing $|D| \neq 0$. Hence, no optimization is possible or necessary.

Constructing the Lagrangian, we find that $$L = x^T c + x^T P x + \lambda^T (Dx - e) \quad (3)$$

where m Lagrange multipliers have been introduced. From the Lagrangian, we obtain the global extremum $$\begin{Bmatrix} x_o \\ \lambda_o \end{Bmatrix} = \begin{Bmatrix} 2P & D^T \\ D & 0 \end{Bmatrix}^{-1} \begin{Bmatrix} -c \\ e \end{Bmatrix} \quad (4)$$

where it is assumed that the matrix inversion is possible.

To particularize this result to the minimization of the current metric for the MSS, we begin by focusing solely on the static and quasi-static cases, thus assuming that the source currents are either held constant or ramped relatively slowly in time. Given n magnetomotive sources (or, in this sense, actuators), we wish to operate the sources with minimal currents so that a desired magnetic field may be specified for a selected point in space $x_0$ where $x_0 \in \Re$. The total magnetic field at any point x, b(x), is the linear superposition of the magnetic fields due to each source evaluated at x:

$$b(x) = \sum_{i=1}^{n} b_i(x) \quad (5)$$

Since $b_i(x)$ is linear with respect to its corresponding source current, $I_i$, the above may be written as $$b(x, I) = \sum_{i=1}^{n} \overline{B}_i(x) I_i \quad (6)$$

where $\overline{B}_i(x)$ consists of the three current-independent components of the magnetic field for each source. If we define the 3×n matrix $\overline{B}(x)$ as $$\overline{B}(x) = \{\overline{B}_1(x) | \overline{B}_2(x) | \ldots | \overline{B}_n(x)\} \quad (7)$$

and we write the currents as the n-element column vector I, then Eq. (6) and Eq. (7) can be combined to form the matrix relationship $$b(x,I) = \overline{B}(x) I \quad (8)$$

Note that n>3 is assumed in order for an optimization to be made for a desired magnetic field b (which consists of three components). If n<3 (i.e., two actuators or less), the system is over constrained and no solution exists unless there is a degeneracy in Eq. (8). If n=3, then the solution to the currents, $I_0$, is given by $$I_0 = \overline{B}^{-1}(x_0) b.$$

We now focus our attention on the current metric defined as $$z(I) = \sum_{i=1}^{n} I_i^2 = I^T I \quad (9)$$

While the metric does not specifically limit the individual currents, it does serve as a means of penalizing those solutions that are associated with strong currents. The problem of finding an optimal set of currents (for n>3 sources) may now be stated in a form for which there are m=3 equality constraints:

$$\begin{aligned} \text{Maximize} \quad & z(I) = -I^T I \\ \text{Subject to} \quad & \overline{B}(x_o) I = b \end{aligned} \quad (10)$$

It is noted that we could just as easily minimize the current metric above without loss of generality; however, writing the problem in the form of Eq. (10) is convenient for our present purposes. Since the metric of Eq. (10) is a concave function, the solution for the currents is:

$$\begin{Bmatrix} I_o \\ \lambda_o \end{Bmatrix} = \begin{Bmatrix} -2I_D & \overline{B}(x_o)^T \\ \overline{B}(x_o) & 0 \end{Bmatrix}^{-1} \begin{Bmatrix} 0 \\ b \end{Bmatrix} \quad (11)$$

where $I_D$ is the identity matrix. Inspection of Eq. (10) reveals that only one extremum (and hence, the global maximum) of the negative current metric can occur. Eq. (11) thus provides the solution for the coil currents $I_0$ in the MSS given a specified magnetic field.

While the current metric is sufficient in restricting the currents to small values in most cases, it does not minimize them. It is possible that a larger metric results when smaller currents are distributed over several sources. For example, say the desired field for a four source system corresponds to the optimal set of currents $I_0^T = \{10\ 80\ 10\ 80\}(A)$ for which $z(I_0) = 13000\ A^2$. If the individual currents must be less than 75 A, another (possibly more useful solution in some cases) would correspond to $I_0^T = \{60\ 70\ 60\ 70\}(A)$, for which $z(I_0) = 17000\ A^2$, providing the currents generate the same magnetic field. Including the k linear current limits $DI \geq e$ into Eq. (10), our general n-source, linearly constrained problem is stated as $$\begin{aligned} \text{Maximize} \quad & z = -I^T I \\ \text{Subject to} \quad & \overline{B}(x_o) I = b \\ & DI \geq e \end{aligned} \quad (12)$$

Since it is more commonly found that the n actuators possess upper and lower limits according to $|I_i| \leq I_{max}$ (i=1, ..., n), the constraints form a closed and bounded set providing the specification of B still holds for the range of allowed currents. The problem becomes $$\begin{aligned} \text{Maximize} \quad & z(i) = -I^T I \\ \text{Subject to} \quad & \overline{B}(x_o) I = b \\ & \begin{Bmatrix} I_D \\ -I_D \end{Bmatrix} I \geq -\begin{Bmatrix} I_{max} \\ I_{max} \end{Bmatrix} \end{aligned} \quad (13)$$

where k=2n inequality constraints with $I_{max,i} = I_{max}$ for i=1, ..., n have been introduced. The conditions that must be satisfied in order for maximum to exist are given by $$\begin{aligned} & -2I_o + \mu_o^T \begin{Bmatrix} I_D \\ -I_D \end{Bmatrix} + \lambda_o^T \overline{B}(x_o) = 0 \\ & \mu_o^T \left( \begin{Bmatrix} I_D \\ -I_D \end{Bmatrix} I_o + \begin{Bmatrix} I_{max} \\ I_{max} \end{Bmatrix} \right) = 0 \\ & \overline{B}(x_o) I_o = b \\ & -I_{max} \leq I_o \leq I_{max} \\ & \mu_o \geq 0 \end{aligned} \quad (14)$$

The possible $2^{2n} = 4^n$ solutions of the above set of equations follow from Eq. 29 of Appendix B where individual constraints are activated among the 2n inequality conditions. As was previously discussed, when the activated constraints combined with the equality constraints outnumber the degrees of freedom, the system of equations become over specified and no solution need be calculated. For those cases in which the system of equations is exactly specified, the solution must be checked against the inequality constraints to deem it viable. There remain $$4^n = \sum_{i=n-3}^{2n} \frac{2n!}{(2n-i)! i!}$$

of the $4^n$ cases which can be solved (assuming a solution exists). Those solutions that satisfy the constraints are saved and the set that results in the maximum value of $z(I_0) = -I_0^T I_0$ [or minimum of $z(I_0) = I_0^T I_0$] is reported as the optimal solution.

It is sometimes useful to restrict the magnetically generated force on a small permanent moment. For example, quasi-static systems such as magnetic suspensions and the MSS can profit from an inclusion of force constraints if higher currents are acceptable. The $x_0$, $f(x_0)$, generated on a small permanent magnetic moment, m, due to a magnetic field, b, is given by $$f(x_0) = \nabla(m^T b(x))|_{x=x_0} \qquad (15)$$

An easier notation for the present purposes involves writing the three component of the force as $$f_i(x_o) = m^T \frac{\partial b}{\partial x_i}(x_o) \qquad (i = 1, 2, 3) \qquad (16)$$

For those problems in which the moment is allowed to align with the magnetic field $$\left[\text{i.e., } m = \frac{\|m\|}{\|b\|} b(x_o)\right],$$

Eq. (16) is transformed into $$\left(f_i(x_o) = \frac{\|m\|}{\|b(x_o)\|} b(x_o)^T \left(\frac{\partial b(x)}{\partial x_i}\right)\right)_{x=x_o} \qquad (i = 1, 2, 3) \qquad (17)$$

where the strength of the moment $\|m\|$ is known. Combining the results of Eq. (17) with Eq. (8), a somewhat complicated problem arises for those cases in which the orientation of the magnetic field at $x_0$ is unrestricted. This can be seen in the nonlinear form of $$f_i(x_o, I) = \qquad (18)$$

$$\|m\| I^T \overline{B}(x_o)^T \left(\frac{\partial \overline{B}}{\partial x_i}(x_o)\right) \frac{I}{\sqrt{I^T \overline{B}(x_o)^T \overline{B}(x_o) I}} \qquad (i = 1, 2, 3)$$

For the present purposes, only those cases that rely on a specified magnetic field are considered.

Using the current dependence of the magnetic sources and a predetermined magnetic field b where $b = \overline{B}(x_0)I$, Eq. (17) can be written in two forms. The linear and quadratic forms are given by, respectively, $$f_i(x_o, I) = \frac{\|m\|}{\|b\|} b^T \left(\frac{\partial \overline{B}}{\partial x_i}(x_o)\right) I \qquad (i = 1, 2, 3) \qquad (19)$$

and $$f_i(x_o, I) = \frac{\|m\|}{\|b\|} I^T \overline{B}(x_o)^T \left(\frac{\partial \overline{B}}{\partial x_i}(x_o)\right) I \qquad (i = 1, 2, 3) \qquad (20)$$

While the form of Eq. (19) may appear more useful, at least seven actuators must be present in order to overcome the six constraints due to the specification of the magnetic field and force. If it is important that both the force and field be specified and if there are a sufficient number of actuators, then the work follows from Eq. (10)–Eq.(14) with the three additional force constraints being included into the field constraints. If there are exactly six actuators, then there exists a unique solution to the problem at $$I_o = \left\{ \begin{pmatrix} \left(\frac{\|m\|}{\|b\|} \nabla(b^T \overline{B}(x))|\right)_{x=x_o} \\ \overline{B} \end{pmatrix}^{-1} \right\} \begin{Bmatrix} f \\ b \end{Bmatrix} \qquad (21)$$

providing the operating matrix is invertible and the currents are unbounded.

More often than not, the experimenter is more concerned with either minimizing a component of the force or the strength of the force with respect to a limited range of currents and a desired magnetic field rather than specifying a specific value of the force. If examining a component of the force, Eq. (20) is generalized so that the force along the unit vector u ($\|u\|=1$) is minimized. The force component of interest becomes $u^T f(x_0, I)$ and the problem is written as $$\text{Maximize } z(I) = -u^T f(x_o, I) = \qquad (22)$$

$$-\frac{\|m\|}{\|b\|} \left( \sum_{i=1,2,3} u_i I^T \overline{B}(x_o)^T \left(\frac{\partial \overline{B}}{\partial x_i}(x_o)\right) I \right)$$

Subject to $\overline{B}(x_o)I = b$ $$\begin{Bmatrix} I_D \\ -I_D \end{Bmatrix} I \geq -\begin{Bmatrix} I_{\max} \\ I_{\max} \end{Bmatrix}$$

Likewise, if the force strength is to be minimized, a quadratic form is obtained for the objective function by squaring the force components of Eq. (19):

$$\text{Maximize } z(I) = -f(x_o, I)^T f(x_o, I) = \qquad (23)$$

$$-\left(\frac{\|m\|}{\|b\|}\right)^2 \left( \sum_{i=1,2,3} I^T \left(\frac{\partial \overline{B}^T}{\partial x_i}(x_o)\right) bb^T \left(\frac{\partial \overline{B}}{\partial x_i}(x_o)\right) I \right)$$

Subject to $\overline{B}(x_o)I = b$ $$\begin{Bmatrix} I_D \\ -I_D \end{Bmatrix} I \geq -\begin{Bmatrix} I_{\max} \\ I_{\max} \end{Bmatrix}$$

If it is desired that the force be maximized rather than minimized, then the negative sign to the objective function is left off in Eq. (22) and Eq. (23). The conditions that establish the existence of a minimum or maximum follow from Eq. 27 of Appendix A. Note that only for force minimizations may the currents be left unbounded.

Portions of the above description of hardware and control methods and apparatuses refer to a six-coil system for use in certain applications in the medical field. However, the invention is not limited to systems having any particular number of coils, and is suitable for applications (including magnetic surgery applications) for which other coil numbers and arrangements may be preferable. For example, it is possible to remove the front coil of the above system, and to bring side coils closer together. The resulting five-coil arrangement would allow the patient to be more accessible to a surgeon, an important consideration for some surgical procedures. Other arrangements with different numbers of coils may be particularly useful with some other types of operations, for example, those at locations in the body other than the head. (It should be noted that it is not required by the invention that embodiments of multiple coil systems necessarily have coils that are operated in pairs, opposed or otherwise. Thus, the invention also encompasses systems having arbitrary numbers of coils.)

Figure 5:
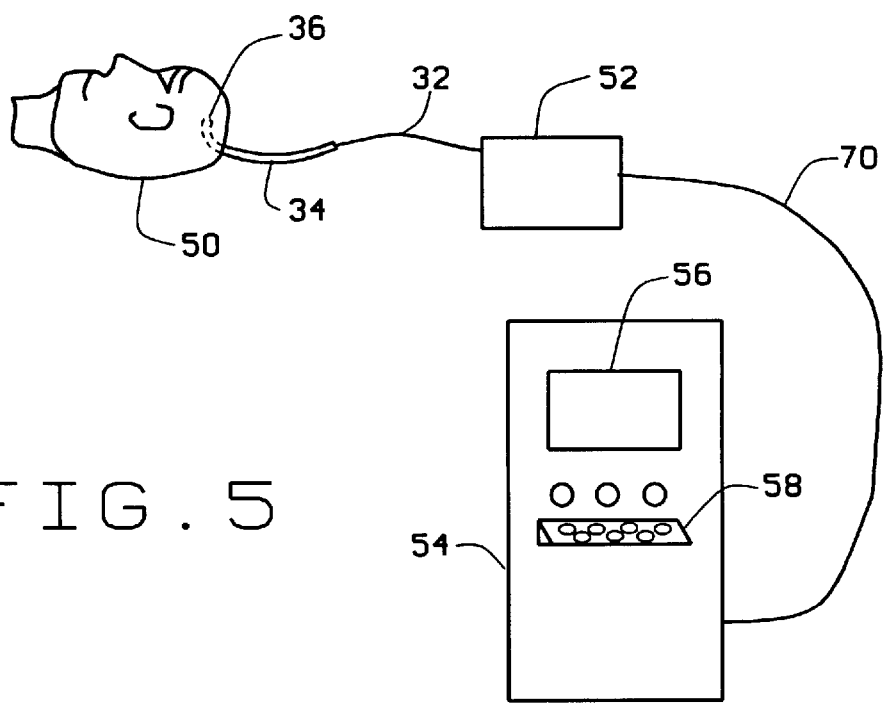
FIG. 5 is a block diagram of a portion of a Magnetic Stereotaxis System in accordance with the invention.
Figure 6:
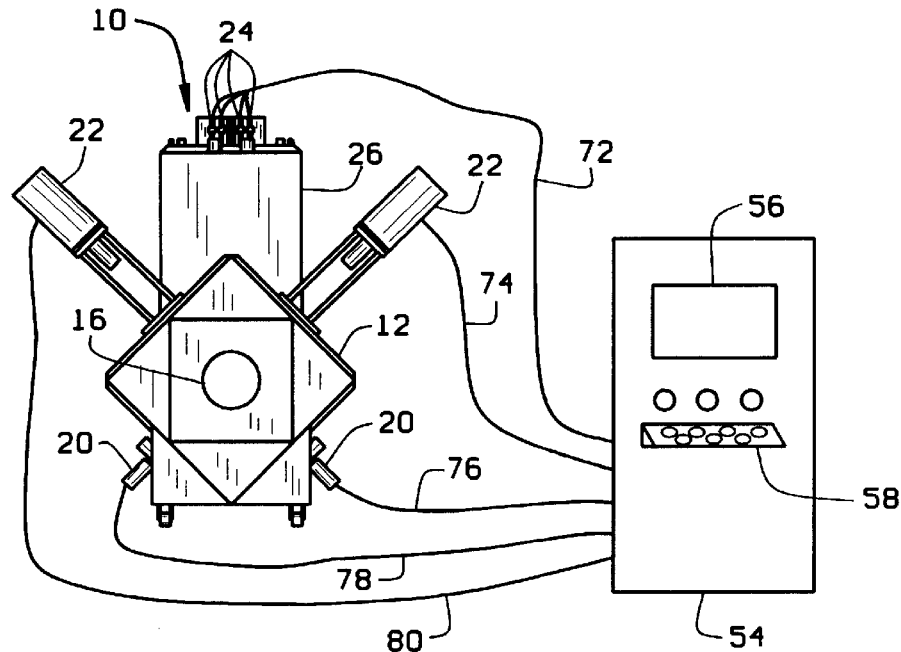
FIG. 6 is a block diagram of another portion of the Magnetic Stereotaxis System of FIG. 5.

An apparatus that controls coil currents and magnetic tip advancement is illustrated in block diagram form in FIG. 5 and FIG. 6. (It should be noted that not all external connections to console 54 are shown in each figure.) FIG. 5 shows a catheter 34 with metal tip 36 having a magnetic implant 30 inside (see also FIG. 3A). This catheter is shown with tip 36 already implanted in the brain of a patient 50, at the beginning stages of a medical procedure. Push wire 32 is operatively coupled to a motor in an advancement mechanism 52 that a surgeon may control by issuing commands at a console 54. Console 54 includes a real-time computer having a display screen 56 and an operator control 58, which may be a keypad or other convenient data entry device. Although the apparatus is described in conjunction with operations on a catheter in the brain of patient 50, it should be recognized that the inventive apparatus and techniques may be applied to other living tissues as well, or in other media, living or not, through which it may be desired to push a magnetic tip on a flexible push wire or guide wire.

Referring now to FIG. 6., the head of patient 50 (not shown in FIG. 6) is disposed in opening 16 of coil apparatus 10, as the surgeon operates the inventive apparatus. Console 54 contains a processor such as a digital computer responsive to operator commands input through operator control 58 and to cameras 20 for controlling a power supply (not shown) that supplies currents to coil terminals 24 to generate the required magnetic fields. To fully automate the catheter movement, advancement mechanism 52 may also be controlled by the processor. Cameras 20 and X-ray generators inside magnetic shields 22 provide magnetic tip position information to the processor in console 54. It will be recognized, however, that other suitable means for providing position information may be substituted for the cameras 20 and X-ray generators.

To perform a procedure, a surgeon would observe the initial position of the magnetic tip 36 with the aid of console 54 and plan a path through the tissue of patient 50 (in this case, the brain) to a point at which treatment is to be delivered. The surgeon may also choose a step size and an advancement rate, although either or both of these may be preprogrammed. The surgeon then activates the system by issuing appropriate commands through console 54.

In response to these commands, the processor inside console 54 computes positions of metal tip 36 from data received from cameras 20, as well as vectors $V_{step}$ and the coil currents necessary to move metal tip 36 along the desired path at the beginning of each step, and applies the computed currents to the coils while advancement mechanism 52 advances metal tip 36 through the tissue. Correction vectors $V_{correction}$ are stored in memory to provide the necessary history for the PID calculations. The advancement continues until the endpoint of the path is reached. Although the advancement occurs in steps, the positions and coil currents can typically be calculated rapidly enough to make the advancement of magnetic tip 36 essentially continuous.

If necessary, the surgeon may intervene by stopping movement of the catheter or by changing its course before the originally planned endpoint is reached. When a course change is made, the correction vectors $V_{correction}$ stored in the memory of the processor during advancement on the aborted path are either cleared from memory or simply ignored so that these vectors do not influence the calculations performed to direct the magnetic tip along the new path.

Figure 7:
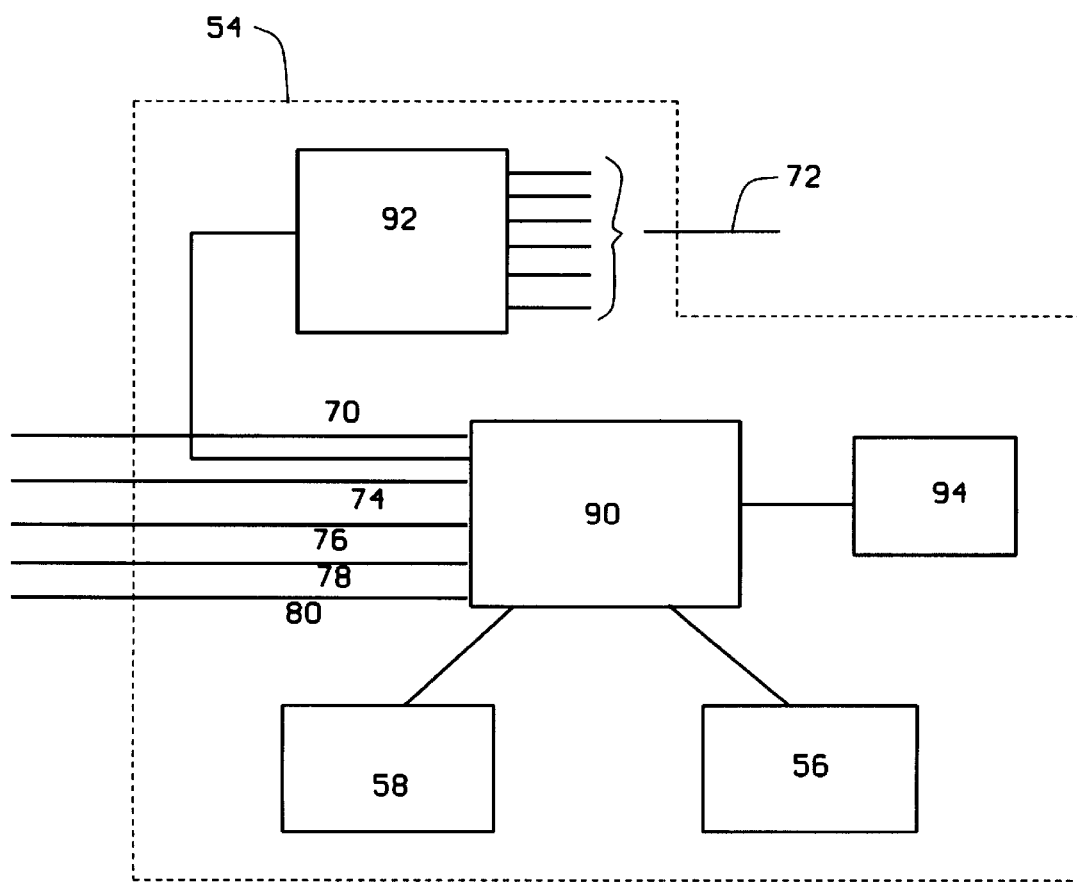
FIG. 7 is a block diagram of a configuration of a processor suitable for use in the MSS of FIGS. 5 and 6.

FIG. 7 shows a simple block diagram of a manner in which a processor 90 may be configured for use in console 54. Processor 90 is provided with operator control 58 (which may, for example, be a keyboard) for accepting operator input and a display 56 for displaying information to the operator. Inputs and outputs 70, 74, 76, 78, and 80 corresponding to those shown in FIG. 5 and FIG. 6 are provided to obtain data required for sensing position of the catheter tip and for controlling the X-ray fluoroscopes and superconducting coils inside helmet 12. A random access memory 94 is provided for storing values of $V_{correction}$, and a programmable power supply 92 is provided to supply current to the superconducting coils through a plurality of lines 72 in accordance with the current values computed by processor 90. Although programmable power supply 92 is shown as a power supply having multiple, independent, programmable outputs, it will be readily appreciated that a plurality of individual power supplies may be used as an alternative to the power supply shown in the figure.

A document describing the structure of a computer program to operate a processor in accordance with the invention is attached as Appendix A. Computer programs written in the C++ computer language that determine and control current applied to the coils in accordance with the invention appear in Appendix B. A more detailed treatment of quadratic optimizations pertaining to current solutions for magnetic field sources appears in Appendix C. A more detailed treatment of the generation of a magnetic field for a circular coil of distributed current appears in Appendix D. A detailed mathematical treatment of the summation of field components for single and multiple coils appears in Appendix E, which continues the discussion of the material in Appendix D.

The above-described embodiments are intended to be illustrative only. For example, there are numerous types of magnetic surgery procedures for which the coil systems described and the method of calculating and providing currents to generate fields and forces are important, but for which there is no planned or predetermined path and no feedback. Instead, a device in accordance with the general principles of the invention can provide magnetic guidance of a tip of a surgical device such as a catheter, endoscope, etc. The invention can be readily adapted so that a surgeon, under guidance from an imaging system, uses the magnetic system to negotiate otherwise difficult turns and movements of the surgical device as he or she pushes a device along the interior of a vessel. It will also be recognized that many of the inventive methods and apparatuses may be used in conjunction with any coil in a non-resonant circuit that applies a magnetic force on a suspended or embedded object that is magnetically moveable. Many other modifications falling within the spirit of the invention will be apparent to those skilled in the art. Therefore, the scope of the invention should be determined by reference to the claims below and the full range of equivalents in accordance with applicable law.

What is claimed is:

1. A method for controlling movement of a catheter through a medium, the method comprising the steps of:
    (a) mechanically pushing a flexible catheter having a magnetic tip through the medium; and
    (b) applying a magnetic field having a magnitude and an orientation effective to guide the mechanically-pushed catheter tip in a predetermined direction.

2. The method of claim 1 and further comprising the steps of sensing catheter tip positions, and adjusting the applied magnetic field so that the catheter tip advances stepwise at least approximately along a predetermined path.

3. The method of claim 1 and further comprising the steps of:
    sensing catheter tip positions;
    generating a signal indicative of the position of the catheter tip;
    determining a correction vector between the position of the catheter tip and the predetermined path at least partially in response to said generated signal; and
    adjusting the applied magnetic field at least partially in response to the determined correction vector so that the catheter tip advances at least approximately along a predetermined path.

4. The method of claim 3 further comprising the step of storing correction vectors in a memory, and wherein the determining step comprises determining the adjustment at least partially in response to a presently-determined correction vector and at least one of the previously stored correction vectors.

5. The method of claim 1 wherein the step of applying a magnetic field comprises the step of applying currents to a plurality of superconducting coils.

6. The method of claim 5 wherein the currents are selected to minimize a predetermined current metric.

7. The method of claim 5 wherein the currents are selected to minimize a current-limiting constraint set.

8. The method of claim 1 wherein the step of mechanically pushing the catheter comprises the step of pushing the catheter through living tissue.

9. The method of claim 8 wherein the living tissue is a human brain.

10. The method of claim 8 further comprising the steps of sensing catheter tip positions, and adjusting the applied magnetic field so that the catheter tip advances stepwise at least approximately along a predetermined path.

11. The method of claim 10 further comprising the steps of:
generating a signal indicative of the position of the catheter tip;
determining a correction vector between the position of the catheter tip and the predetermined path at least partially in response to said signal;
and wherein the adjustment step comprises determining the adjustment to the applied magnetic field at least partially in response to the determined correction vector.

12. The method of claim 11 further comprising the step of storing correction vectors in a memory, and wherein the determining step comprises determining the adjustment at least partially in response to a presently-determined correction vector and at least one previously stored correction vector.

13. The method of claim 11 further comprising the step of storing correction vectors in a memory, and wherein the determining step comprises determining the adjustment at least partially in response to a rate of change of correction vectors in a previous step.

14. The method of claim 11 further comprising the step of storing correction vectors in a memory, and wherein the determining step comprises determining the adjustment at least partially in response to an anticipated future error with respect to a planned path.

15. The method of claim 8 wherein the step of applying a magnetic field comprises the step of applying currents to a plurality of superconducting coils.

16. The method of claim 15 wherein the currents are selected to minimize a predetermined current metric.

17. The method of claim 15 wherein the currents are selected to minimize a current-limiting constraint set.

18. A method for stepwise movement of a catheter having a magnetic tip in a magnetic field, the method comprising the steps of:
(a) selecting a desired path of the catheter through living tissue;
(b) inserting the catheter tip into the living tissue;
(c) determining actual positions of the magnetic tip and associated correction vectors, the correction vectors representing differences between locations on the desired path and the actual positions of the magnetic tip;
(d) storing said correction vectors in a memory; and
(e) applying a magnetic field adjusted to achieve movement of the magnetic tip at least approximately along the desired path, the adjustment depending upon at least one stored correction vector;
wherein the determining step comprises determining a point $p_1$ on the desired path closest to the then actual position of the magnetic tip and computing a vector $V_{correction}$ representing the distance and correction from the then actual position of the magnetic tip to the point $p_1$; and
wherein the step of applying the magnetic field comprises:
selecting a point $p_2$ a predetermined distance from $p_1$ along the desired path;
calculating a vector $V_{path}$ directed from $p_1$ to $p_2$; and
changing the magnetic field to move the magnetic tip in accordance with a function of a vector $V_{step}$, where $$V_{step} = V_{path} + V_{lag} + g \frac{V_{correction}}{|V_{correction}|},$$

in which:
$V_{lag}$ is a lag-correction vector pointing to an inside of a local curvature of the planned path at point $p_2$; and
g is a gain factor.

19. A method for stepwise movement of a catheter having a magnetic tip in a magnetic field, the method comprising the steps of:
(a) selecting a desired path of the catheter through living tissue;
(b) inserting the catheter tip into the living tissue;
(c) determining actual positions of the magnetic tip and associated correction vectors, the correction vectors representing differences between locations on the desired path and the actual positions of the magnetic tip;
(d) storing said correction vectors in a memory; and
(e) applying a magnetic field adjusted to achieve movement of the magnetic tip at least approximately along the desired path, the adjustment depending upon at least one stored correction vector;
wherein the applying step is performed a plurality of times, each time resulting in movement of the magnetic tip from a then current position to another position, and at least some of the applying steps are dependent upon the correction vectors determined for positions of the magnetic tip prior to the then current position, and further wherein the step of storing correction vectors comprises retaining at least two consecutively determined correction vectors in memory, each determined for positions of the magnetic tip prior to the then current position, and the applied magnetic field is dependent upon a function of at least the two consecutively determined correction vectors.

20. The method of claim 19 wherein:
(a) the step of determining the correction vectors comprises, for each correction vector:
determining a point $p_1$ on the desired path closest to the then current position of the magnetic tip; and
determining a correction vector $V_{correction}$ representing the distance and direction from the then current position of the magnetic tip to the point $p_1$; and
(b) the step of applying the magnetic field further comprises:

selecting a point p2 a predetermined distance further along the desired path from $p_1$;

calculating a vector $V_{path}$ representing the distance and direction from $p_1$ to $p_2$;

changing the magnetic field to move the magnetic tip in accordance with a function of a vector $V_{step}$, where $$V_{step} = V_{path} + V_{lag} + g \frac{V_{correction}}{|V_{correction}|},$$

and where:

$V_{lag}$ is a lag-correction vector pointing to an inside of a local curvature of the planned path at point $p_1$;

$$g=\|k_p V_{c(n)} + k_i (V_{c(n)} + V_{c(n-1)} + V_{c(n-2)}) + k_d (V_{c(n)} - V_{c(n-1)})\|,$$

where $k_p$, $k_i$, and $k_d$ are predetermined constants; and $V_{c(n)}$, $V_{c(n-1)}$, and $V_{c(n-2)}$ are a correction vector determined for the then current position of the magnetic tip, a correction vector determined for a position of the magnetic tip before an immediately preceding magnetic field application, and a correction vector determined for a position of the magnetic tip before a second immediately preceding magnetic field application, respectively.

21. A method for stepwise movement of a catheter having a magnetic tip in a magnetic field, the method comprising the steps of:

(a) selecting a desired path of the catheter through living tissue;

(b) inserting the catheter tip into the living tissue;

(c) determining actual positions of the magnetic tip and associated correction vectors, the correction vectors representing differences between locations on the desired path and the actual positions of the magnetic tip;

(d) storing said correction vectors in a memory; and (e) applying a magnetic field adjusted to achieve movement of the magnetic tip at least approximately along the desired path, the adjustment depending upon at least one stored correction vector;

(f) selecting a minimum radius of curvature for movement of the magnetic tip;

and wherein the step of applying the magnetic field comprises constraining said magnetic field so that the magnetic tip follows a trajectory having a curvature not less than the selected minimum radius of curvature.

22. A method for stepwise movement of a catheter having a magnetic tip in a magnetic field, the method comprising the steps of:

(a) selecting a desired path of the catheter through living tissue;

(b) inserting the catheter tip into the living tissue;

(c) determining actual positions of the magnetic tip and associated correction vectors, the correction vectors representing differences between locations on the desired path and the actual positions of the magnetic tip;

(d) storing said correction vectors in a memory; and (e) applying a magnetic field adjusted to achieve movement of the magnetic tip at least approximately along the desired path, the adjustment depending upon at least one stored correction vector;

wherein the step of selecting a desired path comprises:

selecting an ideal path;

approximating the ideal path by parametric cubic polynomials, whereby the approximated path becomes the desired path; and storing a representation of the parametric cubic polynomials in a memory.

23. The method of claim 22 further comprising selecting a minimum radius of curvature for movement of the magnetic tip; and wherein the step of applying the magnetic field comprises constraining said magnetic field so that the magnetic tip follows a trajectory having a curvature not less than a predetermined minimum radius of curvature.

24. A method for stepwise movement of a catheter having a magnetic tip in a magnetic field, the method comprising the steps of:

(a) selecting a desired path of the catheter through living tissue;

(b) inserting the catheter tip into the living tissue;

(c) determining actual positions of the magnetic tip and associated correction vectors, the correction vectors representing differences between locations on the desired path and the actual positions of the magnetic tip;

(d) storing said correction vectors in a memory; and (e) applying a magnetic field adjusted to achieve movement of the magnetic tip at least approximately along the desired path, the adjustment depending upon at least one stored correction vector;

wherein the application step comprises controlling currents through a plurality of coils, the currents in the coils are characterized by a root mean square value, and the application step includes minimizing the root mean square value of the coil currents for each application.

25. The method of claim 24 wherein the application step comprises adjusting currents in three pairs of coils.

26. A method for stepwise movement of a catheter having a magnetic tip in a magnetic field, the method comprising the steps of:

(a) selecting a desired path of the catheter through living tissue;

(b) inserting the catheter tip into the living tissue;

(c) determining actual positions of the magnetic tip and associated correction vectors, the correction vectors representing differences between locations on the desired path and the actual positions of the magnetic tip;

(d) storing said correction vectors in a memory; and (e) applying a magnetic field adjusted to guide movement of the magnetic tip at least approximately along the desired path, the adjustment depending upon at least one stored correction vector; and (f) pushing the catheter with a force not solely due to the applied magnetic field to thereby move the catheter under guidance of the magnetic field.

27. The method of claim 26 wherein the desired path has an endpoint, and the applying and pushing steps are performed a plurality of times until the magnetic tip approximately reaches the endpoint.

28. The method of claim 26 wherein the determining step comprises determining a point $p_1$ on the desired path closest to the then actual position of the magnetic tip and computing a vector $V_{correction}$ representing the distance and correction from the then actual position of the magnetic tip to the point $p_1$.

29. The method of claim 26 wherein the applying step comprises applying the magnetic field in accordance with a predetermined function of at least a present correction vector, a previously stored correction vector, a lag-correction vector, and a vector along the desired path having a predetermined length, so that the magnetic tip advances at least approximately along the desired path when pushed by the catheter.

30. The method of claim 29 wherein the determining step comprises determining a point $p_1$ on the desired path closest to the then actual position of the magnetic tip and computing a vector $V_{correction}$ representing the distance and correction from the then actual position of the magnetic tip to the point $p_1$.

31. The method of claim 26 wherein the applying and pushing steps are performed a plurality of times, each time resulting in movement of the magnetic tip from a then current position to another position, and at least some of the applying steps are dependent upon the correction vectors determined for positions of the magnetic tip prior to the then current position.

32. A method for moving a catheter having a magnetic tip disposed in a magnetic field stepwise along a path, the method comprising performing the steps of claim 26 first for a first desired path and then for a second desired path, and wherein applications of the magnetic field are responsive solely to correction vectors determined with respect to the respective paths.

33. The method of claim 26 wherein the application step comprises controlling currents through a plurality of super-conducting coils.

34. The method of claim 33 wherein the application step comprises adjusting currents in three pairs of coils.

35. A method for controlling movement of a magnetic implant through living tissue, the method comprising the steps of:

(a) applying nonmagnetic forces to a flexible attachment mechanically attached to the implant; and (b) magnetically steering the implant in a predetermined direction through the living tissue as it is pushed.

36. The method of claim 35 wherein the magnetic implant comprises a magnetically-tipped endoscope, and further comprising inserting the magnetic tip of the endoscope into the living tissue.

37. The method of claim 36 wherein the implant comprises a surgical device and the steering step comprises navigating the surgical device along the interior of a vessel.

* * * * *

UNITED STATES PATENT AND TRADEMARK OFFICE
CERTIFICATE OF CORRECTION

| | | |
|---|---|---|
| PATENT NO. | : 6,015,414 | Page 1 of 161 |
| APPLICATION NO. | : 08/920446 | |
| DATED | : January 18, 2000 | |
| INVENTOR(S) | : Peter R. Werp et al. | |

It is certified that error appears in the above-identified patent and that said Letters Patent is hereby corrected as shown below:

Insert the following Appendix A, B, C, and D (submitted on August 29, 1997) after Column 14, Line 43.

Signed and Sealed this

Twenty-fourth Day of May, 2011

David J. Kappos
*Director of the United States Patent and Trademark Office*

APPENDIX "A"

MAGNAV DESIGN DOCUMENT

Revision 1.0

|  | NAME | DATE |
|---|---|---|
| PREPARED BY: | Francis M. Creighton | |
| REVIEWED BY: | Walter Blume | |
|  | Michael Lawson | |
|  | Delsie Boyde | |
| APPROVED BY: | Peter Werp | |

Stereotaxis, Inc.

2730 Sand Hill Road, Suite 200

Menlo Park, CA 94025-7067

CERTIFICATE OF CORRECTION (continued)
U.S. Pat. No. 6,015,414

1. INTRODUCTION ..................................................................................................................... 9
   1.1 PURPOSE ............................................................................................................................. 9
   1.2 SCOPE .................................................................................................................................. 9
   1.3 DEFINITION AND ACRONYMS ............................................................................................ 9
2. REFERENCES ......................................................................................................................... 9
3. MAGNETIC NAVIGATION SOFTWARE ........................................................................ 10
   3.1 MODULE DECOMPOSITION .............................................................................................. 10
      *3.1.1 Magnetic Navigation Interface Software* .................................................................. 10
      *3.1.2 Field matching Software* ........................................................................................... 10
      *3.1.3 Quadratic Optimization Software* ............................................................................. 10
      *3.1.4 Field Computation Software* ..................................................................................... 10
      *3.1.5 Field Generation Software* ........................................................................................ 11
      *3.1.6 Matrix Allocation Software* ....................................................................................... 11
   3.2 DATA DESCRIPTION .......................................................................................................... 11
      *3.2.1 Magnetic Navigation Interface Software* .................................................................. 11
      *3.2.2 Field Matching Software Description* ...................................................................... 11
      *3.2.3 Quadratic Optimization Software Description* ......................................................... 11
      *3.2.4 Field Computation Software Description* ................................................................. 12
      *3.2.5 Field Generation Software Description* .................................................................... 12
      *3.2.6 Matrix Allocation Software Description* ................................................................... 13
4. PUBLIC SOFTWARE: MAGNAV INTERFACE SOFTWARE ...................................... 14
   4.1 MNIS DESCRIPTION AND INTERFACE ............................................................................ 14
      *4.1.1 MagNavCalcB()* ......................................................................................................... 14
      *4.1.2 MagNavCalcF()* ......................................................................................................... 14
      *4.1.3 MagNavCalcPermF()* ................................................................................................ 15
      *4.1.4 MagNavDeinit()* ......................................................................................................... 16
      *4.1.5 MagNavFieldMatch()* ................................................................................................ 16
      *4.1.6 MagNavInit()* .............................................................................................................. 17
      *4.1.7 MagNavSetFilePath()* ................................................................................................ 17
      *4.1.8 MagNavSetParam()* ................................................................................................... 18
      *4.1.9 MNIS Structures* ........................................................................................................ 18
         4.1.9.1 MNIS Public Structures ......................................................................................... 18
            4.1.9.1.1 mag_nav_param .............................................................................................. 18

*4.1.10 MNIS Enumerations* ........................................................................................................... *19*

4.1.10.1 MNIS Public Enumerations .................................................................................... 19

4.1.10.1.1 mag_nav_error_codes ................................................................................ 19

*4.1.11 MNIS Macros and Definitions* ............................................................................................ *19*

4.1.11.1 MNIS Public Definitions ............................................................................................ 19

4.2 MNIS DECOMPOSITION AND DETAILED DESIGN .................................................................. 19

*4.2.1 MagNavCalcB()* ................................................................................................................... *19*

*4.2.2 MagNavCalcF()* ................................................................................................................... *20*

*4.2.3 MagNavCalcPermF()* .......................................................................................................... *20*

*4.2.4 MagNavDeinit()* ................................................................................................................... *20*

*4.2.5 MagNavFieldMatch()* .......................................................................................................... *21*

*4.2.6 MagNavInit()* ....................................................................................................................... *22*

*4.2.7 MagNavSetFilePath()* .......................................................................................................... *22*

*4.2.8 MagNavSetParam()* ............................................................................................................. *23*

5. PRIVATE SOFTWARE: SUPPORT SOFTWARE ................................................................. 24

5.1 DESCRIPTION AND INTERFACE ................................................................................................. 24

*5.1.1 Field Matching Software Description* ................................................................................. *24*

5.1.1.1 FieldMatch_v1() ........................................................................................................... 24

5.1.1.2 SetMaxBAng() .............................................................................................................. 25

5.1.1.3 SetMaxBTol() ............................................................................................................... 25

5.1.1.4 SetMaxCurrent() ........................................................................................................... 25

5.1.1.5 FMS Enumerations ....................................................................................................... 26

5.1.1.5.1 FMS Public Enumerations ............................................................................. 26

5.1.1.5.1.1 field_match_error_codes ......................................................................... 26

5.1.1.6 FMS Macros and Definitions ....................................................................................... 26

5.1.1.6.1 FMS Public Definitions ................................................................................. 26

*5.1.2 Quadratic Optimization Software Description* .................................................................... *27*

5.1.2.1 CalcSymmetricMatrix() ................................................................................................ 27

5.1.2.2 ImproveLinSoln() .......................................................................................................... 27

5.1.2.3 LUBackSub() ................................................................................................................ 28

5.1.2.4 LUDecomp() ................................................................................................................. 28

5.1.2.5 LUSolve() ..................................................................................................................... 29

5.1.2.6 Mat_X_Vec() ................................................................................................................ 29

5.1.2.7 MaxQuad_wrt_EqCon() ................................................................................................ 29

5.1.2.8 SolveForLinearSet() ...................................................................................................... 30

5.1.2.9 SVD_BackSub() ........................................................................................................... 30

5.1.2.10 SVD_Solution() .......................................................................................................... 31

| | |
|---|---|
| 5.1.2.11 SVDecomp() | 31 |
| 5.1.2.12 SVZero() | 32 |
| 5.1.2.13 TwoPointNorm() | 32 |
| 5.1.2.14 QOS Macros and Definitions | 32 |
| 5.1.2.14.1 QOS Private Macros | 32 |
| 5.1.2.14.2 QOS Private Definitions | 33 |
| *5.1.3 Field Computation Software Description* | *34* |
| 5.1.3.1 Calc_B() | 34 |
| 5.1.3.2 Calc_d2B() | 34 |
| 5.1.3.3 Calc_dB() | 35 |
| 5.1.3.4 Calc_F() | 35 |
| 5.1.3.5 Calc_PermF() | 36 |
| 5.1.3.6 CalcBForCoil() | 36 |
| 5.1.3.7 CalcFieldData() | 37 |
| 5.1.3.8 CheckPositionVsTable() | 37 |
| 5.1.3.9 DeinitArrays() | 38 |
| 5.1.3.10 GetFieldElements() | 38 |
| 5.1.3.11 GetXYDataPlaneInfo() | 39 |
| 5.1.3.12 GetZDataPlaneInfo() | 39 |
| 5.1.3.13 InitArrays() | 40 |
| 5.1.3.14 LoadXYCoilInfo() | 40 |
| 5.1.3.15 LoadZCoilInfo() | 40 |
| 5.1.3.16 ReadCoilArray() | 41 |
| 5.1.3.17 ReportPathAssignment() | 41 |
| 5.1.3.18 ScaleFieldInfo() | 41 |
| 5.1.3.19 SetFilePath() | 42 |
| 5.1.3.20 Spline1D() | 42 |
| 5.1.3.21 Spline1DInt() | 43 |
| 5.1.3.22 Spline2D() | 43 |
| 5.1.3.23 Spline2DInt() | 44 |
| 5.1.3.24 FCS Structures | 45 |
| 5.1.3.24.1 FCS Public Structures | 45 |
| 5.1.3.24.1.1 coord_3d | 45 |
| 5.1.3.24.1.2 vec_3d | 45 |
| 5.1.3.24.1.3 der_3d | 45 |
| 5.1.3.24.1.4 der2_3d | 46 |
| 5.1.3.24.1.5 vec_der_3d | 46 |
| 5.1.3.24.1.6 vec_der2_3d | 46 |

- 5.1.3.24.2 FCS Private Structures ... 46
  - 5.1.3.24.2.1 data_file ... 46
  - 5.1.3.24.2.2 der_polar ... 47
  - 5.1.3.24.2.3 der2_polar ... 47
- 5.1.3.25 FCS Enumerations ... 47
  - 5.1.3.25.1 FCS Public Enumerations ... 47
    - 5.1.3.25.1.1 field_comp_errors ... 47
- 5.1.3.26 FCS Macros and Definitions ... 47
  - 5.1.3.26.1 FCS Private Macros ... 47
  - 5.1.3.26.2 FCS Public Definitions ... 47
  - 5.1.3.26.3 FCS Private Definitions ... 48

*5.1.4 Field Generation Software Description* ... *49*
- 5.1.4.1 DefineCoilArray() ... 49
- 5.1.4.2 FieldGenExe() ... 49
- 5.1.4.3 func_bl() ... 49
- 5.1.4.4 func_br() ... 50
- 5.1.4.5 GenerateFile() ... 50
- 5.1.4.6 NthTrapStage() ... 50
- 5.1.4.7 PolyInt() ... 51
- 5.1.4.8 QRomb() ... 51
- 5.1.4.9 SetCoilParam() ... 52
- 5.1.4.10 SetCurrent() ... 52
- 5.1.4.11 SetFuncParam() ... 52
- 5.1.4.12 SetInRad() ... 52
- 5.1.4.13 SetOutRad() ... 53
- 5.1.4.14 SetRombParam() ... 53
- 5.1.4.15 SetRombEPS() ... 53
- 5.1.4.16 SetRombFilNum() ... 54
- 5.1.4.17 SetRombJMAX() ... 54
- 5.1.4.18 SetRombK() ... 54
- 5.1.4.19 SetRombMaxIts() ... 54
- 5.1.4.20 SetThickness() ... 55
- 5.1.4.21 SetTurns() ... 55
- 5.1.4.22 ShowCoilParam() ... 55
- 5.1.4.23 ShowMenu() ... 56
- 5.1.4.24 Version() ... 56
- 5.1.4.25 FGS Structures ... 56
  - 5.1.4.25.1 FGS Private Structures ... 56

| | |
|---|---:|
| 5.1.4.25.1.1 coil_param | 56 |
| 5.1.4.25.1.2 integration_param | 56 |
| 5.1.4.26 FGS Enumerations | 57 |
| 5.1.4.26.1 FGS Public Enumerations | 57 |
| 5.1.4.26.1.1 field_gen_errors | 57 |
| 5.1.4.27 FCS Macros and Definitions | 57 |
| 5.1.4.27.1 FGS Private Macros | 57 |
| 5.1.4.27.2 FGS Private Definitions | 57 |
| *5.1.5 Matrix Allocation Software Description* | *58* |
| 5.1.5.1 fmatrix() | 58 |
| 5.1.5.2 free_fmatrix() | 58 |
| 5.1.5.3 free_fvector() | 59 |
| 5.1.5.4 free_ivector() | 59 |
| 5.1.5.5 fvector() | 59 |
| 5.1.5.6 ivector() | 60 |
| 5.1.5.7 MAS Enumerations | 60 |
| 5.1.5.7.1 MAS Public Enumerations | 60 |
| 5.1.5.7.1.1 mat_alloc_errors | 60 |
| 5.1.5.8 MAS Macros and Definitions | 60 |
| 5.1.5.8.1 Public MAS Macros | 60 |
| 5.1.5.8.2 Private MAS Definitions | 60 |
| 5.2 DECOMPOSITION AND DETAILED DESIGN | 61 |
| *5.2.1 Field Matching Software Description* | *61* |
| 5.2.1.1 FieldMatch_v1() | 61 |
| 5.2.1.2 SetMaxBAng() | 62 |
| 5.2.1.3 SetMaxBTol() | 62 |
| 5.2.1.4 SetMaxCurrent() | 62 |
| *5.2.2 Quadratic Optimization Software Description* | *63* |
| 5.2.2.1 CalcSymmetricMatrix() | 63 |
| 5.2.2.2 ImproveLinSoln() | 63 |
| 5.2.2.3 LUBackSub() | 63 |
| 5.2.2.4 LUDecomp() | 63 |
| 5.2.2.5 LUSolve() | 63 |
| 5.2.2.6 Mat_X_Vec() | 64 |
| 5.2.2.7 MaxQuad_wrt_EqCon() | 64 |
| 5.2.2.8 SolveForLinearSet() | 64 |
| 5.2.2.9 SVD_BackSub() | 64 |
| 5.2.2.10 SVD_Solution() | 65 |

- 5.2.2.11 SVDecomp() ... 65
- 5.2.2.12 SVZero() ... 65
- 5.2.2.13 TwoPointNorm() ... 65

5.2.3 Field Computation Software Description ... 66
- 5.2.3.1 Calc_B() ... 66
- 5.2.3.2 Calc_d2B() ... 66
- 5.2.3.3 Calc_dB() ... 66
- 5.2.3.4 Calc_F() ... 67
- 5.2.3.5 Calc_PermF() ... 67
- 5.2.3.6 CalcBForCoil() ... 67
- 5.2.3.7 CalcFieldData() ... 68
- 5.2.3.8 CheckPositionVsTable() ... 68
- 5.2.3.9 DeinitArrays() ... 68
- 5.2.3.10 GetFieldElements() ... 68
- 5.2.3.11 GetXYDataPlaneInfo() ... 69
- 5.2.3.12 GetZDataPlaneInfo() ... 69
- 5.2.3.13 InitArrays() ... 69
- 5.2.3.14 LoadXYCoilInfo() ... 69
- 5.2.3.15 LoadZCoilInfo() ... 69
- 5.2.3.16 ReadCoilArray() ... 70
- 5.2.3.17 ReportPathAssignment() ... 70
- 5.2.3.18 ScaleFieldInfo() ... 70
- 5.2.3.19 SetFilePath() ... 70
- 5.2.3.20 Spline1D() ... 70
- 5.2.3.21 Spline1DInt() ... 70
- 5.2.3.22 Spline2D() ... 70
- 5.2.3.23 Spline2DInt() ... 70

5.2.4 Field Generation Software Description ... 71
- 5.2.4.1 DefineCoilArray() ... 71
- 5.2.4.2 FieldGenExe() ... 71
- 5.2.4.3 func_bl() ... 73
- 5.2.4.4 func_br() ... 73
- 5.2.4.5 GenerateFile() ... 73
- 5.2.4.6 NthTrapStage() ... 75
- 5.2.4.7 PolyInt() ... 75
- 5.2.4.8 QRomb() ... 75
- 5.2.4.9 SetCoilParam() ... 75
- 5.2.4.10 SetCurrent() ... 76

| | |
|---|---|
| 5.2.4.11 SetFuncParam() | 76 |
| 5.2.4.12 SetInRad() | 76 |
| 5.2.4.13 SetOutRad() | 76 |
| 5.2.4.14 SetRombParam() | 76 |
| 5.2.4.15 SetRombEPS() | 76 |
| 5.2.4.16 SetRombFilNum() | 76 |
| 5.2.4.17 SetRombJMAX() | 76 |
| 5.2.4.18 SetRombK() | 76 |
| 5.2.4.19 SetRombMaxIts() | 76 |
| 5.2.4.20 SetThickness() | 76 |
| 5.2.4.21 SetTurns() | 76 |
| 5.2.4.22 ShowCoilParam() | 76 |
| 5.2.4.23 ShowMenu() | 77 |
| 5.2.4.24 Version() | 77 |
| *5.2.5 Matrix Allocation Software Description* | *78* |
| 5.2.5.1 fmatrix() | 78 |
| 5.2.5.2 free_fmatrix() | 78 |
| 5.2.5.3 free_fvector() | 78 |
| 5.2.5.4 free_ivector() | 78 |
| 5.2.5.5 fvector() | 78 |
| 5.2.5.6 ivector() | 78 |

1. Introduction

1.1 Purpose
This Software Design Description (SDD) describes the design and interrelationships of those functions dedicated to coil-current generation for magnetic navigation in the Magnetic Stereotaxis System (MSS). Software architecture, software components, interfaces, flowcharts, and data descriptions are addressed in the body of this text, termed the Magnetic Navigation (or "MagNav") Design Document (MNDD).

1.2 Scope
The MNDD is a software subsystem of the MSS which is accessed by the Surgeon Display (SD). The MSS is a neurosurgical tool allowing treatment of brain disorders by allowing the surgeon to operate via nonlinear paths. While the motion is dictated by a guide wire and motor, the aligning mechanism that orients the Magnetic Delivery Vehicle (MDV), which is attached at the end of the guide wire, is the generation of a specific magnetic field at the MDV. In this manner, a torque is imposed upon the MDV which aligns it in the desired direction. The MNDD provides the software that is responsible for the calculation of the currents that result in the desired magnetic field at the location occupied by the MDV.

1.3 Definition and Acronyms
- A ............... Amps
- EPS ............... Fractional Accuracy
- N ............... Newtons
- mm ............... Millimeters
- T ............... Teslas
- m ............... Meters
- SD ............... Surgeon Display
- FCS ............... Field Computation Software
- FGS ............... Field Generation Software
- FMS ............... Field Matching Software
- MAS ............... Matrix Allocation Software
- MDV ............... Magnetic Delivery Vehicle
- MNIS ............... Magnetic Navigation Interface Software
- MNS ............... Magnetic Navigation Software
- MNDD ............... Magnetic Navigation Software Description
- MSS ............... Magnetic Stereotaxis System
- QOS ............... Quadratic Optimization Software
- RMS ............... Root-Mean-Square
- SDD ............... Software Design Description
- SVD ............... Singular Value Decomposition

2. References
- ANSI/IEEE Std. 1016-1987, *IEEE Recommended Practice for Software Design Descriptions*
- ANSI/IEEE Std. 1016-1993, *IEEE Guide to Software Design Descriptions*
- F. M. Creighton, "Control of Magnetomotive Actuators for an Implanted Object in Brain and Phantom Materials," university of Virginia School of Engineering and Applied Science Technical Report No. UVA/124620/MANE96/102, (May 1996), 184 pp.
- W. H. Press, S. A. Teukolsky, W. T. Vetterling, B. P. Flannery, *Numerical Recipes in C: The Art of Scientific Computing*, ($2^{nd}$ ed.), New York: Cambridge University Press, 1992.

3. Magnetic Navigation Software

3.1 Module Decomposition

The modules pertaining to the MNDD are separated into six files. These consist of the Quadratic Optimization Software (QOS), the Field-Matching Software (FMS), the MagNav Interface Software (MNIS), the Field Computation Software (FCS), the Field Generation Software (FGS), and the Matrix Allocation Software (MAS). Figure 1 depicts the decomposition of the MNDD into the above software components. Standard libraries are excluded in the diagram and arrows denote the direction of the dependency.

Figure 1 Magnetic Navigation Software Dependency

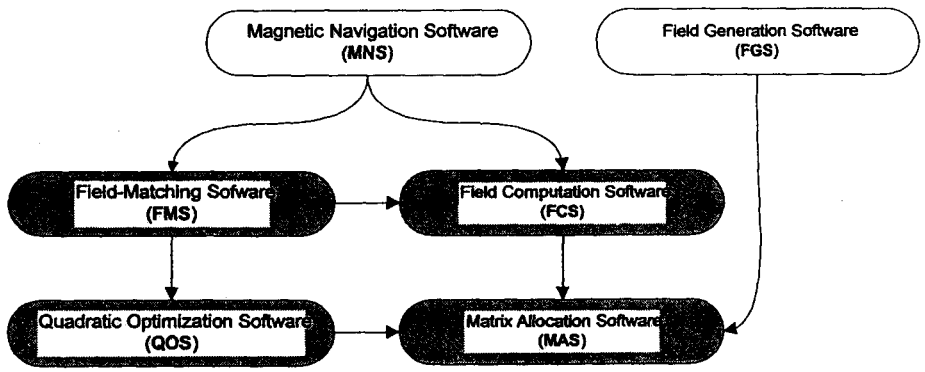

3.1.1 Magnetic Navigation Interface Software

The MNIS (contained in the ANSI C files mag_nav.c and mag_nav.h) serves as an interface between calls from the SD and the FMS. Initialization and deinitialization functions allocate and deallocate, respectively, those arrays that describe the nature of the magnetic field for each superconducting coil. Also, functions that allow the user to change the solution tolerances in the FMS are present in the MNIS.

3.1.2 Field matching Software

The FMS (field_match_v1.c and field_match_v1.h) contains those functions that translate the problem of minimizing the coil-current metric subject to a constraining magnetic field into the proper form for the QOS. Solution tolerances may be changed from their default values (assigned in the FMS) if deemed necessary. These tolerances consist of the maximum field variation, field magnitude variation, and current that the generated solution must not violate in order for a solution to be deemed viable.

3.1.3 Quadratic Optimization Software

The QOS is contained in the C files quad_opt.c and quad_opt.h and consists of those functions that allow for the optimization of a quadratic objective function. Appendix A fully addresses the nature of the quadratic problem and how it pertains to the MSS. Suffice it to say that solutions are generated by minimizing the coil-current metric (sum of the squares of the coil currents) which constitute a quadratic objective function. The requirement of a specific magnetic field imposes three constraints to the six-coil system that constitutes the MSS. Thus, the problem is one of minimizing a quadratic objective function (the coil-current metric) subject to three linear constraints (the field is linear with respect to the current).

3.1.4 Field Computation Software

The functions contained within the FCS are responsible for the calculation of the magnetic field and gradients given the coil arrangement and coil description intrinsic to the MSS apparatus. These functions are contained din the C files field_comp.c and field_comp.h. The theory behind the construction of these files can best be understood by examining chapters 3 and 4 of the dissertation/technical report "Control of Magnetomotive Actuators for an Implanted Object in Brain and Phantom Materials" by F. M. Creighton.

3.1.5 Field Generation Software

The FGS is responsible for creating the data tables required by the FCS. The functions, contained in field_gen.c and field_gen.h, allow magnetic data tables to be created for a magnetic coil with user-specified dimensions. These dimensions include the number of coil windings, thickness, width, integration parameters, etc. as well as the integration parameters which determine the accuracy of the data. A separate function enables the user to locate the coil midplanes of the six MSS superconducting coils with respect to the center of helmet coordinates.

3.1.6 Matrix Allocation Software

One-dimensional and two-dimensional arrays are allocated and deallocated by the functions specified in the MAS (defined in mat_alloc.c and mat_alloc.h). Integer- and floating- point versions are provided for the one-dimensional arrays (termed "vectors"). Two-dimensional floating-point array function are responsible for allocating and deallocating the "matrices".

3.2 Data Description

3.2.1 Magnetic Navigation Interface Software

- MagNavCalcB(): Calculates the magnetic field.
- MagNavCalcF(): Calculates the magnetic force for a permanent MDV.
- MagNavCalcPermF(): Calculates the force for a permeable MDV.
- MagNavDeinit(): Deallocates memory holding field data for coils.
- MagNavFieldMatch(): Calculates the currents that yield the desired magnetic field.
- MagNavInit(): Loads and allocates the magnetic field data for Z coils and X and Y coils.
- MagNavSetFilePath(): Sets a new name and path for the coil array file.
- MagNavSetParam(): Sets the global parameters that determine viability of solution.

3.2.2 Field Matching Software Description

- FieldMatch_v1(): Calculates the currents that yield the desired magnetic field by minimizing the current metric.
- SetMaxBAng(): Sets the maximum magnetic field variation.
- SetMaxBTol(): Sets the maximum fractional magnetic field strength variation.
- SetMaxCurrent(): Sets the maximum current any coil may safely be set to.

3.2.3 Quadratic Optimization Software Description

- CalcSymmetricMatrix(): Replaces input square matrix with symmetric form for quadratic problems.
- LUBackSub(): Back-substitutes the LU decomposed matrix to solve for linear set.
- LUDecomp(): Replaces input square matrix with its LU decomposition.
- LUSolve(): Solves a set of linear equations via LU decomposition.

- func_br(): Internal function denoting the radial magnetic field.
- GenerateFile(): Generates a data table for a coil.
- PolyInt(): Polynomial interpolation function.
- QRomb(): Numerical integration function using Romberg integration.
- SetCoilParam(): Queries all coil parameters.
- SetCurrent(): Queries coil's current.
- SetFuncParam(): Sets internal variables to the input parameters.
- SetInRad(): Queries coil's inner radius.
- SetOutRad(): Queries coil's outer radius.
- SetRombParam(): Sets the internal integration parameters to the input values.
- SetRombEPS(): Queries the EPS parameter for integration function.
- SetRombFilNum(): Queries the filament number for integration function.
- SetRombJMAX(): Queries the JMAX parameter for integration function.
- SetRombK(): Queries the K parameter for integration function.
- SetRombMaxIts(): Queries the maximum iterations for integration function.
- SetThickness(): Queries coil's thickness.
- SetTurns(): Queries coil's windings.
- ShowCoilParam(): Displays coil information for FieldGenExe().
- ShowMenu(): Displays menu for FieldGenExe().
- NthTrapStage(): Calculates nth stage of trapezoidal rule.
- Version(): Displays the version of the FGS.

3.2.6 Matrix Allocation Software Description
- fmatrix(): Allocates a float matrix.
- free_fmatrix(): Deallocates a float matrix.
- free_fvector(): Deallocates a float vector.
- free_ivector(): Deallocates an integer vector.
- fvector(): Allocates a float vector.
- ivector(): Allocates an integer vector.
- MatAllocErStatus(): Returns an error flag if there was an allocation error.

4. Public Software: MagNav Interface Software

The MNIS is the topmost file in the hierarchy that is solely responsible in communicating with the SD. All other files that constitute the MNS serve as support to the MNIS. It is important that the magnetic field tables for the MSS coils be loaded and allocated for any function that involves calculation of the magnetic field or any of its derivatives. These cases are noted in the interface description.

4.1 MNIS Description and Interface

In the interface tables that follow, the nature of each function call is detailed. In addition to the full interface, descriptions are provided for the input and output variables as well as those variables whose value change as the result of the function call.

4.1.1 MagNavCalcB()

This function is responsible for the calculation of the magnetic field given a position within the volume established by the data files and given a set of currents. If the position is outside the data-table range, an error status be returned. Note that MagNavInit() must be called prior to this function.

| Interface | int MagNavCalcB( float px, float py, float pz, float MN_I[], float *Bi, float *Bj, float *Bk ) | |
|---|---|---|
| Type | Variable | Data Description |
| Input | px | Position along x-axis (mm). |
| | py | Position along y-axis (mm). |
| | pz | Position along z-axis (mm). |
| | MN_I | Array containing currents (A) for the six coils allocated according to [0..5]. An enumeration is provided in the header for identification of the current elements.<br><br>X_NEG = XB = 0    X_POS = XA = 1<br>Y_NEG = YB = 2    Y_POS = YA = 3<br>Z_NEG = ZB = 4    Z_POS = ZA = 5 |
| Output | Bi | The $i^{th}$ component of the field (T). |
| | Bj | The $j^{th}$ component of the field (T). |
| | Bk | The $k^{th}$ component of the field (T). |
| Modified | (None) | |
| Return | Returns status code according to<br><br>_MN_BadInput:    A parameter was improperly entered.<br>_MN_PASS:    No error occurred.<br>_MN_FAIL:    Lower level error occurred in the field computations. | |

4.1.2 MagNavCalcF()

This function is responsible for the calculation of the magnetic force for a small permanent magnet given a position within the volume defined by the data files, a magnetic moment, and a set of currents. Only if the position is outside the data-table range or if a magnetic moment smaller than the floating point limit is entered will an error status be returned. Note that MagNavInit() must be called prior to this function.

| Interface | int MagNavCalcF( float px, float py, float pz, float MN_I[], float moment, float *Fi, float *Fj, float *Fk ) | |
|---|---|---|
| Type | Variable | Data Description |
| Input | px | Position along x-axis (mm). |
| | py | Position along y-axis (mm). |
| | pz | Position along z-axis (mm). |
| | MN_I | Array containing currents (A) for the six coils allocated according to [0..5]. An enumeration is provided in the header for identification of the current elements.<br><br>X_NEG = XB = 0    X_POS = XA = 1<br>Y_NEG = YB = 2    Y_POS = YA = 3<br>Z_NEG = ZB = 4    Z_POS = ZA = 5 |
| | moment | The magnetic moment in $A \cdot m^2$. Must be greater than 0. |
| Output | Fi | The $i^{th}$ component of the force (N). |
| | Fj | The $j^{th}$ component of the force (N). |
| | Fk | The $k^{th}$ component of the force (N). |
| Modified | (None) | |
| Return | Returns status code according to<br><br>_MN_BadInput:    A parameter was improperly entered.<br>_MN_PASS:    No error occurred.<br>_MN_FAIL:    Lower level error occurred in the field computations. | |

4.1.3 MagNavCalcPermF()

This function is responsible for the calculation of the magnetic force for a small permeable magnet given a position within the volume defined by the data files, a magnetic moment, and a set of currents. Only if the position is outside the data-table range or if a magnetic moment smaller than the floating point limit is entered will an error status be returned. Note that MagNavInit() must be called prior to this function.

| Interface | int MagNavCalcPermF( float px, float py, float pz, float MN_I[], float m_sat, float B_sat, float *Fi, float *Fj, float *Fk ) | |
|---|---|---|
| Type | Variable | Data Description |
| Input | px | Position along x-axis (mm). |
| | py | Position along y-axis (mm). |
| | pz | Position along z-axis (mm). |
| | MN_I | Array containing currents (A) for the six coils allocated according to [0..5]. An enumeration is provided in the header for identification of the current elements.<br><br>X_NEG = XB = 0    X_POS = XA = 1<br>Y_NEG = YB = 2    Y_POS = YA = 3<br>Z_NEG = ZB = 4    Z_POS = ZA = 5 |
| | m_sat | The magnetic moment ($A \cdot m^2$) at saturation. Must be greater than 0. |

| | B_sat | The saturation magnetic field (T). Must be greater than 0. |
|---|---|---|
| Output | Fi | The i$^{th}$ component of the force (N). |
| | Fj | The j$^{th}$ component of the force (N). |
| | Fk | The k$^{th}$ component of the force (N). |
| Modified | (None) | |
| Return | Returns status code according to<br><br>_MN_BadInput:    A parameter was improperly entered.<br>_MN_PASS:    No error occurred.<br>_MN_FAIL:    Lower level error occurred in the field computations. | |

4.1.4 MagNavDeinit()

Deinitializes the matrices holding the field information for each coil. This routine should be called at the termination of the MNS to recover allocated memory. Prior to executing this function, MagNavInit() should be called when the MNS is loaded, though no error results if this is not done.

| Interface | void MagNavDeinit( void ) | |
|---|---|---|
| Type | Variable | Data Description |
| Input | (None) | |
| Output | (None) | |
| Modified | (None) | |
| Return | (No return) | |

4.1.5 MagNavFieldMatch()

This function is responsible for computing the currents that yield the desired field orientation and field strength. The specified orientation need not be normalized to any particular value so long as the entered values are not less that the floating point limit. Likewise, there must be a nonzero field strength and the position must be located within the scope of the data files. If these conditions are not satisfied, an error status is returned. Note that MagNavInit() must be called prior to this function.

| Interface | int MagNavFieldMatch( float px, float py, float pz, float *dx, float *dy, float *dz, float Bmag, float MN_I[], int mode ) | |
|---|---|---|
| Type | Variable | Data Description |
| Input | px | Position along x-axis (mm). |
| | py | Position along y-axis (mm). |
| | pz | Position along z-axis (mm). |
| | Bmag | Field strength (T). |
| | mode | If the MDV is to be oriented antiparallel to the field, then *mode* is set equal to the macro B_ANTI_ALIGNED. Otherwise, the MDV is oriented parallel to the field and *mode* is set to the macro B_ALIGNED. |
| Output | MN_I | Array containing currents (A) for the six coils allocated according to [0..5]. An enumeration is provided in the header common.h for identification of the |

|  |  | current elements. These are assigned according to<br><br>X_NEG = XB = 0    X_POS = XA = 1<br>Y_NEG = YB = 2    Y_POS = YA = 3<br>Z_NEG = ZB = 4    Z_POS = ZA = 5 |
|---|---|---|
| Modified | dx | Inputted as the desired orientation's x- component. Outputted as resulting orientation's x- component. |
|  | dy | Inputted as the desired orientation's y- component. Outputted as resulting orientation's y- component. |
|  | dz | Inputted as the desired orientation's z- component. Outputted as resulting orientation's z- component. |
| Return | A status code is returned as one of the following:<br><br>_MN_BadInput:    A parameter was improperly entered.<br>_MN_BError:    Solution generates a field strength outside the tolerance associated with the desired field.<br>_MN_FAIL:    An error occurred in a call to an external function.<br>_MN_IMaxError:    Solution generates a current element that is greater in magnitude than the maximum allowable current.<br>_MN_InitError:    MagNav data tables not initialized.<br>_MN_PASS:    No error occurred. | |

4.1.6 MagNavInit()

Initializes the matrices holding the field information for each coil. This routine should be called at the initialization of the MNS to properly allocate the field data for the coils. An error status is returned if there is insufficient resources for the allocation or if the data files containing the field information could not be loaded.

| Interface | *int MagNavInit( int display_flag )* | |
|---|---|---|
| Type | Variable | Data Description |
| Input | display_flag | Flag as to whether or not the header to the data files and the splines should be streamed to the standard error device. This flag must be set according to the following macros:<br><br>MN_SHOW_INFO    Header information displayed.<br>MN_HIDE_INFO    Header information not displayed. |
| Output | (None) | |
| Modified | (None) | |
| Return | Returns status code according to<br><br>_MN_FAIL:    A lower level error occurred pertaining to matrix allocation or to the loading of the data files.<br>_MN_PASS:    No error occurred. | |

4.1.7 MagNavSetFilePath()

Sets the file path of the text file (coil_array.txt) that contains the location of the six coils (in helmet coordinates) of the MSS helmet cryostat in addition to the names of the files which contain the magnetic field informatio for the X and Y coils and the Z coils.

| Interface | void MagNavSetFilePath( char path[] ) | |
|---|---|---|
| Type | Variable | Data Description |
| Input | path | The path of the file that contains the coil locations in helmet coordinates. The string must end with the directory separator "/". |
| Output | (None) | |
| Modified | (None) | |
| Return | (No return) | |

4.1.8 MagNavSetParam()

The parameters that establish the field strength variation and field angle (with respect to the desired field strength and orientation, respectively) and the maximum current are set from their default values in this function.

| Interface | int MagNavSetParam( mag_nav_param value ) | |
|---|---|---|
| Type | Variable | Data Description |
| Input | value | A structure to the parameters that set the maximum current, field strength, and field angle. |
| Output | (None) | |
| Modified | (None) | |
| Return | Returns status code according to<br><br>_MN_BadInput:   A parameter was improperly entered.<br>_MN_PASS:       No error occurred. | |

4.1.9 MNIS Structures

4.1.9.1 MNIS Public Structures 4.1.9.1.1 mag_nav_param
This structure stores the tolerances associated with the solutions generated by the function MagNavFieldMatch(). The elements are as follows:

| Element | Data Type | Definition |
|---|---|---|
| MaxAngDev | float | The maximum angular deviation between the desired magnetic field orientation and the computed field orientation. This value is in degrees. |
| MaxCurrent | float | The maximum magnitude current (A) any coil may achieve. |
| BMagTol | float | The fractional field tolerance allowed in the generated magnetic field strength as compared to the desired field strength. For example, if the fractional tolerance is $f$ = BMagTol, then the lower and upper limits to the generated field are $B(1-f)$ and $B(1+f)$, respectively. |

4.1.10 MNIS Enumerations

4.1.10.1 MNIS Public Enumerations 4.1.10.1.1 mag_nav_error_codes
Below are listed all status codes that denote the errors that can occur for the functions of the MNIS.

| Enumeration | Value | Description |
|---|---|---|
| _MN_PASS | 1 | No error occurred. |
| _MN_FAIL | 0 | A lower level error occurred. |
| _MN_BadInput | -1 | A parameter was improperly entered. |
| _MN_IMaxError | -2 | Solution generates a current element that is greater in magnitude than the maximum allowable current. |
| _MN_BError | -3 | Solution generates a field strength outside the tolerance associated with the desired field. |

4.1.11 MNIS Macros and Definitions

4.1.11.1 MNIS Public Definitions
The following definitions are defined in the MNIS:

| Definition | Value | Description |
|---|---|---|
| B_ANTI_ALIGNED | 1 | Denotes that MDV is to be antialigned with the magnetic field. |
| B_ALIGNED | 0 | Denotes that MDV is to be aligned with the magnetic field. |
| MN_SHOW_INFO | 1 | Show headers to data tables when loaded. |
| MN_HIDE_INFO | 0 | Do not show headers to data tables when loaded. |

4.2 MNIS Decomposition and Detailed Design

The decomposition and detailed description that follows is written in a form that best conveys the nature of the ANSI C programming language in which the MNS was written. The decomposition is carried out so that functions that are not part of the parent file are shaded. In these cases, the file is noted to the right. Standard libraries are not included in the decomposition.

4.2.1 MagNavCalcB()

Calculates the magnetic field from a set of currents and the MDV's location. If unable to complete the operation or if the input parameters are outside the scope of the module, an error flag is returned.

Figure 2 MagNavCalcB() Subordinates

Figure 3:
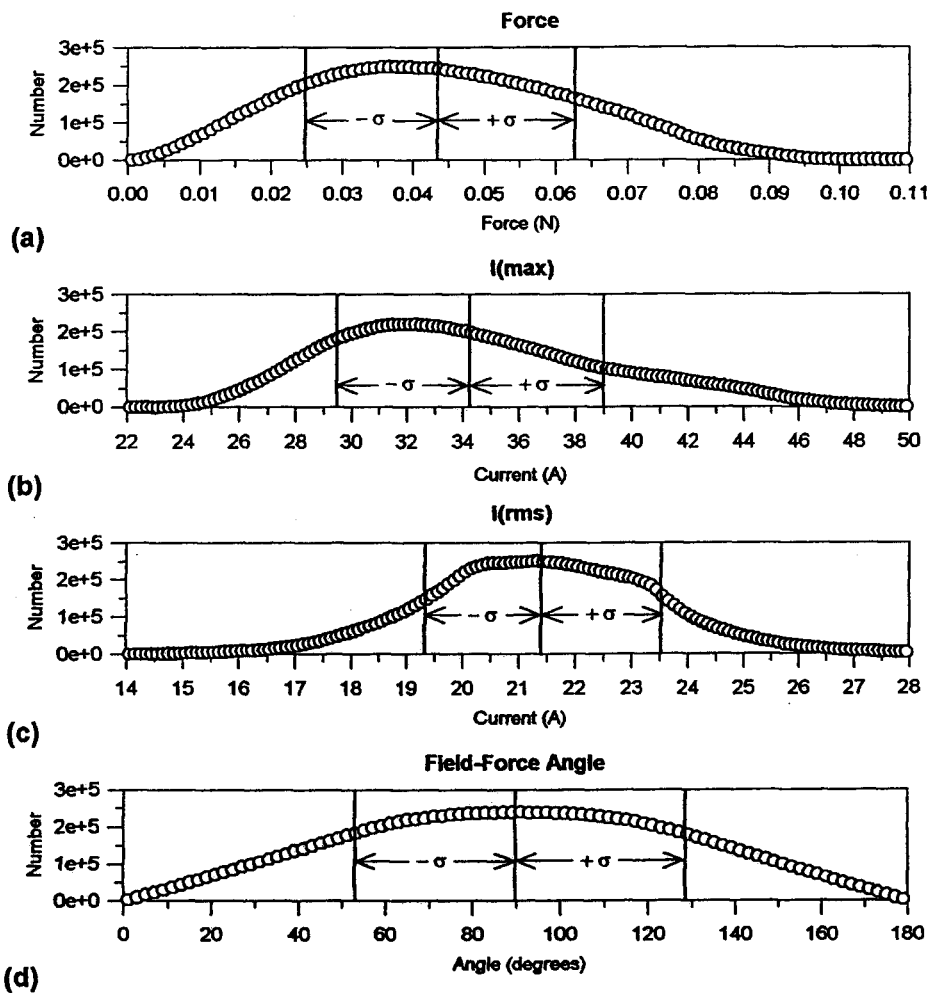

Figure 3 Error Decomposition of MagNavCalcB()

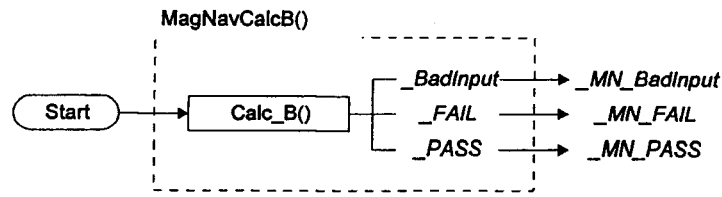

4.2.2 MagNavCalcF()

Calculates the magnetic force generated on a permanent magnetic moment from a set of currents, the magnetic moment, and the MDV's location. If unable to complete the operation or if the input parameters are outside the scope of the module, an error flag is returned.

Figure 4 MagNavCalcF() Subordinates

Figure 5 Error Decomposition of MagNavCalcF()

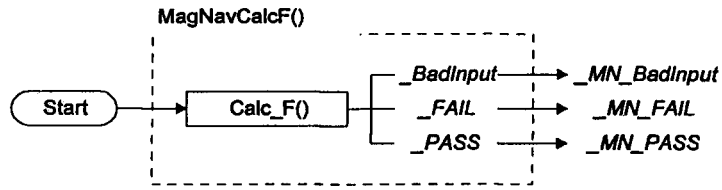

4.2.3 MagNavCalcPermF()

Calculates the magnetic force generated on a permeable MDV from a set of currents, the saturated moment, the saturation magnetic field, and the MDV's location. If unable to complete the operation or if the input parameters are outside the scope of the module, an error flag is returned.

Figure 6 MagNavCalcPermF() Subordinates

Figure 7 Error Decomposition of MagNavCalcPermF()

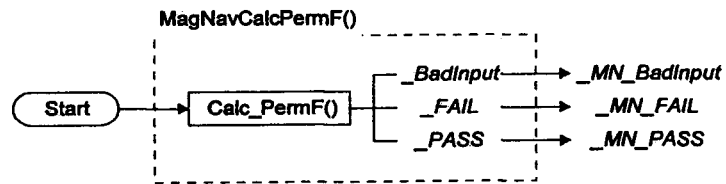

4.2.4 MagNavDeinit()

This function is responsible for loading the data tables for the two coil types and allocating the memory for the spline interpolation. While no error will occur, it is assumed that the function MagNavInit() has already been called. However, if this is not the case, then there is no memory to deallocate and nothing is done.

Figure 8 MagNavDeinit() Subordinates

4.2.5 MagNavFieldMatch()

This function converts an orientation vector and field strength into a specific magnetic field orientation at the MDV. There are two modes of operation. The first is the "parallel" case in which the MDV's magnetic moment is to be orientated in the same direction as the push line. The second case is the "anti-parallel" case in which the MDV's moment is oriented 180° from the forward direction of guide line motion. On return, either an error flag or an acceptable solution (which will be within the specified tolerances) is passed. The input orientation is modified to reflect the actual final orientation. In almost all cases, this orientation is the same; however, it is critical that the operator be informed of the actual final projected orientation, even though the solution is within the acceptable tolerances. In the pseudo code detailed in Fig. 4, the EPS value (i.e., the fractional accuracy) is set at 1.0e-6.

Figure 9 MagNavFieldMatch() Subordinates

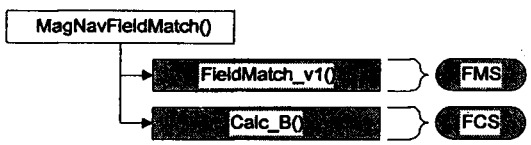

Figure 10 Error Decomposition of MagNavFieldMatch()

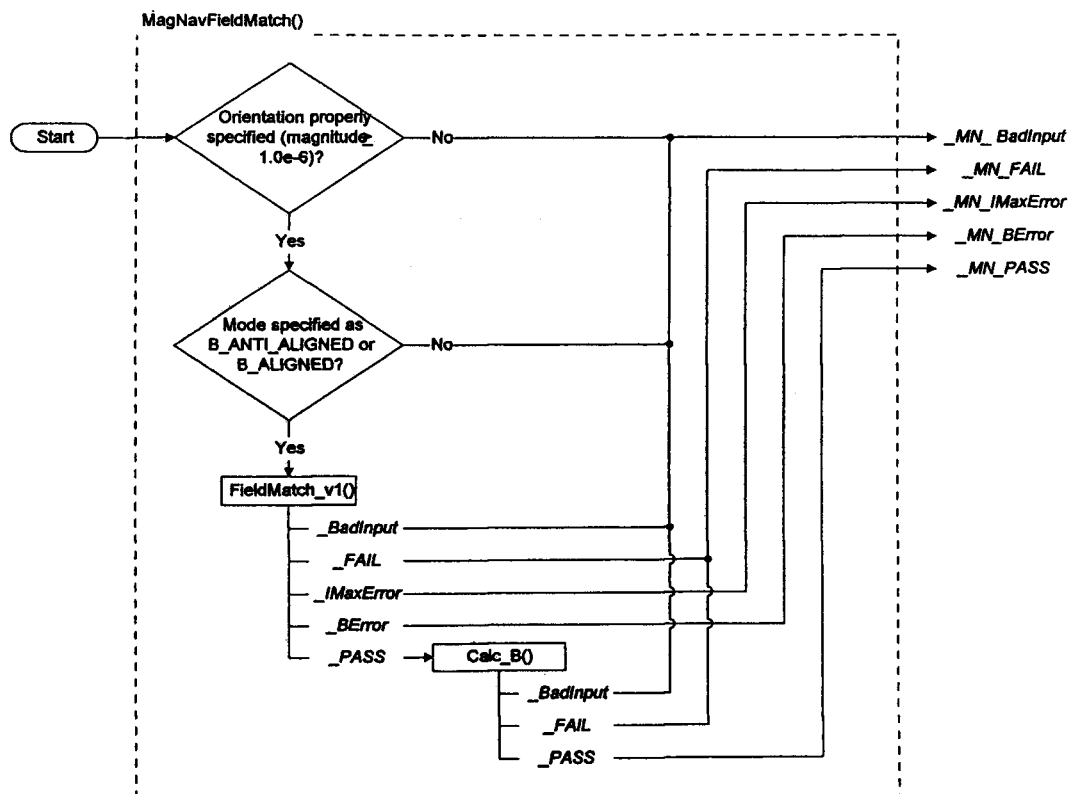

4.2.6 MagNavInit()

This function is transparent with respect to the subordinate function InitArrays() which is located in the FCS. The display flag passed through the function call results in the headers being streamed to the standard output device as well as status comments to the spline calculations being streamed. It is important that this function be called prior to any function that results in magnetic field calculations. These functions are noted in the interface description.

Figure 11 MagNavInit() Subordinates

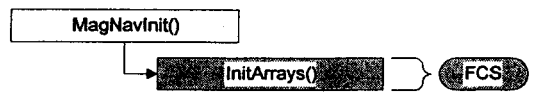

Figure 12 Error Decomposition of MagNavInit()

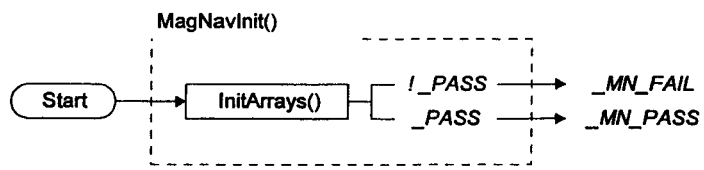

4.2.7 MagNavSetFilePath()

Sets the path of the file containing the locations of the six coils comprising the helmet cryostat and the names and locations of the data files for the X and Y coils and the Z coils. Without specification, this file is assumed to be located in the default directory and defined in the FCS header as DEF_COIL_ARRAY_PATH.

Figure 13 MagNavSetFilePath() Subordinates

4.2.8 MagNavSetParam()

Allows the specification of the parameter tolerances that deem a solution as being viable. A structure possessing the tolerances is passed in when called. The elements that may be changed consists of (1) the maximum angle discrepancy between the desired magnetic field and the generated magnetic field, (2) the maximum fractional difference between the desired field strength and the generated field strength, and (3) the maximum allowable current magnitude that any coil may safely achieve. These tolerances take on the following default values (defined in the FMS header file):

| Element | Default Value |
|---|---|
| MaxAngDev | DEF_MAX_ANG_DEV |
| MaxCurrent | DEF_MAX_CURRENT |
| BMagTol | DEF_BMAG_TOL |

Figure 14 MagNavSetParam() Subordinates
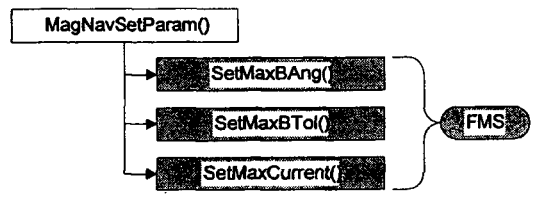
Figure 15 Error Decomposition of MagNavSetParam()

5. Private Software: Support Software

The files that follow serve as support to the MNIS. None of the functions listed need ever be called in the public scope. These files consist of the FMS, FCS, QOS, and the MAS.

5.1 Description and Interface

This document is organized in a fashion that best reflects the fact that those functions intrinsic to magnetic navigation are coded in the ANSI C programming language. The design is best understood from data charts and structured flow diagrams. The functions associated with each module are detailed below. In each case, the function is identified and its purpose stated as well as the input, output, and modified variables to each function.

*5.1.1 Field Matching Software Description*

The FMS consist of those functions that translate the magnetic problem of minimizing the currents subject to the generation of a desired magnetic field into a quadratic problem subject to linear constraints. The solutions to the currents are the result of minimizing the current metric (i.e., the RMS current) and represent an unbounded solution. That is to say, the upper limit to the current magnitudes are not explicitly considered in the solution. However, such limits do determine if a generated solution is viable for the MSS.

5.1.1.1 FieldMatch_v1()

This function is responsible for calculating the currents that generate the specified magnetic field. An error is returned if the position is outside the scope of the tabulated region of the helmet cryostat. An array to the currents are returned on exit. If any current is greater than the maximum tolerable value, an error flag is returned with the currents.

| Interface | int FieldMatch_v1( coord_3d p, vec_3d BCall, float I[] ) | |
|---|---|---|
| Type | Variable | Data Description |
| *Input* | p | Position structure (m). |
| | BCall | Structure holding desired magnetic field (T). |
| *Output* | I | Array containing currents (A) for the six coils allocated according to [1..6]. An enumeration is provided in the header field_comp.h for easy identification of the current elements.<br><br>XPOS = 1  XNEG = 2<br>YPOS = 3  YNEG = 4<br>ZPOS = 5  ZNEG = 6 |
| *Modified* | *(None)* | |
| *Return* | Returns status code according to | |
| | _BadInput: | A parameter was improperly entered. |
| | _PASS: | No error occurred. |
| | _FAIL: | Lower level error occurred in the field computations. |
| | _IMaxError: | Maximum current violated in solution. |
| | _BError: | Solution's magnetic field outside tolerances. |

5.1.1.2 SetMaxBAng()

Changes the maximum angular variation between the desired and generated magnetic field orientation from the default value DEF_MAX_ANG_DEV (defined in FMS header) to the user specified value (set in degrees). An error is returned is the specified angle is less than 0° or greater than 180°.

| Interface | int SetMaxBAng( float angle ) | |
|---|---|---|
| Type | Variable | Data Description |
| Input | angle | Maximum field variation angle (degrees). |
| Output | (None) | |
| Modified | (None) | |
| Return | Returns status code according to<br><br>_BadInput:          The angle was improperly entered.<br>_PASS:               No error occurred. | |

5.1.1.3 SetMaxBTol()

Changes the maximum fractional variation between the desired and generated magnetic field strength from the default value DEF_BMAG_TOL (defined in FMS header) to the user specified value. An error is returned is the specified angle is less than the EPS value of FLT_EPSILON (defined in float.h).

| Interface | int SetMaxBTol( float tol ) | |
|---|---|---|
| Type | Variable | Data Description |
| Input | tol | Maximum fractional difference allowed in generated field strength from desired field magnitude. |
| Output | (None) | |
| Modified | (None) | |
| Return | Returns status code according to<br><br>_BadInput:          The fractional tolerance was improperly entered.<br>_PASS:               No error occurred. | |

5.1.1.4 SetMaxCurrent()

Sets the maximum current magnitude that any coil may safely be set. This value is in amps. An error will be returned if the magnitude is set less than _IMIN_EPS (private definition in FMS).

| Interface | int SetMaxCurrent( float Imax ) | |
|---|---|---|
| Type | Variable | Data Description |
| Input | Imax | Maximum magnitude current on a coil (A). |
| Output | (None) | |
| Modified | (None) | |
| Return | Returns status code according to<br><br>_BadInput:          The current was improperly entered.<br>_PASS:               No error occurred. | |

5.1.1.5 FMS Enumerations 5.1.1.5.1 FMS Public Enumerations

*5.1.1.5.1.1 field_match_error_codes*

Below are listed all status codes that denote the errors that can occur for the functions of the FMS.

| Enumeration | Value | Description |
|---|---|---|
| _IMaxError | -2 | Solution generates a current element that is greater in magnitude than the maximum allowable current. |
| _BError | -3 | Solution generates a field strength outside the tolerance associated with the desired field. |

5.1.1.6 FMS Macros and Definitions 5.1.1.6.1 FMS Public Definitions

The following definitions are defined in the MNIS:

| Definition | Value | Description |
|---|---|---|
| DEF_MAX_ANG_DEV | 5.0 | Maximum allowed angle between desired and generated magnetic field such that a solution may be deemed viable. |
| DEF_MAX_CURRENT | 60.0 | Maximum allowed current magnitude such that a solution may be deemed viable. |
| DEF_BMAG_TOL | 0.05 | Maximum allowed fractional field strength variation such that a solution may be deemed viable. |

5.1.2 Quadratic Optimization Software Description

The QOS consist of those functions that allow for solutions to be found for equality constrained, multi-variable quadratic objective functions. Both files comprising the QOS, *quad_opt_v1.c* and *quad_opt_v1.h*, are written in ANSI C. Two methods are used for solving the resulting set of linear equations that correspond to the critical points of the quadratic object function. These being LU decomposition and singular value decomposition (SVD). While the former rarely fails, it is theoretically possible that in certain circumstances the square matrix made up of the linear equations is not invertible. In these cases, SVD is useful in finding the "best" nearby solution.

5.1.2.1 CalcSymmetricMatrix()

Converts a matrix allocated according to $A[1..n][1..n]$ to its symmetric form. Note that $n$ must be greater than 1.

| Interface | int CalcSymmetricMatrix( float **A, int n ) | |
|---|---|---|
| Type | Variable | Data Description |
| Input | n | Size of the matrix $A[1..n][1..n]$. $n$ must be greater than or equal to 1. |
| Output | (None) | |
| Modified | A | Entered as the matrix to be converted to its symmetric form. Returned in its symmetric form. |
| Return | Returns status code according to<br><br>_BadInput: The input parameters were not properly set.<br>_PASS: No error occurred. | |

5.1.2.2 ImproveLinSoln()

Iteratively improves the solution to a set of linear equations by examining the LU decomposition of $A x = b$ (defined by *LUA*). (See *Press, et al.*)

| Interface | int ImproveLinSoln( float **A, float **ALU, float *x, int n, int indx[], float b[] ) | |
|---|---|---|
| Type | Variable | Data Description |
| Input | A | The square matrix $A$ consist of those equations that comprise a linear set. $A$ must be allocated according to $A[1..n][1..n]$. |
| | LUA | The LU decomposition of a linear set of equations. $A$ must be a square matrix so that $A$ is allocated according to $A[1..n][1..n]$. |
| | n | The dimensionality of the problem. This value must be greater than 1. |
| | indx | The row permutation index associated with the LU decomposed matrix A where *indx* is allocated according to $indx[1..n]$. |
| | b | The constant column matrix. $b$ is allocated according to $b[1..n]$. |
| Output | x | The iteratively improved solution to the set of linear equations. |
| Modified | (None) | |
| Return | Returns status code according to<br><br>_BadInput: The input parameters were not properly set. | |

| | _PASS: | No error occurred. |
|---|---|---|
| | _FAIL: | Memory allocation error. |

5.1.2.3 LUBackSub()

LU back substitution allows for a solution to a square matrix to be found. The LU decomposition, LUDecomp(), must occur prior to calling this function. The decomposition is passed in through the $A$ matrix, the row permuations through $indx$ and the constant column matrix through $b$ (see *Press, et al.*).

| Interface | int LUBackSub( float **A, int n, int indx[], float b[] ) | |
|---|---|---|
| Type | Variable | Data Description |
| *Input* | $A$ | The LU decomposition of a linear set of equations. $A$ must be a square matrix so that $A$ is allocated according to $A[1..n][1..n]$. |
| | $n$ | The dimensionality of the problem. This value must be greater than 1. |
| | $indx$ | The row permutation index associated with the LU decomposed matrix A where $indx$ is allocated according to $indx[1..n]$. |
| *Output* | (None) | |
| *Modified* | $b$ | Passed in as the constant column matrix, returned as the solution to the linear set of equations. $b$ is allocated according to $b[1..n]$. |
| *Return* | Returns status code according to | |
| | _BadInput: | The dimension of the problem was improperly entered. |
| | _PASS: | No error occurred. |

5.1.2.4 LUDecomp()

Replaces a square matrix with its LU decomposition. An error flag will be returned if there is an allocation error or bad input, or if it is found that the entered square matrix possesses a singularity as a row of zeroes. In this case, SVD should be used (see *Press, et al.*).

| Interface | int LUDecomp( float **A, int n, int indx[], float *d ) | |
|---|---|---|
| Type | Variable | Data Description |
| *Input* | $n$ | The dimensionality of the problem. This value must be greater than 1. |
| *Output* | $indx$ | The row permutation index associated with the LU decomposed matrix A where $indx$ is allocated according to $indx[1..n]$. |
| | $d$ | Flag to denote even or odd row permutations. |
| *Modified* | $A$ | On input, the square matrix $A$ consist of those equations that comprise a linear set. On return, $A$ is replaced by its LU decomposition. $A$ must be allocated according to $A[1..n][1..n]$. |
| *Return* | Returns status code according to | |
| | _BadInput: | The dimension of the problem was improperly entered. |
| | _PASS: | No error occurred. |

5.1.2.5 LUSolve()

Solves a set of linear equation via LU decomposition. The system of equations must comprise an exactly specified set (i.e., not over- or under-constrained). The input parameters are entered according to $\mathbf{A}\,\mathbf{x} = \mathbf{b}$ with the solution given by $\mathbf{x} = \mathbf{A}^{-1}\,\mathbf{b}$. The inversion of the matrix A is done through LU decomposition. If a near singularity exists nearby in the $n$-dimensional space, then the solution may not be useful.

| Interface | *int LUSolve( float \*\*A, float \*b, float \*x, int n )* | |
|---|---|---|
| Type | Variable | Data Description |
| *Input* | *A* | Square matrix consisting of the specified linear set of equations. |
| | *b* | Constants matrix as detailed above. |
| | *n* | Dimensionality of problem. *n* must be greater than 1. |
| *Output* | *x* | *n*-dimensional solution vector. |
| *Modified* | *(None)* | |
| *Return* | Returns status code according to <br><br> _BadInput:    The dimension of the problem was improperly entered. <br> _PASS:    No error occurred. <br> _FAIL:    Memory allocation error. | |

5.1.2.6 Mat_X_Vec()

Multiplies the column matrix (i.e., vector) $b[1..br]$ by the matrix $A[1..ar][1..ac]$, yielding the matrix $c[1..ar]$ (i.e., $\mathbf{c} = \mathbf{A}\,\mathbf{b}$).

| Interface | *int Mat_X_Vec( float \*\*A, float b[], int ar, int ac, int br, float c[] )* | |
|---|---|---|
| Type | Variable | Data Description |
| *Input* | *A* | Multiplying matrix (see above). |
| | *b* | Multiplying vector (see above). |
| | *ar* | Rows of *A*. *ar* must be greater than 0. |
| | *ac* | Columns of *A*. *ac* must be greater than 0. |
| | *br* | Rows of *b*. *br* must be equal to *ac*. |
| *Output* | *c* | Resulting vector. |
| *Modified* | *(None)* | |
| *Return* | Returns status code according to <br><br> _BadInput:    *ar, ac, br* and/or *ac* were improperly entered. <br> _PASS:    No error occurred. | |

5.1.2.7 MaxQuad_wrt_EqCon()

Maximizes the $n$-dimensional quadratic problem $z = \mathbf{c}^T\mathbf{x} + \mathbf{x}^T\mathbf{P}\mathbf{x}$ subject to $m$ equality constraints of the form $\mathbf{D}\,\mathbf{x} = \mathbf{e}$ and then solves for $\mathbf{x}$.

| Interface | *int MaxQuad_wrt_EqCon( float \*c, float \*\*P, float \*\*D, float \*e, float \*x,* |
|---|---|

|   | | *int n, int m )* |
|---|---|---|
| Type | Variable | Data Description |
| Input | c | Linear components of the objective function which are allocated according to c[1..n]. |
|  | D | m linear equality constraints imposed on the objective function where D is allocated according to D[1..m][1..n]. |
|  | e | m-element constant matrix for the linear constraints. e is allocated according to e[1..m]. |
|  | n | Dimensionality of the problem. n must be greater than 1. |
|  | m | Number of linear constraints. m must be greater than 0 and less than or equal to n. |
| Output | x | The n-dimensional solution vector allocated according to x[1..n]. |
| Modified | P | Quadratic components of the objective function which are allocated according to P[1..n][1..n]. |
| Return | Returns status code according to<br><br>_BadInput:  Either n and/or m were improperly entered.<br>_FAIL:  Lower level error occurred.<br>_PASS:  No error occurred. | |

5.1.2.8 SolveForLinearSet()

Solves a set of linear equations.

| Interface | *int SolveForLinearSet( float \*\*A, float \*b, float \*x, int n )* |
|---|---|
| Type | Variable | Data Description |
|---|---|---|
| Input | A | The square matrix consisting of the linear equations to be reduced. A is allocated according to A[1..n][1..n]. |
|  | b | The constant matrix to the linear problem (see above). b is allocated according to b[1..n]. |
|  | n | Dimensionality of the problem. n must be greater than 1. |
| Output | x | The n-dimensional solution vector allocated according to x[1..n]. |
| Modified | (None) | |
| Return | Returns status code according to<br><br>_BadInput:  n was improperly entered.<br>_FAIL:  Lower level error occurred.<br>_PASS:  No error occurred. | |

5.1.2.9 SVD_BackSub()

Single value decomposition back substitution routine that solves a set of linear equations after the decomposition has been executed. SVDecomp() must be called prior to this function (see *Press, et al.*).

| Interface | *int SVD_BackSub( float \*\*U, float w[], float \*\*v, int m, int n, float b[], float x[] )* |
|---|---|

| Type | Variable | Data Description |
|---|---|---|
| Input | U | U matrix of the SVD where U is allocated according to $U[1..m][1..n]$. |
| | w | Diagonal components of the $w[1..n]$ matrix of the SVD. |
| | v | v matrix of the SVD where v is allocated according to $v[1..n][1..n]$. |
| | m | Number of equations. m must be greater than 0. |
| | n | Number of variables. n must be greater than 1. |
| | b | Constant column matrix where b allocated according to $b[1..m]$. |
| Output | x | Solution column matrix where x allocated according to $x[1..n]$. |
| Modified | (None) | |
| Return | Returns status code according to<br><br>_BadInput: m or n was improperly entered.<br>_FAIL: Lower level error occurred.<br>_PASS: No error occurred. | |

5.1.2.10 SVD_Solution()

Solves a set of linear equation via SVD. The system of equations may be over- or under-constrained since SVD tends to return the "best" solution by least-squares.

| Interface | int SVD_Solution( float **A, int m, int n, float *b, float *x ) | |
|---|---|---|
| Type | Variable | Data Description |
| Input | A | Square matrix consisting of the specified linear set of equations. |
| | m | Number of linear equations. m must be greater than 0. |
| | n | Dimensionality of problem. n must be greater than 1. |
| | b | Constants matrix as detailed above. |
| Output | x | n-dimensional solution vector. |
| Modified | (None) | |
| Return | Returns status code according to<br><br>_BadInput: m or n was improperly entered.<br>_FAIL: Lower level error occurred.<br>_PASS: No error occurred. | |

5.1.2.11 SVDecomp()

Reduces a set of linear equations into their single value decomposition (see *Press, et al.*).

| Interface | int SVDecomp( float **A, int m, int n, float w[], float **v ) | |
|---|---|---|
| Type | Variable | Data Description |
| Input | m | Number of linear equations. m must be greater than 0. |
| | n | Dimensionality of problem. n must be greater than 1. |
| Output | w | Diagonal components of the $w[1..n]$ matrix of the SVD. |

| | $v$ | $v$ matrix of the SVD where $v$ is allocated according to $v[1..n][1..n]$. |
|---|---|---|
| Modified | $A$ | On input, the square matrix $A$ consist of those equations that comprise a linear set. On return, $A$ is replaced by $U$ from the SVD. $A$ must be allocated according to $A[1..m][1..n]$. |
| Return | Returns status code according to<br><br>_BadInput:    $m$ or $n$ was improperly entered.<br>_FAIL:    Lower level error occurred.<br>_PASS:    No error occurred. | |

5.1.2.12 SVZero()

Zeros the elements of the $w[1..n]$ column matrix for the single value back substitution (see *Press, et al.*).

| Interface | int SVZero( float w[], int n ) | |
|---|---|---|
| Type | Variable | Data Description |
| Input | $n$ | Dimensionality of problem. $n$ must be greater than 1. |
| Output | (None) | |
| Modified | $w$ | Diagonal components of the $w[1..n]$ matrix of the SVD. |
| Return | Returns status code according to<br><br>_BadInput:    $n$ was improperly entered.<br>_PASS:    No error occurred. | |

5.1.2.13 TwoPointNorm()

Computes the norm of two numbers without destructive underflow or overflow.

| Interface | float TwoPointNorm( float a, float b ) | |
|---|---|---|
| Type | Variable | Data Description |
| Input | $a$ | First input number. |
| | $b$ | Second input number. |
| Output | (None) | |
| Modified | (None) | |
| Return | Returns the norm of the numbers $a$ and $b$, $\sqrt{a^2+b^2}$. | |

5.1.2.14 QOS Macros and Definitions

5.1.2.14.1 QOS Private Macros

| Macro | Description |
|---|---|
| FMAX( a, b ) | Returns the larger of $a$ and $b$. Typecasts the result as a float. |
| IMIN( a, b ) | Returns the smaller of $a$ and $b$. Typecasts the result as an integer. |
| ISGN( a ) | Returns the sign of a number as an integer. |

| | |
|---|---|
| *SIGN( a, b )* | If $b \geq 0$, then returns $|a|$. Otherwise returns $-|a|$. |

5.1.2.14.2 QOS Private Definitions

| Definition | Value | Description |
|---|---|---|
| LU_TINY | 1.0e-20 | The smallest number allowed in creating the $U$ matrix in a LU decomposition. Used in LUDecomp(). |
| SOLN_FRAC_TOL | 0.05 | Maximum fractional variation of the desired constant column from that of the forward calculation with respect to the largest magnitude element of the desired constant column. |
| SVD_MAX_ITS | 30 | Maximum number of iterations in the singular value decomposition. |
| SVD_ZERO_VALUE | 1.0e-6 | Smallest magnitude element allowed in $w$ matrix (see *Press, et al.*). |

5.1.3 Field Computation Software Description

The FCS consists of those functions that are responsible for describing the magnetic behavior of the superconducting MSS helmet cryostat coils. In this regard, functions are provided that allow the computation of the magnetic field, the force, and the individual partial derivatives through second order. Most of the functions that follow reply on the existence of specific files being present that describe the magnetic behavior of the two coil types. These coil types consisting of the (1) four X and Y coils and the (2) two Z coils. Also required is a file that specifies the location of the coil midplanes with respect to helmet coordinates (i.e., the coordinate system referenced by the SD where the origin of helmet coordinates nearly corresponds to the intersection of the six coil axes. The field computations results are stored internally for efficiency. Before any field computation may be done, the files must be loaded.

5.1.3.1 Calc_B()

Calculates the magnetic field for the MSS at a specific point in space given a position in helmet coordinates and a set of six currents. It is assumed that InitArrays() has been called.

| Interface | *int Calc_B( coord_3d p, float I[], vec_3d *B )* | |
|---|---|---|
| Type | Variable | Data Description |
| *Input* | p | Structure to the position (m) to evaluate the magnetic field. |
| | I | Array containing currents (A) for the six coils allocated according to $I[1..6]$. An enumeration is provided in the header field_comp.h for easy identification of the current elements.<br><br>XPOS = 1   XNEG = 2<br>YPOS = 3   YNEG = 4<br>ZPOS = 5   ZNEG = 6 |
| *Output* | B | Structure to the evaluated magnetic field. |
| *Modified* | *(None)* | |
| *Return* | Returns status code according to<br><br>_BadInput:   The position was improperly entered.<br>_FAIL:        An error occurred in calculating the field information.<br>_PASS:        No error occurred. | |

5.1.3.2 Calc_d2B()

Calculates the second derivatives of the magnetic field for the MSS at a specific point in space given a position in helmet coordinates and a set of six currents. It is assumed that InitArrays() has been called.

| Interface | *int Calc_d2B( coord_3d p, float I[], vec_der2_3d *d2B )* | |
|---|---|---|
| Type | Variable | Data Description |
| *Input* | p | Structure to the position (m) to evaluate the magnetic field. |
| | I | Array containing currents (A) for the six coils allocated according to $I[1..6]$. An enumeration is provided in the header field_comp.h for easy identification of the current elements.<br><br>XPOS = 1   XNEG = 2<br>YPOS = 3   YNEG = 4 |

| | | ZPOS = 5   ZNEG = 6 |
|---|---|---|
| Output | d2B | Structure to the evaluated second partials of the magnetic field. |
| Modified | (None) | |
| Return | Returns status code according to<br><br>_BadInput:         The position was improperly entered.<br>_FAIL:               An error occurred in calculating the field information.<br>_PASS:              No error occurred. | |

5.1.3.3 Calc_dB()

Calculates the first derivatives of the magnetic field for the MSS at a specific point in space given a position in helmet coordinates and a set of six currents. It is assumed that InitArrays() has been called.

| Interface | int Calc_dB( coord_3d p,  float I[],  vec_der_3d *dB ) | |
|---|---|---|
| Type | Variable | Data Description |
| Input | p | Structure to the position (m) to evaluate the magnetic field. |
| | I | Array containing currents (A) for the six coils allocated according to $I[1..6]$. An enumeration is provided in the header field_comp.h for easy identification of the current elements.<br><br>XPOS = 1   XNEG = 2<br>YPOS = 3   YNEG = 4<br>ZPOS = 5   ZNEG = 6 |
| Output | dB | Structure to the evaluated first partials of the magnetic field. |
| Modified | (None) | |
| Return | Returns status code according to<br><br>_BadInput:         The position was improperly entered.<br>_FAIL:               An error occurred in calculating the field information.<br>_PASS:              No error occurred. | |

5.1.3.4 Calc_F()

Calculates the magnetic force on a permanent small magnetic moment for the MSS at a specific point in space given a position in helmet coordinates, the magnetic moment, and a set of six currents. It is assumed that InitArrays() has been called.

| Interface | int Calc_F( coord_3d p,  float I[],  float moment,  vec_3d *F ) | |
|---|---|---|
| Type | Variable | Data Description |
| Input | p | Structure to the position (m) to evaluate the magnetic field. |
| | I | Array containing currents (A) for the six coils allocated according to $I[1..6]$. An enumeration is provided in the header field_comp.h for easy identification of the current elements.<br><br>XPOS = 1   XNEG = 2<br>YPOS = 3   YNEG = 4<br>ZPOS = 5   ZNEG = 6 |

|  | moment | The magnetic moment of the small permanent magnet. Must be greater than 0. |
|---|---|---|
| Output | F | Structure to the evaluated second partials of the magnetic field. |
| Modified | (None) | |
| Return | Returns status code according to<br><br>_BadInput_:           The position was improperly entered.<br>_FAIL_:               An error occurred in calculating the field information.<br>_PASS_:              No error occurred. | |

5.1.3.5 Calc_PermF()

Calculates the magnetic force on a permeable small magnetic moment for the MSS at a specific point in space given a position in helmet coordinates, the magnetic moment, and a set of six currents. It is assumed that InitArrays() has been called.

| Interface | int Calc_PermF( coord_3d p, float I[], float m_sat, float B_sat, vec_3d *F ) | |
|---|---|---|
| Type | Variable | Data Description |
| Input | p | Structure to the position (m) to evaluate the magnetic field. |
| | I | Array containing currents (A) for the six coils allocated according to $I[1..6]$. An enumeration is provided in the header field_comp.h for easy identification of the current elements.<br><br>XPOS = 1    XNEG = 2<br>YPOS = 3    YNEG = 4<br>ZPOS = 5    ZNEG = 6 |
| | m_sat | The saturation moment of the small permanent magnet. Must be greater than 0. |
| | B_sat | The saturation magnetic field (T). Must be greater than 0. |
| Output | F | Structure to the evaluated second partials of the magnetic field. |
| Modified | (None) | |
| Return | Returns status code according to<br><br>_BadInput_:           The position was improperly entered.<br>_FAIL_:               An error occurred in calculating the field information.<br>_PASS_:             No error occurred. | |

5.1.3.6 CalcBForCoil()

This function calculates the field information for each specified coil in the two dimensional coordinate system of the respective coil. The field data is then mapped into three dimensional by symmetry arguments and then mapped into helmet coordinates with the appropriate transformations. It is assumed that InitArrays() has been called.

| Interface | int CalcBForCoil( int Coil, coord_3d p, float I, vec_3d *B, vec_der_3d *dB, vec_der2_3d *d2B ) | |
|---|---|---|
| Type | Variable | Data Description |
| Input | Coil | The coil to examine. This value may be denoted by the following definitions contained in the header file: |

|   |   | XPOS = 1     XNEG = 2 |
|---|---|---|
|   |   | YPOS = 3     YNEG = 4 |
|   |   | ZPOS = 5     ZNEG = 6 |
|   | *p* | Structure to the MDV position (m). |
|   | *I* | Array containing currents (A) for the six coils allocated according to *I*[1..6]. An enumeration is provided in the header field_comp.h for easy identification of the current elements.<br><br>XPOS = 1     XNEG = 2<br>YPOS = 3     YNEG = 4<br>ZPOS = 5     ZNEG = 6 |
| *Output* | *B* | The magnetic field (T). |
|   | *dB* | The first-order partial derivatives (T/m). |
|   | *d2B* | The second-order partial derivatives (T/m-m). |
| *Modified* | *(None)* |   |
| *Return* | Returns status code according to<br><br>_BadInput:           The coil identification was not specified correctly.<br>_FAIL:               Error occurred while reading data tables.<br>_PASS:              No error occurred. ||

5.1.3.7 CalcFieldData()

Calculates all field information for the position passed into the function. It is assumed that InitArrays() has been called.

| Interface | *int CalcFieldData( coord_3d p )* ||
|---|---|---|
| Type | Variable | Data Description |
| *Input* | *p* | Structure to the MDV position (m). |
| *Output* | *(None)* |   |
| *Modified* | *(None)* |   |
| *Return* | Returns status code according to<br><br>_BadInput:           The position was out of scope of the data files.<br>_FAIL:               Error occurred while reading data tables.<br>_PASS:              No error occurred. ||

5.1.3.8 CheckPositionVsTable()

Determines if the passed position is outside the reliable range of the respective magnetic field data table. If a violation occurs, the returned error flag indicates in which direction the violation occurred. It is assumed that InitArrays() has been called.

| Interface | *int CheckPositionVsTable( coord_3d p )* ||
|---|---|---|
| Type | Variable | Data Description |
| *Input* | *p* | Structure to the MDV position (m). |

| Output | (None) | |
|---|---|---|
| Modified | (None) | |
| Return | Returns status code according to | |
| | _PASS: | No error occurred. |
| | _XposEr: | The violation occurred in the positive x- direction. |
| | _XnegEr: | The violation occurred in the negative x- direction. |
| | _YposEr: | The violation occurred in the positive y- direction. |
| | _YnegEr: | The violation occurred in the negative y- direction. |
| | _ZposEr: | The violation occurred in the positive z- direction. |
| | _ZnegEr: | The violation occurred in the negative z- direction. |

5.1.3.9 DeinitArrays()

Deallocates the arrays used by the data tables for the two coil types. It is assumed that InitArrays() has been called.

| Interface | void DeinitArrays( void ) | |
|---|---|---|
| Type | Variable | Data Description |
| Input | (None) | |
| Output | (None) | |
| Modified | (None) | |
| Return | ( No return ) | |

5.1.3.10 GetFieldElements()

Retrieves the magnetic field information for each coil in a matrix format. On return, the information will be in the following form:

$$bMat[1..3][1..6] = \begin{Bmatrix} b_i(XPOS) & b_i(XNEG) & b_i(YPOS) & b_i(YNEG) & b_i(ZPOS) & b_i(ZNEG) \\ b_j(XPOS) & b_j(XNEG) & b_j(YPOS) & b_j(YNEG) & b_j(ZPOS) & b_j(ZNEG) \\ b_k(XPOS) & b_k(XNEG) & b_k(YPOS) & b_k(ZNEG) & b_k(ZPOS) & b_k(ZNEG) \end{Bmatrix}$$

where the labels XPOS... ZNEG correspond to the definitions $$XPOS = 1 \quad XNEG = 2$$
$$YPOS = 3 \quad YNEG = 4$$
$$ZPOS = 5 \quad ZNEG = 6$$

It is assumed that InitArrays() has been called.

| Interface | int GetFieldElements( coord_3d p, float **bMat ) | |
|---|---|---|
| Type | Variable | Data Description |
| Input | p | Structure to the MDV position (m). |
| Output | bMat | Matrix holding the magnetic field information for the six coils. |
| Modified | (None) | |
| Return | Returns status code according to | |
| | _BadInput: | The position was out of scope of the data tables. |

| | _FAIL: | Error occurred while interpolating the data tables. |
| --- | --- | --- |
| | _PASS: | No error occurred. |

5.1.3.11 GetXYDataPlaneInfo()

Interpolates the field information in the symmetric polar plane for the X and Y coils given the sample location $r$ and $l$. Zeroth, first, and second order field data is returned for the input position. It is assumed that InitArrays() has been called.

| Interface | int GetXYDataPlaneInfo( float r, float l, float *Br, float *Bl, der_polar *dBr, der_polar *dBl, der2_polar *d2Br, der2_polar *d2Bl ) | |
| --- | --- | --- |
| Type | Variable | Data Description |
| Input | r | Radial position in table to interpolate (m). |
| | l | Axial position in table to interpolate (m). |
| Output | Br | Radial component of the magnetic field (T). |
| | Bl | Axial component of the magnetic field (T). |
| | dBr | First derivatives of radial component of the magnetic field (T/m). |
| | dBl | First derivatives of axial component of the magnetic field (T/m). |
| | d2Br | Second derivatives of radial component of the magnetic field (T/m$^2$). |
| | d2Bl | Second derivatives of axial component of the magnetic field (T/m$^2$). |
| Modified | (None) | |
| Return | Returns status code according to<br><br>_FAIL:    Failure in spline interpolation.<br>_PASS:    No error occurred. | |

5.1.3.12 GetZDataPlaneInfo()

Interpolates the field information in the symmetric polar plane for the Z coils given the sample location $r$ and $l$. Zeroth, first, and second order field data is returned for the input position. It is assumed that InitArrays() has been called.

| Interface | int GetZDataPlaneInfo( float r, float l, float *Br, float *Bl, der_polar *dBr, der_polar *dBl, der2_polar *d2Br, der2_polar *d2Bl ) | |
| --- | --- | --- |
| Type | Variable | Data Description |
| Input | r | Radial position in table to interpolate (m). |
| | l | Axial position in table to interpolate (m). |
| Output | Br | Radial component of the magnetic field (T). |
| | Bl | Axial component of the magnetic field (T). |
| | dBr | First derivatives of radial component of the magnetic field (T/m). |
| | dBl | First derivatives of axial component of the magnetic field (T/m). |
| | d2Br | Second derivatives of radial component of the magnetic field (T/m$^2$). |
| | d2Bl | Second derivatives of axial component of the magnetic field (T/m$^2$). |

| Modified | (None) | |
|---|---|---|
| Return | Returns status code according to<br><br>_FAIL:       Failure in spline interpolation.<br>_PASS:      No error occurred. | |

5.1.3.13 InitArrays()

Allocates the memory holding the field information for the X and Y coils and the Z coils by and calculates the splines for the two coil types. A flag is passed in to indicate whether the headers to the data files should be streamed to the screen when loaded.

| Interface | int InitArrays( int display_flag ) | |
|---|---|---|
| Type | Variable | Data Description |
| Input | display_flag | Flag that specifies if headers should be streamed to the screen when read. *display_flag* should be set to one of the following value: SHOW_INFO or HIDE_INFO which are defined in the header file. |
| Output | (None) | |
| Modified | (None) | |
| Return | Returns status code according to<br><br>_BadInput:    *display_flag* was improperly set.<br>_FAIL:           Unable to open files or allocate memory.<br>_PASS:          No error occurred. | |

5.1.3.14 LoadXYCoilInfo()

Loads the magnetic field data table for the X and Y coils into memory. It is assumed that InitArrays() has been called.

| Interface | int LoadXYCoilInfo( data_file coil_data ) | |
|---|---|---|
| Type | Variable | Data Description |
| Input | coil_data | Structure possessing the information regarding the layout of the data table file to be loaded. |
| Output | (None) | |
| Modified | (None) | |
| Return | Returns status code according to<br><br>_FAIL:      Unable to open files.<br>_PASS:     No error occurred. | |

5.1.3.15 LoadZCoilInfo()

Loads the magnetic field data table for the Z coils into memory. It is assumed that InitArrays() has been called.

| Interface | int LoadZCoilInfo( data_file coil_data ) | |
|---|---|---|
| Type | Variable | Data Description |

| Input | coil_data | Structure possessing the information regarding the layout of the data table file to be loaded. |
|---|---|---|
| Output | (None) | |
| Modified | (None) | |
| Return | Returns status code according to<br><br>_FAIL:   Unable to open files.<br>_PASS:   No error occurred. | |

5.1.3.16 ReadCoilArray()

Loads the files possessing the locations of the coil midplanes with respect to helmet coordinates into memory. A flag is passed in to indicate whether the headers to the data files should be streamed to the screen when read.

| Interface | int ReadCoilArray( char file[], int display_flag ) | |
|---|---|---|
| Type | Variable | Data Description |
| Input | file | Name of the file which contains the locations of the coil midplanes with respect to helmet coordinates. |
| | display_flag | Flag that specifies if headers should be streamed to the screen when read. *display_flag* should be set to one of the following value: SHOW_INFO or HIDE_INFO which are defined in the header file. |
| Output | (None) | |
| Modified | (None) | |
| Return | Returns status code according to<br><br>_BadInput:   *display_flag* was improperly set.<br>_FAIL:       Unable to open files.<br>_PASS:       No error occurred. | |

5.1.3.17 ReportPathAssignment()

Reports the name and path of the data file for the FCS as a print to the standard error device.

| Interface | void ReportPathAssignment( void ) | |
|---|---|---|
| Type | Variable | Data Description |
| Input | (None) | |
| Output | (None) | |
| Modified | (None) | |
| Return | ( No return. ) | |

5.1.3.18 ScaleFieldInfo()

Multiplies the field information by the input current.

| Interface | void ScaleFieldInfo( float I, float *Br, float *Bl, der_polar *dBr, der_polar *dBl, |
|---|---|

| | *der2_polar *d2Br, der2_polar *d2Bl* ) | |
|---|---|---|
| Type | Variable | Data Description |
| Input | I | Current(A) for which the field components are multiplied. Allocated according to I[1..6]. |
| Output | (None) | |
| Modified | Br | Radial component of the magnetic field (T). |
| | Bl | Axial component of the magnetic field (T). |
| | dBr | First derivatives of radial component of the magnetic field (T/m). |
| | dBl | First derivatives of axial component of the magnetic field (T/m). |
| | d2Br | Second derivatives of radial component of the magnetic field (T/m$^2$). |
| | d2Bl | Second derivatives of axial component of the magnetic field (T/m$^2$). |
| Return | ( No return. ) | |

5.1.3.19 SetFilePath()

Changes the path of the data file containing the midplane locations of the six coils with respect to helmet coordinates.

| Interface | *void SetFilePath( char file[] )* | |
|---|---|---|
| Type | Variable | Data Description |
| Input | file | New path of the file possessing the midplane locations of the six coils with respect to helmet coordinates. |
| Output | (None) | |
| Modified | (None) | |
| Return | ( No return. ) | |

5.1.3.20 Spline1D()

Calculates the one-dimensional spline of a set of tabulated data. The input parameters $x[1..n]$ and $y[1..n]$ are related according to $y = f(x)$ where the values of $x[1..n]$ are discrete and tabulated so that $x[1] < x[2] < ... < x[n]$. The parameters $yp1$ and $ypn$ specify the first derivative at the beginning and end of the interpolating function, respectively. On return, the array $d2y[1..n]$ contains the second derivatives of the interpolating function for each tabulated point. If $yp1$ or $ypn > 0.99e30$, then the second derivative at the respective point is set to zero and the boundary is said to be "natural"; otherwise, the first derivative values of $yp1$ and $ypn$ are used..

| Interface | *int Spline1D( float x[], float y[], int n, float yp1, float ypn, float d2y[] )* | |
|---|---|---|
| Type | Variable | Data Description |
| Input | x | Tabulated data for independent variable. $x[1..n]$ must satisfy $x[1] < x[2] < ... < x[n]$. |
| | y | Function evaluations for the tabulated data $x[1..n]$. |
| | n | The number of tabulated points. $n$ must be greater than 1. |

| | ypl | First derivative at the lower boundary. If greater than 0.99e30, the second derivative is set to zero. |
|---|---|---|
| | ypn | First derivative at the upper boundary. If greater than 0.99e30, the second derivative is set to zero. |
| Output | d2y | Second derivatives of the interpolating function at the positions specified by $x[1..n]$. |
| Modified | | |
| Return | Returns status code according to<br><br>_BadInput_:             n must be greater than 1.<br>_FAIL_:                 Allocation error occured.<br>_PASS_:                No error occurred. | |

5.1.3.21 Spline1DInt()

Interpolates the value of a one-dimensional function at the desired point given a set of tabulated points and the function evaluations and the second derivatives at those point. The input parameters $xa[1..n]$ are tabulated so that $xa[1] < xa[2] < ... < xa[n]$. On exit, the interpolated value of the function at the desired point and the corresponding first and second derivatives are returned.

| Interface | int Spline1DInt( float xa[], float ya[], float y2a[], int n, float x, float *y, float *dy, float *d2y ) | |
|---|---|---|
| Type | Variable | Data Description |
| Input | xa | Tabulated data for independent variable. $xa[1..n]$ must satisfy $xa[1] < xa[2] < ... < xa[n]$. |
| | ya | Function evaluations for the tabulated data $xa[1..n]$. |
| | y2a | Second derivatives of the interpolating function at the positions specified by $xa[1..n]$. |
| | n | The number of tabulated points. n must be greater than 1. |
| | x | Point at which the function is to be interpolated. |
| Output | y | Interpolated value of the function at the point x. |
| | dy | Interpolated value of the function's first derivative at the point x. |
| | d2y | Interpolated value of the function's second derivative at the point x. |
| Modified | (None) | |
| Return | Returns status code according to<br><br>_BadInput_:             n must be greater than 1.<br>_FAIL_:                 Components of $xa[1..n]$ must be distinct.<br>_PASS_:                No error occurred. | |

5.1.3.22 Spline2D()

Calculates the two-dimensional splines of a set of tabulated data. Given the input parameters $ra2[1..nr]$ where $ra[1] < ra[2] < ... < ra[nr]$, one-dimensional cubic splines are caluclated from the rows of $Ba[1..nl][1..nr]$. The parameters *low* and *high* specify the first derivative at the beginning and end of the interpolating function, respectively. On return, the array $d2Ba[1..nl][1..nr]$ contains the second derivatives of the interpolating function for each tabulated point. If *low* or *high* > 0.99e30, then the second derivative at the respective point is set to zero and the boundary is said to be "natural"; otherwise, the first derivative values of *low* and *high* are used..

| Interface | int Spline2D( float ra[], float Ba[], int nl, int nr, float low, float high, float d2Ba ) | |
|---|---|---|
| Type | Variable | Data Description |
| Input | ra | Tabulated data for independent variable. $ra[1..nr]$ must satisfy $ra[1] < ra[2] <...< ra[nr]$. |
| | Ba | Function evaluations for the tabulated data $ra[1..nr]$. |
| | nl | The number of tabulated points in x1. $nl$ must be greater than 1. |
| | nr | The number of tabulated points in x2. $nr$ must be greater than 1. |
| | low | First derivative at the lower boundaries. If greater than 0.99e30, the second derivatives are set to zero. |
| | high | First derivative at the upper boundaries. If greater than 0.99e30, the second derivatives are set to zero. |
| Output | d2Ba | Second derivatives of the interpolating function at the positions specified by $nl \times nr$ tabulation. |
| Modified | (None) | |
| Return | Returns status code according to<br><br>_BadInput:  $\qquad$ nl and nr must be greater than 1.<br>_FAIL:  $\qquad$ Allocation error occured.<br>_PASS:  $\qquad$ No error occurred. | |

5.1.3.23 Spline2DInt()

Interpolates the value of a two-dimensional function at the desired point given a set of tabulated points and the function evaluations and the second derivatives at those point. The input parameters $la[1..n1]$ and $ra[1..n2]$ are tabulated so that $la[1] < la[2] <...< la[n1]$ and $ra[1] < ra[2] <...< ra[n2]$. On exit, the interpolated value of the function at the desired point and the corresponding first and second derivatives are returned.

| Interface | int Spline2DInt( float la[], float ra[], float **Ba[], float **d2Ba, int nl, int nr, float l, float r, float *B, der_polar *dB, der2_polar *d2B ) | |
|---|---|---|
| Type | Variable | Data Description |
| Input | la | Tabulated data for independent variable. $la[1..nl]$ must satisfy $la[1] < la[2] <...< la[nl]$. |
| | ra | Tabulated data for independent variable. $ra[1..nr]$ must satisfy $ra[1] < ra[2] <...< ra[nr]$. |
| | Ba | Function evaluations for the tabulated data $ra[1..nr]$. |
| | d2Ba | Second derivatives of the interpolating function at the positions specified by $nl \times nr$ tabulation. |
| | nl | The number of tabulated points in x1. $nl$ must be greater than 1. |
| | nr | The number of tabulated points in x2. $nr$ must be greater than 1. |

| | *l* | The *l* component of the point to interpolate the function. |
|---|---|---|
| | *r* | The *r* component of the point to interpolate the function. |
| Output | B | Interpolated value of the function at the point (*l, r*). |
| | dB | Interpolated value of the function's first derivative at the point (*l, r*). |
| | d2B | Interpolated value of the function's second derivative at the point (*l, r*). |
| Modified | (None) | |
| Return | Returns status code according to | |
| | _BadInput: | *nl* and *nr* must be greater than 1. |
| | _FAIL: | Components of *la*[1..*nl*] and *ra*[1..*nr*] must be distinct. |
| | _PASS: | No error occurred. |

5.1.3.24 FCS Structures

Below are listed the structures that are public to the FCS. The coordinate structure is denoted by x-, y-, and z- elements for position, which is mathematically appropriate. The vector structure reflects the proper mathematical i-, j-, and k- elements. For the vector structures, the magnitude is also passed.

5.1.3.24.1 FCS Public Structures

*5.1.3.24.1.1 coord_3d*

This structure specifies the location of the MDV in the helmet cryostat.

| Element | Data Type | Definition |
|---|---|---|
| x | float | Position along the x-axis. |
| y | float | Position along the y-axis. |
| z | float | Position along the z-axis. |

*5.1.3.24.1.2 vec_3d*

This structure specifies a vector in the helmet cryostat.

| Element | Data Type | Definition |
|---|---|---|
| i | float | $i^{th}$ component of the vector. |
| j | float | $j^{th}$ component of the vector. |
| k | float | $k^{th}$ component of the vector. |
| mag | float | Magnitude of the vector. |

*5.1.3.24.1.3 der_3d*

This structure specifies the first-order directional derivatives in the helmet cryostat.

| Element | Data Type | Definition |
|---|---|---|
| dx | float | Variation in the x direction (i.e., $\partial/\partial x$). |
| dy | float | Variation in the x direction (i.e., $\partial/\partial y$). |
| dz | float | Variation in the x direction (i.e., $\partial/\partial z$). |

*5.1.3.24.1.4 der2_3d*

This structure specifies the second-order directional derivatives in the helmet cryostat.

| Element | Data Type | Definition |
|---------|-----------|------------|
| dx | der_3d | Variations in the x direction (i.e., $\partial/\partial x^2$, $\partial/\partial x \partial y$, $\partial/\partial x \partial z$). |
| dy | der_3d | Variations in the x direction (i.e., $\partial/\partial y \partial x$, $\partial/\partial y^2$, $\partial/\partial y \partial z$). |
| dz | der_3d | Variations in the x direction (i.e., $\partial/\partial z \partial x$, $\partial/\partial z \partial y$, $\partial/\partial z^2$). |

*5.1.3.24.1.5 vec_der_3d*

This structure specifies the first-order directional derivatives in the helmet cryostat.

| Element | Data Type | Definition |
|---------|-----------|------------|
| i | der_3d | First partials of $i^{th}$ component. |
| j | der_3d | First partials of $j^{th}$ component. |
| k | der_3d | First partials of $k^{th}$ component. |
| mag | der_3d | First partials of magnitude. |

*5.1.3.24.1.6 vec_der2_3d*

This structure specifies the second-order directional derivatives in the helmet cryostat.

| Element | Data Type | Definition |
|---------|-----------|------------|
| i | der2_3d | Second partials of $i^{th}$ component. |
| j | der2_3d | Second partials of $j^{th}$ component. |
| k | der2_3d | Second partials of $k^{th}$ component. |
| mag | der2_3d | Second partials of magnitude. |

5.1.3.24.2 FCS Private Structures

*5.1.3.24.2.1 data_file*

This structure specifies all pertinent information regarding the data tables for the two coil types that comprise the MSS helmet cryostat.

| Element | Data Type | Definition |
|---------|-----------|------------|
| file[100] | char | Name of the data file corresponding to coil. |
| I_ref | float | Reference current at which data table was created (A). |
| L_start | float | Starting tabulation in the axial direction (m). |
| L_end | float | Ending tabulation in the axial direction (m). |
| R_end | float | Ending tabulation in the radial direction (m). |
| L_tab | float | Tabulation in the axial direction (m). |
| R_tab | float | Tabulation in the radial direction (m). |
| L_num | int | Number of elements in axial direction. |

| | | |
|---|---|---|
| R_num | int | Number of elements in radial direction. |
| Rin | float | Inner coil radius (m). |
| Rout | float | Outer coil radius (m). |
| width | float | Coil thickness (m). |

*5.1.3.24.2.2 der_polar*

This structure specifies the first-order directional derivatives in polar coordinates.

| Element | Data Type | Definition |
|---|---|---|
| dr | float | Variation in the radial direction (i.e., $\partial/\partial r$). |
| dl | float | Variation in the axial direction (i.e., $\partial/\partial l$). |

*5.1.3.24.2.3 der2_polar*

This structure specifies the first-order directional derivatives in polar coordinates.

| Element | Data Type | Definition |
|---|---|---|
| dr | der_polar | Variations in the radial direction (i.e., $\partial/\partial r^2$, $\partial/\partial r \partial l$). |
| dl | der_polar | Variations in the axial direction (i.e., $\partial/\partial l \partial r$, $\partial/\partial l^2$). |

5.1.3.25 FCS Enumerations 5.1.3.25.1 FCS Public Enumerations

*5.1.3.25.1.1 field_comp_errors*

Below are listed all status codes that denote the errors that can occur for the functions of the FCS.

| Enumeration | Value | Description |
|---|---|---|
| _XposEr | -1 | Position violation in positive x-axis. |
| _XnegEr | -2 | Position violation in negative x-axis. |
| _YposEr | -3 | Position violation in positive y-axis. |
| _YnegEr | -4 | Position violation in negative y-axis. |
| _ZposEr | -5 | Position violation in positive z-axis. |
| _ZnegEr | -6 | Position violation in negative z-axis. |

5.1.3.26 FCS Macros and Definitions 5.1.3.26.1 FCS Private Macros

| Macro | Description |
|---|---|
| MM_TO_M( a ) | Converts millimeters to meters. |
| NORM3( a, b, c ) | Calculates the norm of three numbers. |

5.1.3.26.2 FCS Public Definitions

| Definitions | Value | Description |
|---|---|---|
| SHOW_INFO | 1 | Flag to indicate that headers to files should be displayed. |
| HIDE_INFO | 0 | Flag to indicate that headers to files should not be displayed. |
| DEF_COIL_ARRAY_PATH | "coil_array.txt" | Default file specifying coil locations. |
| XPOS | 1 | Coil on positive x-axis (i.e., XA coil). |
| XNEG | 2 | Coil on negative x-axis (i.e., XB coil). |
| YPOS | 3 | Coil on positive y-axis (i.e., YA coil). |
| YNEG | 4 | Coil on negative y-axis (i.e., YB coil). |
| ZPOS | 5 | Coil on positive z-axis (i.e., ZA coil). |
| ZNEG | 6 | Coil on negative z-axis (i.e., ZB coil). |

5.1.3.26.3 FCS Private Definitions

| Definitions | Value | Description |
|---|---|---|
| VERSION | 1.0 | Version of the FCS. |
| YES | 1 | Affirmative flag. |
| NO | 0 | Negative flag. |
| FTOL | 1.0e-7 | Lower floating-point limit for any number that is not assumed equal to zero. |
| DEINITIALIZED | 0 | Flag specifying if data table arrays are deinitialized. |
| INITIALIZED | 1 | Flag specifying if data table arrays are initialized. |
| RTOL | 1.0e-5 | The smallest radial distance that is not assumed equal to zero in the data tables for the two coil types. |

5.1.4 Field Generation Software Description

The FGS consists of those functions and procedures that allow the creation of the data tables for the helmet cryostat coils. These files serve as support for the FCS. In this respect, three files are required. The first two files possess the magnetic field information in tabulated form for the X and Y coils and the Z coils. These files make use of the fact that the magnetic field associated with the magnetic coils is symmetric with respect to the midplane axis. The last file contains the midplane locations of the six coils with respect to helmet coordinates as well as the names of the aforementioned data files. It is assumed that each coil's midplane is perpendicular to the respecting intersecting cardinal axis.

5.1.4.1 DefineCoilArray()

Executable that allows the specification of the coil midplanes with respect to helmet coordinates via user prompt. The information is written to the desired file in the proper format for the FCS.

| Interface | int DefineCoilArray( void ) | |
|---|---|---|
| Type | Variable | Data Description |
| Input | (None) | |
| Output | (None) | |
| Modified | (None) | |
| Return | Returns status code according to<br>_FAIL:            Unable to write files.<br>_PASS:           No error occurred. | |

5.1.4.2 FieldGenExe()

Executable that generates the magnetic field data tables for the coils of the MSS via user prompt.

| Interface | int FieldGenExe( void ) | |
|---|---|---|
| Type | Variable | Data Description |
| Input | (None) | |
| Output | (None) | |
| Modified | (None) | |
| Return | Returns status code according to<br>_FAIL:            Unable to write files.<br>_PASS:           No error occurred. | |

5.1.4.3 func_bl()

Axial calculation of the magnetic field as a function of the polar angle *phi*. Note that several global variables are used in this call.

| Interface | float func_bl( float phi ) | |
|---|---|---|
| Type | Variable | Data Description |
| Input | phi | Polar angle (rad). |

| Output | (None) | |
|---|---|---|
| Modified | (None) | |
| Return | On exit, returns the axial magnetic field for the specified polar angle. | |

5.1.4.4 func_br()

Radial calculation of the magnetic field as a function of the polar angle *phi*. Note that several global variables are used in this call.

| Interface | float func_br( float phi ) | |
|---|---|---|
| Type | Variable | Data Description |
| Input | phi | Polar angle (rad). |
| Output | (None) | |
| Modified | (None) | |
| Return | On exit, returns the radial magnetic field for the specified polar angle. | |

5.1.4.5 GenerateFile()

Generates the tabulated data table for a coil with the specified physical properties and integration parameters for Romberg integration.

| Interface | int GenerateFile( coil_param Coil, integration_param IntParam ) | |
|---|---|---|
| Type | Variable | Data Description |
| Input | Coil | Structure to the physical properties of the specified coil. |
| | IntParam | Structure to the integration parameters used in constructing the data table. |
| Output | (None) | |
| Modified | (None) | |
| Return | Returns status code according to<br><br>_FAIL_:        Unable to write files.<br>_PASS_:      No error occurred. | |

5.1.4.6 NthTrapStage()

This routine computes the nth stage of refinement of an extended trapezoidal rule for the single-variable function *func*. Since this function is only called from within *QRomb()*, where *lower* is confirmed to be less than *upper*, no error flag is returned here. Thus, it is assumed that *lower* is lesser than *upper*.

| Interface | float NthTrapStage( float (*func)(float), float lower, float upper ) | |
|---|---|---|
| Type | Variable | Data Description |
| Input | func | The single-variable function whose nth stage refinement (via the trapezoidal rule) is to be taken. |
| | lower | Lower limit to the integration. Must be lesser than *upper*. |
| | upper | Upper limit to the integration. Must be greater than *lower*. |

| | |
|---|---|
| Output | (None) |
| Modified | (None) |
| Return | Returns the nth stage refinement of a function via the trapezoidal rule. |

5.1.4.7 PolyInt()

Given the point $xa[1..n]$ and function evaluations at those points $ya[1..n]$, and given the point $x$, this function returns the value of the function at $x$ via polynomial interpolation. Also returned is the error estimate in the function. The input arrays are also assumed to be unit offset. If the arrays are zero offset, be sure to subtract 1. Also, two input elements of $xa[1..n]$ cannot be identical within roundoff. If so, an error flag is returned.

| Interface | int PolyInt( float xa[], float ya[], int n, float x, float *y, float *dy ) | |
|---|---|---|
| Type | Variable | Data Description |
| Input | xa | Array containing the data at which the functions are evaluated where xa is allocated according to $xa[1..n]$. |
| | ya | Array containing the function evaluations corresponding to the array $ya[1..n]$ where ya is allocated according to $ya[1..n]$. |
| | n | The number of data points. This value must be greater than 1. |
| | x | The point at which the function is to be evaluated. |
| Output | y | The polynomial interpolation of the function at the desired point $x$. |
| | dy | The error estimate in the polynomial interpolation of the function at the desired point $x$. |
| Modified | (None) | |
| Return | Returns status code according to<br>_BadInput:     Input error with $xa[1..n]$ or $n$.<br>_PASS:     No error occurred. | |

5.1.4.8 QRomb()

Returns the integral of the single-variable function *func* from the lower limit $a$ to the upper limit $b$. The integration is executed via Romberg's method of order 2K. (See *Numerical Recipes*, p. 140.) On return, error associated with the integration is also returned.

| Interface | int QRomb( float (*func)(float), float lower, float upper, float *int_val, float *err ) | |
|---|---|---|
| Type | Variable | Data Description |
| Input | func | The single-variable function to integrate from the lower to upper boundary. |
| | lower | Lower limit to the integration. Must be lesser than *upper*. |
| | upper | Upper limit to the integration. Must be greater than *lower*. |
| Output | int_value | Evaluation of the closed integral. |
| | err | The error estimate associated with the closed integral. |
| Modified | (None) | |

| Return | Returns status code according to |
| --- | --- |
| | _BadInput: lower must be less than upper. |
| | _FAIL: Unable to interpolate point. |
| | _PASS: No error occurred. |

5.1.4.9 SetCoilParam()

This function sets the physical properties of the magnetic coil (by user prompt). These properties include the following: The outer radius, inner radius, thickness, number of filament windings, and current.

| Interface | void SetCoilParam( coil_param *Coil ) | |
| --- | --- | --- |
| Type | Variable | Data Description |
| Input | (None) | |
| Output | Coil | Structure to the physical properties of the magnetic coils. |
| Modified | (None) | |
| Return | ( No return. ) | |

5.1.4.10 SetCurrent()

Enables the user to set the reference current (A) of the magnetic coil (by user prompt).

| Interface | double SetThickness( void ) | |
| --- | --- | --- |
| Type | Variable | Data Description |
| Input | (None) | |
| Output | (None) | |
| Modified | (None) | |
| Return | Returns the user specified reference current of the magnetic coil (A). | |

5.1.4.11 SetFuncParam()

Sets the internal global variables to those specified in the structure *Coil* for use in the integration functions.

| Interface | void SetFuncParam( coil_param Coil ) | |
| --- | --- | --- |
| Type | Variable | Data Description |
| Input | Coil | Structure to the physical properties of the specified coil. |
| Output | (None) | |
| Modified | (None) | |
| Return | ( No return. ) | |

5.1.4.12 SetInRad()

Enables the user to set the inner radius of the magnetic coil (by user prompt).

| Interface | double SetInRad( void ) |
| --- | --- |

| Type | Variable | Data Description |
|---|---|---|
| Input | (None) | |
| Output | (None) | |
| Modified | (None) | |
| Return | Returns the user specified inner radius of the magnetic coil (m). | |

5.1.4.13 SetOutRad()

Enables the user to set the outer radius of the magnetic coil (by user prompt).

| Interface | double SetOutRad( void ) | |
|---|---|---|
| Type | Variable | Data Description |
| Input | (None) | |
| Output | (None) | |
| Modified | (None) | |
| Return | Returns the user specified outer radius of the magnetic coil (m). | |

5.1.4.14 SetRombParam()

Sets the internal global variables necessary for Romberg integration.

| Interface | void SetRombParam( integration_param IntParam ) | |
|---|---|---|
| Type | Variable | Data Description |
| Input | IntParam | Structure to the integration parameters necessary for Romberg integration. |
| Output | (None) | |
| Modified | (None) | |
| Return | ( No return. ) | |

5.1.4.15 SetRombEPS()

Allows the user to set the EPS (i.e., the fractional accuracy) of the Romberg integration function *QRomb()*. This is done by user prompt.

| Interface | float SetRombEPS( void ) | |
|---|---|---|
| Type | Variable | Data Description |
| Input | (None) | |
| Output | (None) | |
| Modified | (None) | |
| Return | Returns the user specified fractional accuracy for Romberg integration. | |

CERTIFICATE OF CORRECTION (continued)
U.S. Pat. No. 6,015,414

5.1.4.16 SetRombFilNum()

Allows the user to set the number of filaments which approximate the current density due to the coil windings for the Romberg integration function *QRomb()*. This is done by user prompt.

| Interface | *float SetRombFilNum( void )* | |
|---|---|---|
| Type | Variable | Data Description |
| *Input* | *(None)* | |
| *Output* | *(None)* | |
| *Modified* | *(None)* | |
| *Return* | Returns the user specified number of filaments which approximate the current density due to the coil windings for Romberg integration. | |

5.1.4.17 SetRombJMAX()

Allows the user to set the JMAX (i.e., the number of trapezoidal approximations) of the Romberg integration function *QRomb()*. This is done by user prompt.

| Interface | *float SetRombJMAX( void )* | |
|---|---|---|
| Type | Variable | Data Description |
| *Input* | *(None)* | |
| *Output* | *(None)* | |
| *Modified* | *(None)* | |
| *Return* | Returns the user specified number of trapezoidal approximations for Romberg integration. | |

5.1.4.18 SetRombK()

Allows the user to set the K (i.e., the number of points used to interpolate the function) of the Romberg integration function *QRomb()*. This is done by user prompt.

| Interface | *float SetRombK( void )* | |
|---|---|---|
| Type | Variable | Data Description |
| *Input* | *(None)* | |
| *Output* | *(None)* | |
| *Modified* | *(None)* | |
| *Return* | Returns the user specified number of points used to interpolate the function for Romberg integration. | |

5.1.4.19 SetRombMaxIts()

Allows the user to set the maximum number of iterations of the Romberg integration function *QRomb()*. This is done by user prompt. The value is not allowed to be greater than the maximum value of a long integer (2 147 483 647).

| Interface | *float SetRombMaxIts( void )* |
|---|---|

| Type | Variable | Data Description |
|---|---|---|
| Input | (None) | |
| Output | (None) | |
| Modified | (None) | |
| Return | Returns the user specified maximum number of iterations for Romberg integration. | |

5.1.4.20 SetThickness()

Enables the user to set the thickness of the magnetic coil (by user prompt).

| Interface | double SetThickness( void ) | |
|---|---|---|
| Type | Variable | Data Description |
| Input | (None) | |
| Output | (None) | |
| Modified | (None) | |
| Return | Returns the user specified thickness of the magnetic coil (m). | |

5.1.4.21 SetTurns()

Enables the user to set the number of filament windings of the magnetic coil (by user prompt).

| Interface | double SetTurns( void ) | |
|---|---|---|
| Type | Variable | Data Description |
| Input | (None) | |
| Output | (None) | |
| Modified | (None) | |
| Return | Returns the user specified number of filament windings of the magnetic coil. | |

5.1.4.22 ShowCoilParam()

Display the physical properties and integration parameters for the specified magnetic coil.

| Interface | void ShowCoilParam( coil_param Coil, integration_param IntParam ) | |
|---|---|---|
| Type | Variable | Data Description |
| Input | Coil | Structure to the physical properties of the specified coil. |
| | IntParam | Structure to the integration parameters used in constructing the data table. |
| Output | (None) | |
| Modified | (None) | |
| Return | ( No return. ) | |

5.1.4.23 ShowMenu()

Displays the menu for modeling the magnetic coils.

| Interface | *void ShowMenu( void )* | |
|---|---|---|
| Type | Variable | Data Description |
| *Input* | *(None)* | |
| *Output* | *(None)* | |
| *Modified* | *(None)* | |
| *Return* | ( No return. ) | |

5.1.4.24 Version()

Returns the version of the FGS.

| Interface | *float Version( void )* | |
|---|---|---|
| Type | Variable | Data Description |
| *Input* | *(None)* | |
| *Output* | *(None)* | |
| *Modified* | *(None)* | |
| *Return* | Returns the version of the FGS. | |

5.1.4.25 FGS Structures

5.1.4.25.1 FGS Private Structures

*5.1.4.25.1.1 coil_param*

This structure specifies all pertinent information regarding the physical properties of the respective coil.

| Element | Data Type | Definition |
|---|---|---|
| InRad | double | Inner radius (m). |
| OutRad | double | Outer radius (m). |
| Thick | double | Coil Thickness (m). |
| Turns | long int | Number of coil windings. |
| Current | double | Current on the coil (A). |

*5.1.4.25.1.2 integration_param*

A structure to the integration parameters intrinsic to Romberg integration.

| Element | Data Type | Definition |
|---|---|---|
| EPS | float | The smallest floating-point value not set to 0. |
| K | int | Number of points used in the extrapolation. |
| JMAX | int | Limit to the total number of steps. |

| | | |
|---|---|---|
| MaxIts | int | Maximum number of iterations in integration. |
| FilNum | int | The number of filaments approximating the windings. |

5.1.4.26 FGS Enumerations

5.1.4.26.1 FGS Public Enumerations

*5.1.4.26.1.1 field_gen_errors*

Below are listed all status codes that denote the errors that can occur for the functions of the FGS.

| Enumeration | Value | Description |
|---|---|---|
| _PASS | 1 | No error occurred. |
| _FAIL | 0 | Process failed. |

5.1.4.27 FCS Macros and Definitions

5.1.4.27.1 FGS Private Macros

| Macro | Description |
|---|---|
| MM_TO_M( a ) | Converts millimeters to meters. |
| M_TO_MM( a ) | Converts meters to millimeters. |

5.1.4.27.2 FGS Private Definitions

| Definitions | Value | Description |
|---|---|---|
| FTOL | 1.0e-7 | Smallest floating point number not set equal to zero |
| NO | 0 | Negative. |
| YES | 1 | Positive. |

5.1.5 Matrix Allocation Software Description

The functions contained in the MAS are responsible in allocating and deallocating matrices as needed. There are two elements in this regard. First, there are "vectors" which are treated the same as one-dimensional arrays (i.e., passed by a single pointer). This name is not to be confused with the structure used in the FCS (vec_3d) which describes the properties of a three-dimensional vector more appropriately, mathematically speaking. For the present purposes, "vector" and "one-dimensional array" are interchangeable in the MAS. Since some applications require integer vectors, two vector types exist as data, the integer vector and the floating point vector. And second, there are the floating point matrix functions which allocate and deallocate two dimensional arrays. The integer matrices are not required in the MNS. These functions are closely modeled from those presented by *Press et al.*

5.1.5.1 fmatrix()

Allocates a floating point matrix (i.e., two-dimensional array) from *nrl* to *nrh* in the rows and from *ncl* to *nch* in the columns. If unable to set the necessary memory aside or if the input parameters are improperly set, then a null pointer is returned (defined as _FAIL).

| Interface | float **fmatrix( int nrl, int nrh, int ncl, int nch ) | |
|---|---|---|
| Type | Variable | Data Description |
| *Input* | nrl | Lower row subscript range. *nrl* must be greater than or equal to 0. |
| | nrh | Upper row subscript range. *nrh* must be greater than or equal to *nrl*. |
| | ncl | Lower column subscript range. *ncl* must be greater than or equal to 0. |
| | nch | Upper column subscript range. *nch* must be greater than or equal to *ncl*. |
| *Output* | (None) | |
| *Modified* | (None) | |
| *Return* | Double pointer to a floating point matrix or _FAIL if unable to allocate memory. | |

5.1.5.2 free_fmatrix()

Deallocates a floating point matrix (i.e., two-dimensional array) from *nrl* to *nrh* in the rows and from *ncl* to *nch* in the columns. For example, $a = free\_fmatrix(2,6,1,4)$ frees the memory occupied by $a[2,6][1,4]$. If the input parameters are improperly set, then an error flag is returned.

| Interface | int free_fmatrix( float **m, int nrl, int nrh, int ncl, int nch ) | |
|---|---|---|
| Type | Variable | Data Description |
| *Input* | nrl | Lower row subscript range. *nrl* must be greater than or equal to 0. |
| | nrh | Upper row subscript range. *nrh* must be greater than or equal to *nrl*. |
| | ncl | Lower column subscript range. *ncl* must be greater than or equal to 0. |
| | nch | Upper column subscript range. *nch* must be greater than or equal to *ncl*. |
| *Output* | (None) | |
| *Modified* | m | Floating point matrix to deallocate. |
| *Return* | Returns status code according to | |
| | _BadInput: | Input parameter(s) were improperly entered. |

| | _PASS: | No error occurred. |
|---|---|---|

5.1.5.3 free_fvector()

Deallocates a floating point vector (i.e., one-dimensional array) from *nl* to *nh*. For example, *a = free_fvector( 3, 6 )* frees the memory occupied by *a[3..6]*. If the input parameters are improperly set, then an error flag is returned.

| Interface | *int free_fvector( float *v, int nl, int nh )* | |
|---|---|---|
| Type | Variable | Data Description |
| Input | nl | Lower row subscript range. *nl* must be greater than or equal to 0. |
| | nh | Upper row subscript range. *nh* must be greater than or equal to *nl*. |
| Output | (None) | |
| Modified | v | Floating point vector to deallocate. |
| Return | Returns status code according to <br><br> _BadInput:      Input parameter(s) were improperly entered. <br> _PASS:      No error occurred. | |

5.1.5.4 free_ivector()

Deallocates an integer point vector (i.e., one-dimensional array) from *nl* to *nh*. For example, *a = free_ivector( 3, 6 )* frees the memory occupied by *a[3..6]*. If the input parameters are improperly set, then an error flag is returned.

| Interface | *int free_ivector( int *v, int nl, int nh )* | |
|---|---|---|
| Type | Variable | Data Description |
| Input | nl | Lower row subscript range. *nl* must be greater than or equal to 0. |
| | nh | Upper row subscript range. *nh* must be greater than or equal to *nl*. |
| Output | (None) | |
| Modified | v | Integer point vector to deallocate. |
| Return | Returns status code according to <br><br> _BadInput:      Input parameter(s) were improperly entered. <br> _PASS:      No error occurred. | |

5.1.5.5 fvector()

Allocates a floating point vector (i.e., one-dimensional array) from *nl* to *nh*. If unable to set the necessary memory aside or if the input parameters are improperly set, then a null pointer is returned (defined as _FAIL).

| Interface | *float *fvector( int nl, int nh )* | |
|---|---|---|
| Type | Variable | Data Description |
| Input | nl | Lower subscript range. *nl* must be greater than or equal to 0. |

| | nh | Upper subscript range. *nh* must be greater than or equal to *nl*. |
|---|---|---|
| *Output* | *(None)* | |
| *Modified* | *(None)* | |
| *Return* | Pointer to a floating point vector or _FAIL if unable to allocate memory. | |

5.1.5.6 ivector()

Allocates an integer point vector (i.e., one-dimensional array) from *nl* to *nh*. If unable to set the necessary memory aside or if the input parameters are improperly set, then a null pointer is returned (defined as _FAIL).

| Interface | *int \*ivector( int nl, int nh )* | |
|---|---|---|
| Type | Variable | Data Description |
| *Input* | *nl* | Lower subscript range. *nl* must be greater than or equal to 0. |
| | *nh* | Upper subscript range. *nh* must be greater than or equal to *nl*. |
| *Output* | *(None)* | |
| *Modified* | *(None)* | |
| *Return* | Pointer to an integer point vector or _FAIL if unable to allocate memory. | |

5.1.5.7 MAS Enumerations

5.1.5.7.1 MAS Public Enumerations

*5.1.5.7.1.1 mat_alloc_errors*

Below are listed all status codes that denote the errors that can occur for the functions of the MAS.

| Enumeration | Value | Description |
|---|---|---|
| _PASS | 1 | No error occurred. |
| _FAIL | 0 | Insufficient resources to allocate array(s) or input error. |
| _BadInput | -1 | Input parameter(s) improperly specified. |

5.1.5.8 MAS Macros and Definitions

5.1.5.8.1 Public MAS Macros

| Macro | Description |
|---|---|
| *SQR( a )* | Squares *a* and typecasts the result as a float. |

5.1.5.8.2 Private MAS Definitions

| Definition | Value | Description |
|---|---|---|
| *NR_END* | 1 | Memory storage offset. |
| *FREE_ARG* | char* | Memory allocation pointer. |

5.2 Decomposition and Detailed Design

The decomposition and detailed description that follows is written in a form that best conveys the nature of the ANSI C programming language in which the MNS was written. The decomposition is carried out so that functions that are not part of the parent file are shaded. In these cases, the file is noted to the right. Standard libraries are not included in the decomposition. If a decomposition is not present, then there are no subordinates to the function.

5.2.1 Field Matching Software Description

5.2.1.1 FieldMatch_v1()

The purpose of this function is to convert the magnetic problem into the proper quadratic problem. Appendix 6.1 details this process in greater detail. Briefly stated, the currents are calculated by minimizing the RMS current subject to the constraint that the desired magnetic field be generated. The solution for the currents is plugged back into the module Calc_B() to check that the resulting magnetic field matches the desired magnetic field within the field tolerances. If the magnetic field strength is very small in magnitude (<_BMIN_EPS), then a zero current solution is returned.

Figure 16 FieldMatch_v1() *Subordinates*

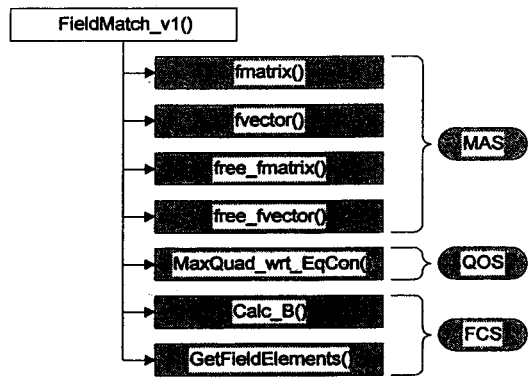

Figure 17 Flowchart of FieldMatch_v1()

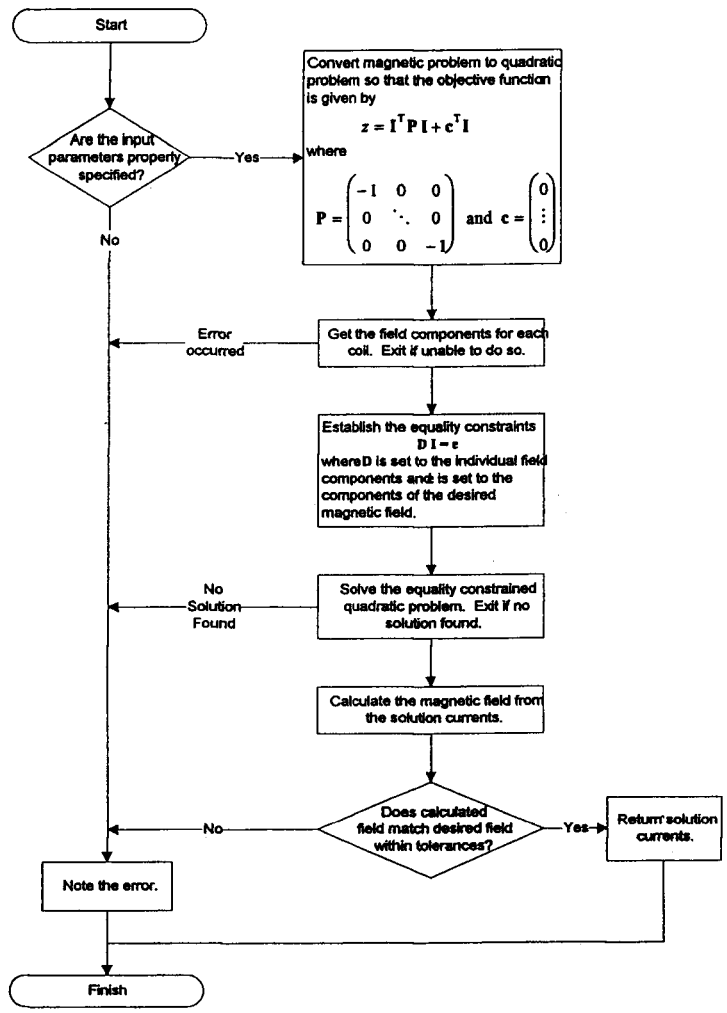

5.2.1.2 SetMaxBAng()

The maximum angular variation between the desired and generated magnetic field orientation has a default value of DEF_MAX_ANG_DEV defined in the FMS. This value must be between 0 and 180, having units of degrees.

5.2.1.3 SetMaxBTol()

If the fractional tolerance is defined as $f$, then the lower and upper limits to the generated field strength are $B(1-f)$ and $B(1+f)$, respectively. The maximum fractional variation has a default value of DEF_BMAG_TOL defined in the FMS. This value must be greater than FLT_EPSILON defined in float.h.

5.2.1.4 SetMaxCurrent()

The maximum current magnitude has a default value (A) of DEF_MAX_CURRENT. For example, if the maximum current magnitude for the six coils (i.e., $I[1..6]$) is DEF_MAX_CURRENT, then
$- \text{DEF\_MAX\_CURRENT} \le I[1..6] \le \text{DEF\_MAX\_CURRENT}$.

5.2.2 Quadratic Optimization Software Description

5.2.2.1 CalcSymmetricMatrix()

This function only has meaning to those matrices that describe a quadratic function since the symmetric form yields the same quadratic function as the non-symmetric form. For example, the equation $$z = 4x_1^2 + 5x_2^2 + 8x_1 x_2 = \{x_1 \ \ x_2\} \begin{bmatrix} 4 & 8 \\ 0 & 5 \end{bmatrix} \begin{Bmatrix} x_1 \\ x_2 \end{Bmatrix}$$

has the same form if $\begin{bmatrix} 4 & 8 \\ 0 & 5 \end{bmatrix}$ is replaced by its symmetric form $\begin{bmatrix} 4 & 4 \\ 4 & 5 \end{bmatrix}$. Writing a matrix in the symmetric form is useful (and often necessary) in finding the solution to a quadratic problem.

5.2.2.2 ImproveLinSoln()

See *Press et al.* (pp. 55-58) for a detailed accounting of iterative improvement to a linear solution.

5.2.2.3 LUBackSub()

See *Press et al.* (pp. 43-50) for a detailed accounting of LU back substitution.

Figure 18 LUBackSub() Subordinates

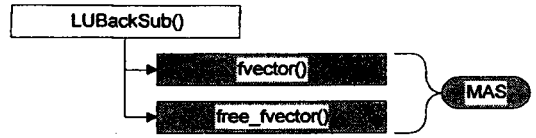

5.2.2.4 LUDecomp()

See *Press et al.* (pp. 43-50) for a detailed accounting of LU decomposition.

Figure 19 LUDecomp() Subordinates

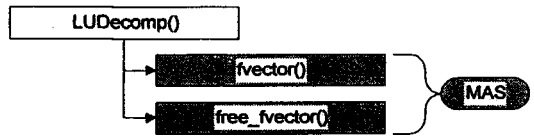

5.2.2.5 LUSolve()

See *Press et al.* (pp. 43-50) for a detailed accounting of LU decomposition and back substitution.

Figure 20 LUSolve() Subordinates

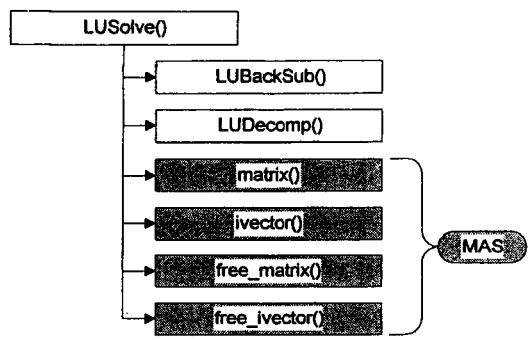

5.2.2.6 Mat_X_Vec()

(No additional comments.)

5.2.2.7 MaxQuad_wrt_EqCon()

The problem pertaining to maximizing the quadratic problem $z = c^T x + x^T P x$ subject to equality constraints of the form $Dx = e$ is addressed in Appendix 6.1.

Figure 21 MaxQuad_wrt_EqCon() Subordinates

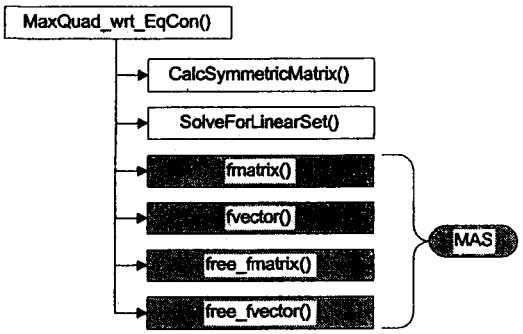

5.2.2.8 SolveForLinearSet()

This function first attempts to find the solution of $A x = b$, where A is a $n \times n$ square matrix, by LU decomposition. If unable to do so, SVD is used to generate the solution. While the two methods generate the same results in all but the singular cases, SVD takes, roughly, an order or magnitude longer to find the solution.

Figure 22 SolveForLinearSet() Subordinates

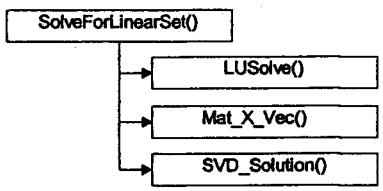

5.2.2.9 SVD_BackSub()

SVD back substitution is thoroughly described in *Press et al.* pp. 59-70.

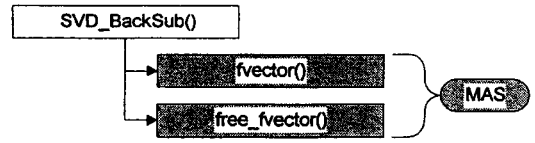

5.2.2.10 SVD_Solution()

SVD is thoroughly described in *Press et al.* pp. 59-70. This function combines the elements of the individual components of SVD so that the user may pass in the matrices $A[1..m][1..n]$ and $b[1..m]$ without internal modification and be presented with the solution $x[1..n]$ on return.

Figure 23 SVD_Solution() Subordinates

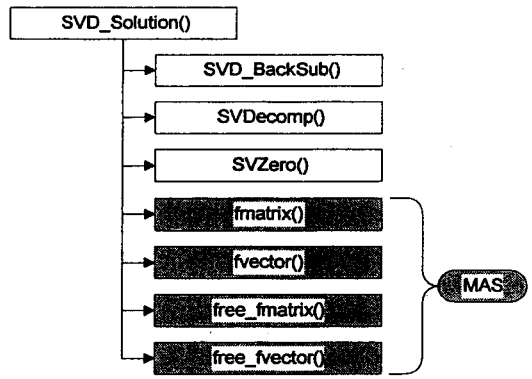

5.2.2.11 SVDecomp()

SVD is thoroughly described in *Press et al.* pp. 59-70.

Figure 24 SVDecomp() Subordinates

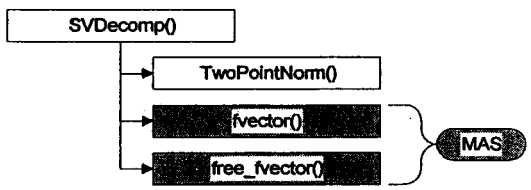

5.2.2.12 SVZero()

It is sometimes necessary to zero the diagonal elements of the w matrix of the SVD (i.e., represented by the column matrix $w[1..n]$) in order to generate reliable solutions. This is discussed in *Press et al.* pp. 63-64.

5.2.2.13 TwoPointNorm()

Because the square operators in $\sqrt{a^2 + b^2}$, under- and over-flow can easily occur. To account for this, the norm is computed via $|a|\sqrt{1+(b/a)^2}$ if $a > b$. Otherwise, the norm is found from $|b|\sqrt{1+(a/b)^2}$.

5.2.3 Field Computation Software Description

5.2.3.1 Calc_B()

This function superposes the individual magnetic fields for each coil after the field information is calculated with CalcFieldData(). If the magnetic field is denoted by B then it follows that $\mathbf{B} = \sum_{n=1}^{6} \mathbf{B}_n$ where the subscript $n$ denotes the six coils. Since the magnetic field is linear with respect to the magnetic field, then the total magnetic field can be written as $\mathbf{B} = \sum_{n=1}^{6} \mathbf{b}_n I_n$. See appendices 6.2 and 6.3 for a detailed accounting of the calculation and superposition of the magnetic field and the field partials.

Figure 25 Calc_B() Subordinates

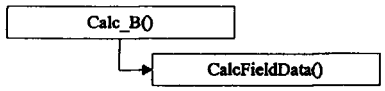

5.2.3.2 Calc_d2B()

This function superposes the individual magnetic field second derivatives for each coil after the field information is calculated with CalcFieldData(). If the magnetic field is denoted by B then it follows that 18 second-order derivatives are given by $\dfrac{\partial^2 \mathbf{B}}{\partial x_i \partial x_j} = \sum_{n=1}^{6} \dfrac{\partial^2 \mathbf{B}_n}{\partial x_i \partial x_j}$ where the subscript $n$ denotes the six coils and the $i$ and $j$ indices denote the $x$, $y$, and $z$ components. Nine additional second-order derivatives result from the partials of the field magnitude (includes first-order derivative information). See appendices 6.2 and 6.3 for a detailed accounting of the calculation and superposition of the magnetic field and the field partials.

Figure 26 Calc_d2B() Subordinates

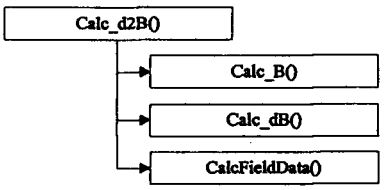

5.2.3.3 Calc_dB()

This function superposes the individual magnetic field first derivatives for each coil after the field information is calculated with CalcFieldData(). If the magnetic field is denoted by B then it follows that 9 first-order derivatives are given by $\dfrac{\partial \mathbf{B}}{\partial x_i} = \sum_{n=1}^{6} \dfrac{\partial \mathbf{B}_n}{\partial x_i}$ where the subscript $n$ denotes the six coils and the $i$ index denotes the $x$, $y$, and $z$ components. Three additional first-order derivatives result from the partials of the field magnitude (includes magnetic field information). See appendices 6.2 and 6.3 for a detailed accounting of the calculation and superposition of the magnetic field and the field partials.

Figure 27 Calc_dB() Subordinates

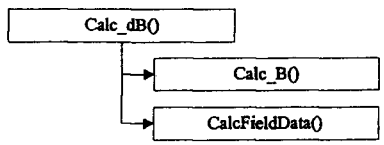

5.2.3.4 Calc_F()

This function combines the individual magnetic field first derivatives for each coil and the a permanent magnetic moment MDV [after the field information is calculated with CalcFieldData()] in order to generate the force on the MDV. Since the moment is permanent, the force is given by $F_i = \frac{m}{B}\mathbf{B}^T \frac{\partial \mathbf{B}}{\partial x_i}$ where the $i$ index denotes the $x$, $y$, and $z$ components. See appendices 6.2 and 6.3 for a detailed accounting of the calculation and superposition of the magnetic field and the field partials.

Figure 28 Calc_F() Subordinates

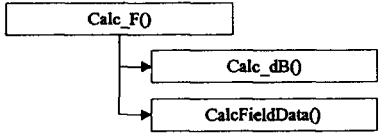

5.2.3.5 Calc_PermF()

This function combines the individual magnetic field first derivatives for each coil and the a permeable magnetic moment MDV [after the field information is calculated with CalcFieldData()] in order to generate the force on the MDV. Since the moment is permeable, the force is given by $F_i = \left(\frac{m_{sat}}{B}\right)\mathbf{B}^T \frac{\partial \mathbf{B}}{\partial x_i}$ if the field is at or greater than the saturation field ($m_{sat}$ is the saturated magnetic moment) where the $i$ index denotes the $x$, $y$, and $z$ components. If the field is less than the saturation field, then the force is given by $F_i = \left(\frac{m_{sat}}{B_{sat}}\right)\mathbf{B}^T \frac{\partial \mathbf{B}}{\partial x_i}$. See appendices 6.2 and 6.3 for a detailed accounting of the calculation and superposition of the magnetic field and the field partials.

Figure 29 Calc_F() Subordinates

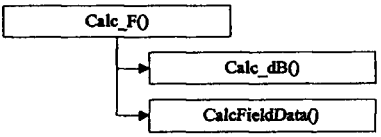

5.2.3.6 CalcBForCoil()

The field information (through second-order) is calculated for the specified coil by examining the data plane for the respective coil and then interpolating the field (and derivatives) at the desired point. This is done by a spline interpolation. Once calculated, the field data is scaled to the specified current. The transformations back into helmet coordinates are handles also by this function. Appendix 6.3 serves as a sufficient reference to this process.

Figure 30 CalcBForCoil() Subordinates

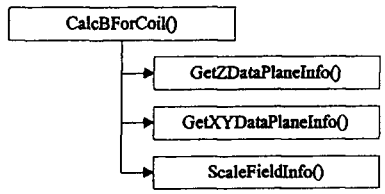

5.2.3.7 CalcFieldData()

This function calculates all the field information for each coil and stores the data internally each time a position is passed. If the position was the same as the previous call (within the floating point limit), then the previous results are returned without additional computation. The manner in which the individual magnetic fields are calculated is detailed in Appendix 6.2.

Figure 31 CalcFieldData() Subordinates

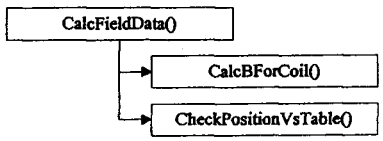

5.2.3.8 CheckPositionVsTable()

This function is necessary in that the data tables possessing the magnetic field information for the two coil types represent a limited set of values. If request are made outside this range of the tables, an error must be returned to the user. The present model also has discrepancies at the boundary data points due to the fact that the first derivatives are not included into the table at those points. Instead, a natural spline is assumed (which is not correct). The problem is resolved by simply restricting the data tables to reliable ranges of data that does not include the boundary data points.

5.2.3.9 DeinitArrays()

An internal flag is set so that if DeinitArrays() is called without InitArrays() being called, hen nothing is done.

Figure 32 DeinitArrays() Subordinates

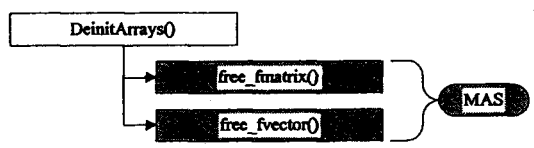

5.2.3.10 GetFieldElements()

This function is useful when the internal field information needs to be accessed but not modified.

Figure 33 GetFieldElements() Subordinates

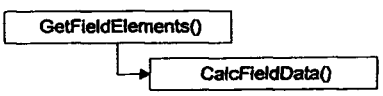

5.2.3.11 GetXYDataPlaneInfo()

The field information (through second-order) is calculated for the X or Y coils by examining the data plane for the respective coil and then interpolating the field (and derivatives) at the desired point. This is done by a two-dimensional spline interpolation. Appendix 6.2 serves as a sufficient reference to this process.

Figure 34 GetXYDataPlaneInfo() Subordinates

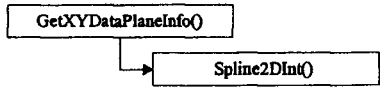

5.2.3.12 GetZDataPlaneInfo()

The field information (through second-order) is calculated for the Z coils by examining the data plane for the respective coil and then interpolating the field (and derivatives) at the desired point. This is done by a two-dimensional spline interpolation. Appendix 6.2 serves as a sufficient reference to this process.

Figure 35 GetZDataPlaneInfo() Subordinates

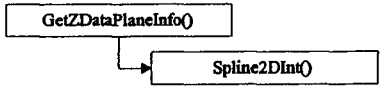

5.2.3.13 InitArrays()

Upon initialization, the coil array file detailing the locations of the coil midplanes with resoect to helmet coordinates is loaded, identified as DEF_COIL_ARRAY_PATH in the FCS header file. Also contained in the file are the names and paths of the magnetic field data files for the coils and the respective sizes of the data tables. Once loaded, the memory is allocated and the field data for each coil is loaded into memory. Lastly, the two-dimensional splines are calculated for each file so the data may be easily interpolated.

Figure 36 InitArrays() Subordinates

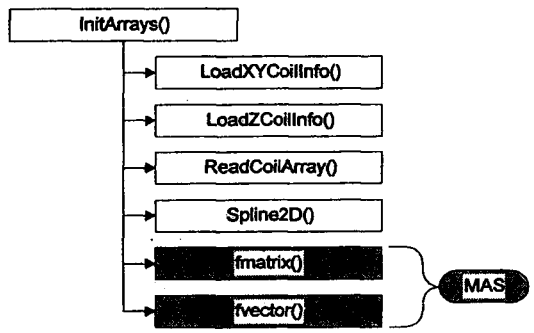

5.2.3.14 LoadXYCoilInfo()

The data table for the X and Y coils is loaded into memory [which has already been allocated with the call to InitArrays()] with the field data being scaled by the reference current for which the table was created.

5.2.3.15 LoadZCoilInfo()

The data table for the Z coils is loaded into memory [which has already been allocated with the call to InitArrays()] with the field data being scaled by the reference current for which the table was created.

5.2.3.16 ReadCoilArray()

The names for the data file for the X and Y coils and the data file for the Z coils in addition to the parameters of each set of tabulated data are obtained from this file. Also included are the coil midplane locations with respect to helmet coordinates. The information regarding the data tables (i.e., the number and order of the data points, reference current, etc.) is obtained by loading the name of the respective data file contained in the coil array file. After the midplane locations are saved, the coil array file is closed and the magnetic field data files are opened. Only the header files are read, which contains all the pertinent information on the respective coil's magnetic field. This information is stored and returned on exit.

5.2.3.17 ReportPathAssignment()

(No additional comments.)

5.2.3.18 ScaleFieldInfo()

(No additional comments.)

5.2.3.19 SetFilePath()

(No additional comments.)

5.2.3.20 Spline1D()

The one-dimensional cubic splines used by the FMS are covered in detail in *Press et al.* pp. 113-116.

5.2.3.21 Spline1DInt()

Interpolation of the one-dimensional cubic splines used by the FMS are covered in detail in *Press et al.* pp. 113-116.

5.2.3.22 Spline2D()

The two-dimensional cubic splines used by the FMS are covered in detail in *Press et al.* pp. 123-128.

5.2.3.23 Spline2DInt()

Interpolation of the two-dimensional cubic splines used by the FMS are covered in detail in *Press et al.* pp. 123-128.

5.2.4 Field Generation Software Description

5.2.4.1 DefineCoilArray()

This function requests the following information (in order):

- Name of the coil array file which possesses the locations of the coil midplanes with respect to helmet coordinates.
- Name of the file possessing the tabulated magnetic field data for the X and Y coils (which are identical).
- Name of the file possessing the tabulated magnetic field data for the Z coils (which are identical).
- The three-dimensional coordinates (in helmet coordinates) of the midplanes for the XA, XB, YA, YB, ZA, and ZB coils (requested in this order). All positions indicated in mm.

The information is written to the coil array file specified by the user in the following format:

- Name of the coil array file.
- Version of the software.
- XY magnetic field data table.
- Z magnetic field data table.
- Date file was created.
- Brief explanation in header.
- Index and locations of the coils in helmet coordinates (m).

The following is an example:

*File: coil_array.txt*
*Version: 1.0*
*X & Y Coil Data File: full_xy.txt*
*Z Coil Data File: full_z.txt*
*Date: 8/12/96 (13:41:31)*
*Data is written for the coil indices 1-6 which denote the*
*XA, XB, YA, YB, ZA, ZB coils. The three following components*
*correspond to the midplane location of each coil in meters*

*1:  0.263700   0.000000   0.000000*
*2: -0.263700   0.000000   0.000000*
*3:  0.000000   0.263700   0.000000*
*4:  0.000000  -0.263700   0.000000*
*5:  0.000000   0.000000   0.179000*
*6:  0.000000   0.000000  -0.170500*

The subordinates are given in the figure below.

Figure 37 DefineCoilArray() Subordinates

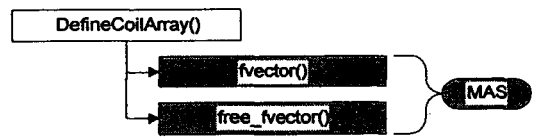

5.2.4.2 FieldGenExe()

Information regarding the physical properties of the magnetic coil is requested separate from the integration parameters (using Romberg's method) used in constructing the magnetic field data tables. The coil's physical parameters are requested first [by a call to SetCoilParameters()]. They are entered in the following order:

- Coil's outer radius (mm).
- Coil's inner radius (mm).
- Coil's thickness (mm).
- Number of windings around coil.
- Coil's reference current (A).

The integration parameters are given the following default values

The fractional accuracy (EPS): 1.0e-2
Total number of steps in the integration (JMAX): 10
K value of Romberg's method: 5
Maximum integration iterations: 1000
Number of approximating filaments: 150 and are listed above the menu. The user may change any of the parameters through the menu selection which consist of the following:

(1) Change Outer Radius
(2) Change Inner Radius
(3) Change Coil Thickness
(4) Change Number of Coil Windings
(5) Change Reference Current
(6) Change EPS Value
(7) Change JMAX Value
(8) Change K Value
(9) Change the Maximum Iterations
(10) Change the Number of Approximating Filaments
(11) Accept Entries and Generate File
(12) Exit With all parameters set to their desired value, the table is generated by the function GenerateFile(). For information regarding Romberg integration, see *Press et al.* pp. 131-141. For more information of the construction of the magnetic field data files, see Appendix 6.2. The subordinates are given in the figure below.

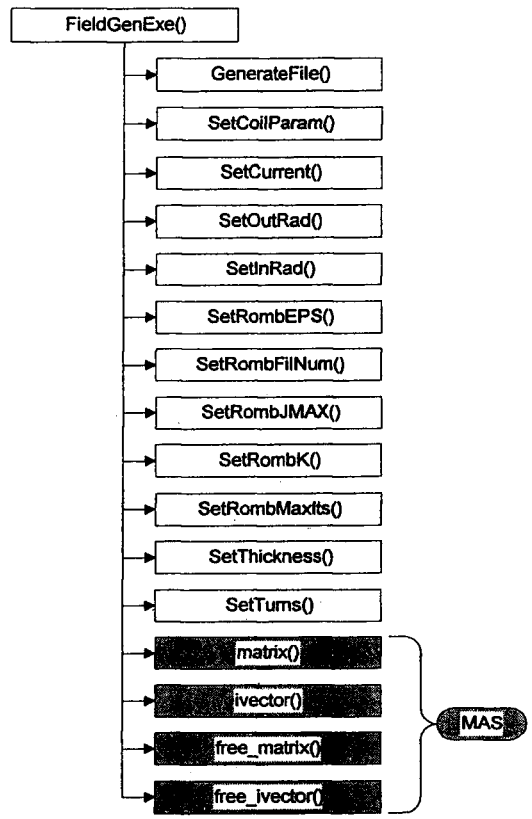

Figure 38 FieldGenExe() Subordinates

5.2.4.3 func_bl()

For more information of the calculation of the axial current, see Appendix 6.2.

5.2.4.4 func_br()

For more information of the calculation of the radial current, see Appendix 6.2.

5.2.4.5 GenerateFile()

This sub-function of the FieldGenExe() is responsible for generating the field data for the magnetic coil. A call to this function results in the following user request regarding the construction of the table:

- Starting L distance (mm) which is the beginning axial distance from the coil midplane.
- Ending L distance (mm) which is the ending axial distance from the coil midplane.
- L spacing (mm). This corresponds to the tabulation in the axial distance. The tabulation begins at the beginning L distance and continues the increments until the ending L distance is not passed.
- Maximum R distance (mm) (i.e., the outer radial distance in the table). The beginning radial distance is automatically assumed to be set to 0.
- R spacing (mm). This corresponds to the tabulation in the radial distance. The tabulation begins at 0 and continues the increments until the ending R distance is not passed.

The field information is calculated at the tabulated points for the specified coil parameters and integration parameters. The information is written as follows (in order):

- The file's name.
- The version of the field generating program.

- The date and time the file was created.
- The outer radius (m).
- The inner radius (m).
- The coil width (m).
- The number of coil windings.
- The reference current at which the file was generated (A).
- The number of approximating filaments in the L (axial) direction.
- The number of approximating filaments in the R (radial) direction.
- Starting tabulation in L (axial distance) (m).
- Ending tabulation in L (axial distance) (m).
- Starting tabulation in R (radial distance) (m).
- Tabulation in L (axial direction) (m).
- Tabulation in R (radial direction) (m).
- Field information written according to the beginning L distance to the ending axial distance (without surpassing the ending L distance). For each L entry, the R entries are listed with the computed radial and axial magnetic fields (T) at the reference current. Thus, the information is written as $$\begin{aligned} &\{L\} \\ &\{R\}, & B_r(R,L), & \quad B_l(R,L) \\ &\{R+\Delta R\}, & B_r(R+\Delta R,L), & \quad B_l(R+\Delta R,L) \\ &\quad \vdots & \vdots & \quad \vdots \\ &\{R+n_R \Delta R\}, & B_r(R+n_R \Delta R, L) & \quad B_l(R+n_R \Delta R, L) \\ &\{L+\Delta L\} \\ &\{R\}, & B_r(R+\Delta R, L+\Delta L), & \quad B_l(R+\Delta R, L+\Delta L) \\ &\quad \vdots & \vdots & \quad \vdots \end{aligned}$$

where $\Delta R$ and $\Delta L$ are the radial and axial, respectively, tabulations and where $n_R$ denotes the number of tabulations in R. The following is an example:

*full_xy.txt*
*Version: 1.0*
*Date: 8/16/96 (16:5:29)*
*Outer Radius(m): 0.186000*
*Inner Radius(m): 0.140000*
*Width of coil(m): 0.070100*
*Coil Windings: 6642*
*Reference Current(A): 1.000000*
*Number of filaments in L direction: 15*
*Number of filaments in R direction: 10*
*Starting Tabulated L(m): 0.000000*
*Ending Tabulated L(m): 0.530000*
*Ending Tabulated R(m): 0.320000*
*Tabulation in L(m): 0.010000*
*Tabulation in R(m): 0.010000*
*0.000000*
*0.000000,0.000000,0.025181*
*0.010000,0.000000,0.025248*
.
.

For more information of the construction of the magnetic field data files, see Appendix 6.2. The subordinates are given by the figure below.

Figure 39 GenerateFile() Subordinates

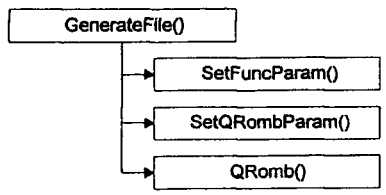

5.2.4.6 NthTrapStage()
The trapezoidal rule is detailed thoroughly in *Press et al.* pp. 131-137.

5.2.4.7 PolyInt()
Polynomial interpolation is detailed thoroughly in *Press et al.* pp. 105-110.

5.2.4.8 QRomb()
Romberg integration is detailed thoroughly in *Press et al.* pp. 131-141.

Figure 40 QRomb() Subordinates

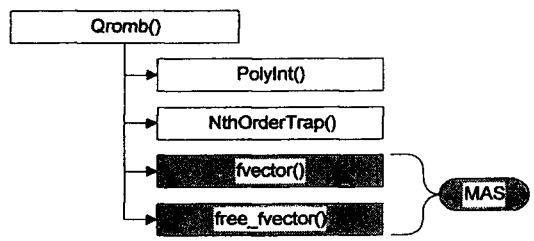

5.2.4.9 SetCoilParam()
The coil's physical parameters are requested in the following order:
- Coil's outer radius (mm).
- Coil's inner radius (mm).
- Coil's thickness (mm).
- Number of windings around coil.
- Coil's reference current (A).

Figure 41 SetCoilParam() Subordinates

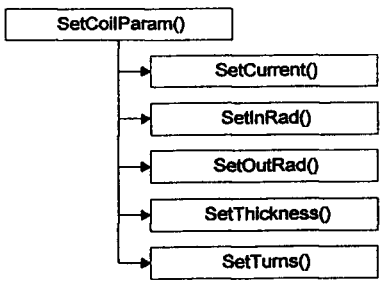

5.2.4.10 SetCurrent()
(No additional comments.)

5.2.4.11 SetFuncParam()
(No additional comments.)

5.2.4.12 SetInRad()
(No additional comments.)

5.2.4.13 SetOutRad()
(No additional comments.)

5.2.4.14 SetRombParam()
The Romberg integration parameters are detailed thoroughly in *Press et al.* pp. 131-141.

5.2.4.15 SetRombEPS()
The Romberg fractional accuracy is detailed thoroughly in *Press et al.* pp. 131-141.

5.2.4.16 SetRombFilNum()
The approximating filaments are useful in that they can greatly reduce the time necessary for generating the data table without loss in accuracy. For more information of the construction of the magnetic field data files using approximating filaments for the coil windings, see Appendix 6.2.

5.2.4.17 SetRombJMAX()
The Romberg step number is detailed thoroughly in *Press et al.* pp. 131-141.

5.2.4.18 SetRombK()
The Romberg K value is detailed thoroughly in *Press et al.* pp. 131-141.

5.2.4.19 SetRombMaxIts()
The number of iterations that the Romberg integration function is allowed to loop over is limited. This ensures that the integration does not request trapezoidal sub-divisions that violate the maximum value of a long integer (at which point the function can fail). The value is changeable since lesser iterations take less computation time while, in most cases, yielding accurate results.

5.2.4.20 SetThickness()
(No additional comments.)

5.2.4.21 SetTurns()
(No additional comments.)

5.2.4.22 ShowCoilParam()
The display offers the following information on the physical properties of the coil:
- Outer radius of coil (mm).
- Inner radius of coil (mm).
- Coil width (mm).
- Number of coil windings.
- Reference current to generate magnetic field data table (A).

5.2.4.23 ShowMenu()

The display offers the following information on the menu options for FielfGenExe():

(1) Change Outer Radius
(2) Change Inner Radius
(3) Change Coil Thickness
(4) Change Number of Coil Windings
(5) Change Reference Current
(6) Change EPS Value
(7) Change JMAX Value
(8) Change K Value
(9) Change the Maximum Iterations
(10) Change the Number of Approximating Filaments
(11) Accept Entries and Generate File
(12) Exit

5.2.4.24 Version()

(No additional comments.)

5.2.5 Matrix Allocation Software Description

5.2.5.1 fmatrix()

Setting a float matrix (i.e., a two-dimensional array) can best be explained by example:

We first declare the variable $a$ according to

*float \*\*a ;*

If we wish to allocate the matrix $a = \begin{pmatrix} a_{2,3} & a_{2,4} & a_{2,5} & a_{2,6} \\ a_{3,3} & a_{3,4} & a_{3,5} & a_{3,6} \\ a_{4,3} & a_{4,4} & a_{4,5} & a_{4,6} \end{pmatrix}$, then we write

*a = fmatrix( 2, 4, 3, 6 ) ;*

To check if an allocation or input error, we check for a null pointer passed as _FAIL (defined in header).

When $a$ is no longer needed, we deallocate $a$ with the command

*free_fmatrix( a, 2, 4, 3, 6 ) ;*

5.2.5.2 free_fmatrix()

See the detailed notes on fmatrix() (5.2.5.1).

5.2.5.3 free_fvector()

See the detailed notes on fvector() (5.2.5.5).

5.2.5.4 free_ivector()

See the detailed notes on ivector() (5.2.5.6).

5.2.5.5 fvector()

Setting a float column matrix (i.e., a one-dimensional array or "vector") can best be explained by example:

We first declare the variable $a$ according to

*float \*a ;*

If we wish to allocate the vector $a^T = \begin{pmatrix} a_3 & a_4 & a_5 & a_6 \end{pmatrix}$, then we write

*a = fvector( 3, 6 ) ;*

To check if an allocation or input error, we check for a null pointer passed as _FAIL (defined in header).

When $a$ is no longer needed, we deallocate $a$ with the command

*free_fvector( a, 3, 6 ) ;*

5.2.5.6 ivector()

Setting a integer column matrix (i.e., a one-dimensional array or "vector") can best be explained by example:

We first declare the variable $a$ according to

*int \*a ;*

CERTIFICATE OF CORRECTION (continued)

U.S. Pat. No. 6,015,414

If we wish to allocate the vector $\mathbf{a}^T = \begin{pmatrix} a_3 & a_4 & a_5 & a_6 \end{pmatrix}$, then we write

*a = ivector( 3, 6 ) ;*

To check if an allocation or input error, we check for a null pointer passed as _FAIL (defined in header).

When *a* is no longer needed, we deallocate *a* with the command

*free_ivector( a, 3, 6 ) ;*

APPENDIX "B"

Quadratic Optimizations Pertaining to Current Solutions for Magnetic Field Sources

F. M. Creighton

Stereotaxis Inc., 1 Barnes Hospital Plaza, 5$^{th}$ floor Rand-Johnson Bld., St. Louis, MO 63110

G. T. Munger

Department of Material Science and Engineering, University of Virginia, Charlottesville, VA 22903

R. C. Ritter

Department of Physics, University of Virginia, Charlottesville, VA 22903

( Received

*Abstract-* This paper discusses optimization theory of multi-variable quadratic functions subject to equality and inequality constraints and the application of such solutions to magnetostatics. The techniques pertaining to solving constrained general objective functions are presented as a primer to the work on quadratic forms. Lagrange and Kuhn-Tucker theories are discussed in this regard. Current and force metrics are offered as possible quadratic objective functions for magnetomotive based, quasi-static systems. As an example, the magnetic problem associated with the Magnetic Stereotaxis System ( a new neurosurgical tool developed by Stereotaxis, Inc., the University of Virginia, and Wang NMR) is presented and solved.

I.  Introduction

Many techniques, both analytical and numerical, have been developed to aid in minimizing and maximizing a function dependent on one or more independent variables. Generally speaking, it is desirable to identify a global maximum and/or a global minimum by analytical means given that identification of a function's global extrema via numerical means are relatively difficult.[1] The optimization problem is further complicated when *a priori* limitations on the allowed values of the independent variables are imposed. Pursuit of an analytical solution for such "constrained optimizations" is aided by Lagrange multiplier theory when equality constraints are imposed (i.e., in the form of $g(\mathbf{x}) = 0$). If inequality constraints (i.e., $d(\mathbf{x}) \geq 0$) are also introduced, then Kuhn-Tucker theory is useful in identifying extrema. As one may guess, both theories in no way guarantee the existence of an analytical solution for all problems. If an analytical form is not easily obtained, numerical tools are often useful in identifying local extrema so that, given a well-behaved function and a sufficient sampling of the variables, a global minimum and maximum may be found. However, if we, for the present purposes, restrict ourselves to a properly posed quadratic objective function which is either unconstrained or subject to strictly linear constraints, we find that an analytical form for the optimum is obtainable.

A benefit of quadratic object functions is their immediate application to magnetostatic problems in which the magnetic sources consist of multiple current-dependent magneto-motive "actuators" whose fields remain static or are slowly varying. The Magnetic Stereotaxis System (MSS), a multi-coil neurosurgical system currently being developed to magnetically direct implants through the brain via nonlinear paths, is one such system for which the following body of work was originally developed. In this vein, the magnetic problem pertaining to the MSS is magnetostatics are not limited to that of the MSS (for which it is especially well suited). For instance, multi-axis magnetic bearings and magnetic suspensions are but two fields that could potentially profit from such applications.

II. DISCUSSION OF GENERAL MULTIDIMENSIONAL OPTIMIZATIONS

A. General Remarks on the Unconstrained Problem

The following is a relatively brief summary of theorems and applications of multi-variable optimizations of unconstrained and constrained objective functions. For detailed discussion on these topics, the reader is referred to more comprehensive works.[2-7] Generally speaking, optimizations involve identifying the extrema of an objective function $f(\mathbf{x})$ over the space $\mathbf{x} \in U$ where U is the domain of $f(\mathbf{x})$. If $f(\mathbf{x})$ is differentiable over the $n$-dimensional space defined by $\mathbf{x}$ (i.e., $\mathbf{x} \in \Re^n$), and $\mathbf{x}_o$ is a local extremum, then $\mathbf{x}_o$ is identified as a critical point of $f(\mathbf{x})$ if and only if $$\frac{\partial f}{\partial x_i}(\mathbf{x}_o) = 0 \quad (i = 1, \ldots, n) \quad \text{or} \quad \nabla f(\mathbf{x}_o) = 0 \tag{1}$$

In order to distinguish the critical points of $f(\mathbf{x})$ as local maxima, local minima, or saddle points, the Hessian of $f(\mathbf{x})$ at $\mathbf{x}_o$ is constructed.[4,8] If the domain of $f(\mathbf{x})$ is a member of the space defined by the $n$-dimensional vector $\mathbf{x}$ and maps to real space (written as $f: U \subset \Re^n \rightarrow \Re, \mathbf{x}_o \in U$) where the first- and second-order derivatives of $f(\mathbf{x})$ are continuous, Taylor's theorem may be applied to $f(\mathbf{x}_o)$ so that $$f(\mathbf{x}_o + \mathbf{h}) - f(\mathbf{x}_o) = Hf(\mathbf{x}_o)(\mathbf{h}) + R(\mathbf{h}, \mathbf{x}_o) \tag{2}$$

In Eq. (2), $Hf(\mathbf{x}_o)$ is defined as the Hessian and is given by $$Hf(\mathbf{x}_o)(\mathbf{h}) = \frac{1}{2}\sum_{i,j=1}^{n} h_i\, H(\mathbf{x}_o)_{ij}\, h_j = \frac{1}{2}\mathbf{h}^T H(\mathbf{x}_o)\mathbf{h} \tag{3}$$

where the elements of H are denoted by $$H(\mathbf{x}_o)_{ij} = \frac{\partial^2 f}{\partial x_i\, \partial x_j}(\mathbf{x}_o) \quad (i,j = 1,\ldots,n) \tag{4}$$

and where the remainder $R(\mathbf{h},\mathbf{x}_o)$ has the property $$\frac{R(\mathbf{h},\mathbf{x}_o)}{\|\mathbf{h}\|^2} \to 0 \tag{5}$$

as $\mathbf{h} \to 0$. Assuming that $\mathbf{x}_o$ is a critical point of $f(\mathbf{x})$, the Hessian is positive definite [i.e., the critical point $\mathbf{x}_o$ is a relative minimum of $f(\mathbf{x})$] if the determinants of the principle submatrices of H are all greater than zero. Mathematically speaking, this is written as $$\left|H_{rr}(\mathbf{x}_o)\right| > 0 \quad (r = 1,\ldots,n) \tag{6}$$

where $H_{rr}$ is obtained by retaining only the first $r$ rows and $r$ columns of H. For negative definiteness [i.e., $\mathbf{x}_o$ is a relative maximum of $f(\mathbf{x})$], the determinants of the principle submatrices of H will alternate between strictly positive and negative values:[9]

$$(-1)^r \left|H_{rr}(\mathbf{x}_o)\right| > 0 \quad (r = 1,\ldots,n) \tag{7}$$

If the determinants of the principal submatrices are not all zero and H is neither positive nor negative definite, the critical point is considered to be a saddle point. An extension to positive semidefiniteness and negative semidefiniteness can be made without loss of generality.[10] For those cases in which the determinant of the principal submatrices are all equal to zero, a case-bycase investigation is required.[4,5] These more advanced cases will not be addressed in this publication.

B. Functions Subject to *m* Equality Constraints

We now consider cases in which an optimization is to be performed where constraints are imposed upon the objective function $f(\mathbf{x})$. A useful method for finding the individual extrema for this problem involves the introduction of multipliers via the Lagrange Multiplier theorem, which is stated as follows:[3-5]

*Let the domains of the smooth functions $f(\mathbf{x})$ and $g_i(\mathbf{x})$ $(i=1,\ldots,m, m<n)$ be subsets of n-dimensional real space $\Re^n$ where both $f(\mathbf{x})$ and $g_i(\mathbf{x})$ assign values to $\Re$. Assuming $\mathbf{x}_o$ is contained in the subset of $f(\mathbf{x})$ and $g_i(\mathbf{x})$ where $g_i(\mathbf{x}_o)=0$ and where the set $\nabla g_1(\mathbf{x}_o),\ldots,\nabla g_m(\mathbf{x}_o)$ is linearly independent, if $f(\mathbf{x})$ is restricted to and has a maximum or minimum on the surface set of points for which $g_i(\mathbf{x}_o)=0$ at $\mathbf{x}_o$, then there exists a set of real numbers $\lambda$ (termed "Lagrange multipliers") that obey the relationship*

$$\nabla f(\mathbf{x}_o) = -\sum_{i=1}^{m} \lambda_i \nabla g_i(\mathbf{x}_o) = -\lambda^T \nabla \mathbf{g}(\mathbf{x}_o). \tag{8}$$

It is often convenient to write the above theorem in terms of the "Lagrangian" function $\mathcal{L}$. Given that $\mathcal{L}$ is defined according to $$\mathcal{L} = f(\mathbf{x}) + \sum_{i=1}^{m} \lambda_i g_i(\mathbf{x}) = f(\mathbf{x}) + \lambda^T \mathbf{g}(\mathbf{x}) \tag{9}$$

then Eq. (8) may be written so that at $\mathbf{x} = \mathbf{x}_o$ $$\frac{\partial \mathbf{L}}{\partial x_i}(\mathbf{x}_o) = 0 \ (i = 1, \ldots, n) \text{ and } \frac{\partial \mathbf{L}}{\partial \lambda_j}(\mathbf{x}_o) = 0 \ (j = 1, \ldots, m) \tag{10}$$

and hence $$\left. \begin{array}{l} \frac{\partial f}{\partial x_i}(\mathbf{x}_o) + \sum_{i=1}^{m} \lambda_i \frac{\partial g_i}{\partial x_i}(\mathbf{x}_o) = 0 \ (i = 1, \ldots, n) \\ g_j(\mathbf{x}_o) = 0 \ (j = 1, \ldots, m) \end{array} \right\} \text{ or } \left. \begin{array}{l} \nabla f(\mathbf{x}_o) + \lambda^T \nabla \mathbf{g}(\mathbf{x}_o) = 0 \\ \mathbf{g}(\mathbf{x}_o) = 0 \end{array} \right\} \tag{11}$$

Note that the constraints $\mathbf{g}(\mathbf{x}) = \mathbf{c}$ are easily transformed into the set $\overline{\mathbf{g}}(\mathbf{x}) = \mathbf{g}(\mathbf{x}) - \mathbf{c} = 0$.

Furthermore, if the real-valued functions $f(\mathbf{x})$ and $\mathbf{g}(\mathbf{x})$ possess continuous first- and second-order partial derivatives throughout a spherical neighborhood of the point $\mathbf{x}_o$ within an open region $U \subseteq \Re^n$, then the first- and second-order partial derivatives of $\mathbf{L}$ [as given in Eq. (10) for the $m$ real-valued Lagrange multipliers $\lambda$] are continuous throughout the spherical neighborhood of $\mathbf{x}_o$ as well. Thus, we find that if the principal subdeterminants of the bordered Hessian,[5] $\Delta_r(\mathbf{x}, \lambda)$, evaluated at the point $(\mathbf{x}_o, \lambda_o)$ are nonzero for $r = m+1, \ldots, n$ where $$\Delta_r(\mathbf{x}_o, \lambda_o) = \begin{vmatrix} \mathbf{H}_L(\mathbf{x}_o, \lambda_o)_{rr} & \vdots & \nabla \mathbf{g}^T(\mathbf{x}_o)_{rm} \\ \hdashline \nabla \mathbf{g}(\mathbf{x}_o)_{mr} & \vdots & 0 \end{vmatrix} \tag{12}^*$$

$\mathbf{H}_L$ is defined as the Hessian of the Lagrangian, then $f(\mathbf{x})$ subject to $\mathbf{g}(\mathbf{x}) = 0$ has a strong local extremum at $\mathbf{x}_o$. Additionally, if $$(-1)^r \Delta_r(\mathbf{x}_o, \lambda_o) > 0 \ (r = m+1, \ldots, n) \tag{13}$$

then $\mathbf{L}$, and hence $f(\mathbf{x})$ subject to $\mathbf{g}(\mathbf{x}) = 0$, has a strong local maximum at $\mathbf{x}_o$. If $$(-1)^m \Delta_r(\mathbf{x}_o, \lambda_o) > 0 \ (r = m+1, \ldots, n) \tag{14}$$

then L, and hence $f(\mathbf{x})$ subject to $\mathbf{g}(\mathbf{x}) = 0$, has a strong local minimum at $\mathbf{x}_o$.

C. Functions Subject to *k* Inequality and *m* Equality Constraints

The problem associated with the introduction of *k* inequality constraints is more complicated than the preceding; however, optimization theory was greatly advanced in 1951 when Kuhn and Tucker extended the traditional methods associated with Lagrange multipliers to problems with inequality and non-negativity restrictions.[7,11] The result is a set of conditions that must be satisfied in order for a maximum to exist.[†] By comparing the individual maxima, a global maximum may be identified (assuming it exists). Again, what follows is merely a summary of the great body of work pertaining to multi-variable optimizations subject to both equality and inequality constraints. A more detailed accounting of Kuhn-Tucker theory is given in *Classical Optimization* by Panik.[5]

To maximize the real-valued function $f(\mathbf{x})$ subject to the *k* inequality constraints $\mathbf{d}(\mathbf{x}) \geq 0$, Kuhn-Tucker theory involves transforming the *k* inequality constraints into *k* equality constraints by introducing *k* positive numbers $s_j^2$ so that we form the augmented Lagrangian $$\mathbf{L}(\mathbf{x},\mu,\mathbf{s}) = f(\mathbf{x}) + \sum_{j=1}^{k} \mu_j \left( d_j(\mathbf{x}) - s_j^2 \right) = f(\mathbf{x}) + \mu^T (\mathbf{d}(\mathbf{x}) - \mathbf{y}) \qquad (15)$$

Here, we have defined the *k* elements of y according to $y_j = s_j^2$ and defined $\mu$ as the real-valued set of Lagrange multipliers.[‡]

Assuming there exists a local maximum at $\mathbf{x}_o$ for all $\mathbf{x} \in \Re^n$ and that $f(\mathbf{x})$ is differentiable, then the conditions which must be satisfied in order for a maximum to exist are given by $$\left.\begin{array}{l} \nabla f(\mathbf{x_o}) + \sum_{j=1}^{k} \mu_{o,j} \nabla d_j(\mathbf{x_o}) = 0 \\ \sum_{j=1}^{k} \mu_{o,j} d_j(\mathbf{x_o}) = 0 \\ d_j(\mathbf{x_o}) \geq 0 \quad (j=1,\ldots,k) \\ \mu_{o,j} \geq 0 \quad (j=1,\ldots,k) \end{array}\right\} \text{ or } \left.\begin{array}{l} \nabla f(\mathbf{x_o}) + \mu_o^T \nabla \mathbf{d}(\mathbf{x_o}) = 0 \\ \mu_o^T \mathbf{d}(\mathbf{x_o}) = 0 \\ \mathbf{d}(\mathbf{x_o}) \geq 0 \\ \mu_o \geq 0 \end{array}\right\} \quad (16)$$

If nonnegativity is to be imposed, the requirement that $\mathbf{x_o} \geq 0$ can be incorporated into the existing set of $k$ constraints, thus forming the set of $\bar{k} = k + n$ constraints $\bar{\mathbf{d}} \geq 0$ where $\bar{\mathbf{d}}^T(\mathbf{x}) = \{\mathbf{d}^T(\mathbf{x}), \mathbf{x}^T\}$. It follows that Eq. (16) remains unchanged with the exception of $\mathbf{d}(\mathbf{x})$ being replaced by $\bar{\mathbf{d}}(\mathbf{x})$. However, it may be useful in some problems to treat $\mathbf{x_o} \geq 0$ as being explicit. In these cases Eq. (16) is modified so that $$\left.\begin{array}{l} \frac{\partial f}{\partial x_i}(\mathbf{x_o}) + \sum_{j=1}^{k} \mu_{o,j} \frac{\partial d_j}{\partial x_i}(\mathbf{x_o}) \leq 0 \quad (i=1,\ldots,n) \\ \sum_{i=1}^{n} x_i \left( \frac{\partial f}{\partial x_i}(\mathbf{x_o}) + \sum_{j=1}^{k} \mu_{o,j} \frac{\partial d_j}{\partial x_i}(\mathbf{x_o}) \right) = 0 \\ \sum_{j=1}^{k} \mu_{o,j} d_j(\mathbf{x_o}) = 0 \\ d_j(\mathbf{x_o}) \geq 0 \quad (j=1,\ldots,k) \\ \mu_{o,j} \geq 0 \quad (j=1,\ldots,k) \\ x_{o,i} \geq 0 \quad (i=1,\ldots,n) \end{array}\right\} \text{ or } \left.\begin{array}{l} \nabla f(\mathbf{x_o}) + \mu_o^T \nabla \mathbf{d}(\mathbf{x_o}) \leq 0 \\ \mathbf{x_o}^T \left( \nabla f(\mathbf{x_o}) + \mu_o^T \nabla \mathbf{d}(\mathbf{x_o}) \right) = 0 \\ \mu_o^T \mathbf{d}(\mathbf{x_o}) = 0 \\ \mathbf{d}(\mathbf{x_o}) \geq 0 \\ \mu_o \geq 0 \\ \mathbf{x_o} \geq 0 \end{array}\right\} \quad (17)$$

If we wish to maximize the function $f(\mathbf{x})$ subject to $m$ constraints of the form $\mathbf{g}(\mathbf{x}) = 0$ and $k$ constraints of the form $\mathbf{d}(\mathbf{x}) \geq 0$, then combining the results of Eqs. (11) and (16) we find that a local maximum exists at the point $(\mathbf{x_o}, \lambda_o, \mu_o)$ if the following conditions hold:

$$\left.\begin{array}{l}\nabla f(\mathbf{x}_o)+\sum_{i=1}^{k}\mu_{o,i}\nabla d_i(\mathbf{x}_o)+\sum_{j=1}^{k}\lambda_{o,j}\nabla g_j(\mathbf{x}_o)=0\\ \sum_{i=1}^{k}\mu_{o,i}d_i(\mathbf{x}_o)=0\\ d_i(\mathbf{x}_o)\geq 0 \quad (j=1,\ldots,k)\\ g_j(\mathbf{x}_o)=0 \quad (j=1,\ldots,m)\\ \mu_{o,i}\geq 0 \quad (j=1,\ldots,k)\end{array}\right\} \text{or} \left.\begin{array}{l}\nabla f(\mathbf{x}_o)+\mu_o^T\nabla d(\mathbf{x}_o)+\lambda_o^T\nabla g(\mathbf{x}_o)=0\\ \mu_o^T d(\mathbf{x}_o)=0\\ d(\mathbf{x}_o)\geq 0\\ g(\mathbf{x}_o)=0\\ \mu_o\geq 0\end{array}\right\} \quad (18)$$

For both Eqs. (16) and (18), the condition that $\mu_o^T d(\mathbf{x}_o)=0$ results in $2^k$ possible combination of $\mu_{o,i}=0$ and $d_i(\mathbf{x}_o)=0$. For $\bar{k}$ of the $k$ inequality constraints set to their boundary values, it follows that $k-\bar{k}$ of the Lagrange multipliers must be set to zero. The effect is a transformation of $k$ inequality constraints into $\bar{k}$ equality constraints for which $\bar{d}(\mathbf{x}_o)=0$ with the $\bar{k}$ Lagrange multipliers, denoted by $\bar{\mu}_o$, retained (in essence, "activating" $\bar{k}$ of the $k$ constraints). Thus, for each of the $2^k$ possible combinations, Eq. (18) reduces to $$\left.\begin{array}{l}\nabla f(\mathbf{x}_o)+\sum_{i=1}^{\bar{k}}\bar{\mu}_{o,i}\nabla \bar{d}_i(\mathbf{x}_o)+\sum_{j=1}^{k}\lambda_{o,j}\nabla g_j(\mathbf{x}_o)=0\\ \bar{d}_i(\mathbf{x}_o)=0 \quad (j=1,\ldots,\bar{k})\\ g_j(\mathbf{x}_o)=0 \quad (j=1,\ldots,m)\\ \bar{\mu}_{o,i}\geq 0 \quad (j=1,\ldots,\bar{k})\end{array}\right\} \text{or} \left.\begin{array}{l}\nabla f(\mathbf{x}_o)+\bar{\mu}_o^T\nabla\bar{d}(\mathbf{x}_o)+\lambda_o^T\nabla g(\mathbf{x}_o)=0\\ \bar{d}(\mathbf{x}_o)\geq 0\\ g(\mathbf{x}_o)=0\\ \bar{\mu}_o\geq 0\end{array}\right\} \quad (19)$$

If the solution of Eq. (19) satisfies the inequality conditions of Eq. (18), then the boundary solution is deemed viable.

A significant number of possible solutions can result from activating $\bar{k}$ of the $k$ constraints. However, for $\bar{k}+m>n$ (assuming $k>n-m$ and assuming nondegeneracy), the system of equations are overdetermined. It follows that $\sum_{i=n-m+1}^{k}\frac{k!}{(k-i)!\,i!}$ of the $2^k$ cases may be Inspection reveals that there are a total of $\dfrac{k!}{(k+m-n)!\,(n-m)!}$ such cases. Thus, there remain $2^k - \sum_{i=n-m}^{k} \dfrac{k!}{(k-i)!\,i!}$ cases in which a quadratic optimization may be done. If it should occur that $k \leq n-m$, then no over-constrained cases exist. Likewise, if $k < n-m$ then all resulting cases are underdetermined and each of the $2^k$ cases must be examined and compared against the inequality constraints.

D. Remarks on Global Optimizations for Closed and Bounded Sets

The question as to which critical points of an objective function can be classified as the global maximum and the global minimum is contingent upon extrema existing. For instance, the unconstrained function $z(x) = x^2$ has one minimum at $x = 0$ but possesses no global maximum. However, if the condition $5 \leq x \leq 10$ is imposed, then a global maximum occurs at $x = 10$ and a global minimum at $x = 5$. Thus, it is assumed that the objective function is properly bounded. In some cases, the nature of the objective function's extrema can be determined by inspection, as in the example above. But for many problems, this can not be done.

If it occurs that the set of constraints form a closed and bounded set, we may be sure that the global maximum and minimum of a function will occur for values contained in that set. Formally speaking, if it is known that the real-valued function $f(\mathbf{x})$, $\mathbf{x} \in \Re^n$ is strictly concave over a closed convex set $V \subset \Re^n$, then $f(\mathbf{x})$ assumes a strong global maximum somewhere over its domain. Likewise, if $f(\mathbf{x})$ strictly concave over $V$, then any local maximum is also the strong global maximum of $f(\mathbf{x})$ over $V$.[5] In a similar manner, the same can be said for identifying the union the open set U and the boundary $\partial U$, then, assuming $\partial U$ is a piecewise continuous curve, we may assume that $V$ is closed and bounded in $\Re^n$ since it contains all of its own boundary points. It follows that the continuous function $f(\mathbf{x})$ assumes its global maximum and minimum at distinct points of $V$.[4] In this case, the following methodology would appear sufficient for finding the global maximum and minimum of a function:

(i) Locate all critical points of $f(\mathbf{x})$ in U.

(ii) Find the critical points of $f(\mathbf{x})$ viewed as a function only on $\partial U$.

(iii) Compute the value of $f(\mathbf{x})$ at all critical points.

(iv) Compare the values of (iii), selecting the maximum and minimum as the global extremum.

For those functions that do not correspond to a closed and bounded set $V$ and are neither strictly concave nor strictly convex, the critical points must be examined on a case by case basis to determine if a global maximum or minimum exists.

III. LAGRANGE MULTIPLIERS AND THE QUADRATIC PROBLEM

A. The Unconstrained Quadratic Problem

We begin by addressing the general unconstrained quadratic problem $$\text{Maximize } f(\mathbf{x}) = \sum_{i=1}^{n} x_i c_i + \sum_{i,j=1}^{n} x_i P_{ij} x_j = \mathbf{x}^T \mathbf{c} + \mathbf{x}^T \mathbf{P} \mathbf{x} \qquad (20)$$

for $\mathbf{x} \in \Re^n$. We may assume $\mathbf{P}$ is a symmetric matrix given the nature of the quadratic form. This follows from the fact that if we have a non-symmetric matrix $\mathbf{Q}$, then the coefficient of each term $x_i x_j$ is $q_{ij} + q_{ji}$. Thus, $\mathbf{P}$ can always be written as a symmetric matrix by defining a new set of coefficients $p_{ij} = \dfrac{q_{ij}+q_{ji}}{2}$ so that $p_{ij}+p_{ji} = q_{ij}+q_{ji}$. From Eq. (1), we find that only one critical point exists at $x_o$ and is given by the value (assuming P is invertible)

$$x_o = -\frac{1}{2}P^{-1}c \qquad (21)$$

Constructing the Hessian via Eq. (4), we see that $H = |2P|$ and, therefore, the point is a global minimum if $|P_{rr}(x_o)| \geq 0$ and a global maximum if $(-1)^r|P_{rr}(x_o)| \geq 0$ for $(r = 1,\ldots,n)$.

B. Quadratic Forms Subject to $m$ Equality Linear Constraints

Similar to Eq. (1), the $m$ equality, linearly constrained quadratic problem is stated as $$\left. \begin{array}{ll} \text{Maximize} & z = \sum_{i=1}^{n} x_i c_i + \sum_{i,j=1}^{n} x_i P_{ij} x_j \\ \text{Subject to} & \sum_{j=1}^{n} D_{ij} x_j = e_j \quad (i=1,\ldots,m) \end{array} \right\} \text{ or } \left. \begin{array}{ll} \text{Maximize} & z = x^T c + x^T P x \\ \text{Subject to} & Dx = e \end{array} \right\} \qquad (22)$$

where $x \in \Re^n$. We assume that the conditions $Dx = e$ comprise a non-degenerate set with $m < n$. If $m > n$, then the system is over specified and no solution may occur. In the case that $m = n$, then one solution exists at the point $x_o = D^{-1}e$ providing $|D| \neq 0$. Hence, no optimization is necessary.

Constructing the Lagrangian, we find that $$L = x^T c + x^T P x + \lambda^T(Dx - e) \qquad (23)$$

where $m$ Lagrange multipliers have been introduced. From Eq. (11) we obtain the global extremum $$\begin{Bmatrix} \mathbf{x}_o \\ \lambda_o \end{Bmatrix} = \begin{Bmatrix} 2\mathbf{P} & \mathbf{D}^T \\ \mathbf{D} & 0 \end{Bmatrix}^{-1} \begin{Bmatrix} -\mathbf{c} \\ \mathbf{e} \end{Bmatrix} \qquad (24)$$

where it is assumed that the matrix inversion is possible. We see from Eq. (12) that the determinants of the principle submatrices take the form $$\Delta_r = \begin{vmatrix} 2\mathbf{P}_{rr} & \mathbf{D}^T_{rm} \\ \hline \mathbf{D}_{mr} & 0 \end{vmatrix} \quad (r = m+1, \ldots, n) \qquad (25)$$

where $\Delta_r$ is independent of $\mathbf{x}_o$ and $\lambda_o$. The point $\mathbf{x}_o$ is identified as a global minimum or global maximum by comparing Eq. (25) to the conditions of Eqs. (13) and (14).

C. Quadratic Forms Subject to $m$ Equality, $k$ Inequality Linear Constraints The quadratic form subject to $m$ equality and $k$ inequality linear constraints is expressed as $$\left. \begin{array}{l} \text{Maximize} \quad z = \sum_{i=1}^{n} x_i c_i + \sum_{i,j=1}^{n} x_i P_{ij} x_j \\ \text{Subject to} \quad \sum_{j=1}^{n} D_{ij} x_j = e_j \quad (i=1,\ldots,m) \\ \phantom{\text{Subject to}} \quad \sum_{j=1}^{n} G_{ij} x_j \geq q_j \quad (i=1,\ldots,k) \end{array} \right\} \text{ or } \left. \begin{array}{l} \text{Maximize} \quad z = \mathbf{x}^T \mathbf{c} + \mathbf{x}^T \mathbf{P} \mathbf{x} \\ \text{Subject to} \quad \mathbf{D}\mathbf{x} = \mathbf{e} \\ \phantom{\text{Subject to}} \quad \mathbf{G}\mathbf{x} \geq \mathbf{q} \end{array} \right\} \qquad (26)$$

where we assume a maximum exists for $\mathbf{x} \in \Re^n$. From the Kuhn-Tucker conditions of Eq. (18), we obtain the criterion which must be satisfied in order for a maximum to exist at $\mathbf{x}_o$. Namely, $$\left. \begin{array}{l} 2\mathbf{P}\mathbf{x}_o + \mu_o^T \mathbf{G} + \lambda_o^T \mathbf{D} = -\mathbf{c} \\ \mu_o^T (\mathbf{G}\mathbf{x}_o - \mathbf{q}) = 0 \\ \mathbf{G}\mathbf{x}_o \geq \mathbf{q} \\ \mathbf{D}\mathbf{x}_o = \mathbf{e} \\ \mu_o \geq 0 \end{array} \right\} \qquad (27)$$

The $2^k$ possible solution implied by the condition that $\mu_o^T(Gx_o - q) = 0$ result in the activation of $\bar{k}$ of the $k$ linear constraints. Identifying these $\bar{k}$ constraints and Lagrange multipliers as $\overline{G}x_o = \overline{q}$ and $\overline{\mu}_o$, respectively, Eq. (27) is reduced to $$\left. \begin{array}{l} 2Px_o + \overline{\mu}_o^T \overline{G} + \lambda_o^T D = -c \\ \overline{G}x_o = \overline{q} \\ Dx_o = e \\ \overline{\mu}_o \geq 0 \end{array} \right\} \quad (28)$$

Solutions to Eq. (28) are given by $$\begin{Bmatrix} x_o \\ \lambda_o \\ \overline{\mu}_o \end{Bmatrix} = \begin{Bmatrix} 2P & D^T & \overline{G}^T \\ D & 0 & 0 \\ \overline{G} & 0 & 0 \end{Bmatrix}^{-1} \begin{Bmatrix} -c \\ e \\ \overline{q} \end{Bmatrix} \quad (29)$$

where the operating matrix is assumed invertible. Only solutions that satisfy the inequality conditions of Eq. (28) are kept. Comparison of the value of the objective function for all viable solutions reveals the point that can be associated with the global maximum.

IV. Application to Magnetostatics

A. Minimization of the Current Metric

We begin by focusing solely on the static and quasi-static cases, thus assuming that the source currents are either held constant or ramped relatively slowly in time. Given $n$ magnetomotive sources (or, in this sense, actuators), we wish to operate the sources with minimal currents so that a desired magnetic field may be specified for a selected point in space $x_o$ where $x_o \in \Re$. The total magnetic field at any point $\mathbf{x}$, $\mathbf{b}(\mathbf{x})$, is the linear superposition of the magnetic fields due to each source evaluated at $\mathbf{x}$:

$$\mathbf{b}(\mathbf{x}) = \sum_{i=1}^{n} \mathbf{b}_i(\mathbf{x}) \qquad (30)$$

Since $\mathbf{b}_i(\mathbf{x})$ is linear with respect to its corresponding source current, $I_i$, the above may be written as $$\mathbf{b}(\mathbf{x}, \mathbf{I}) = \sum_{i=1}^{n} \overline{\mathbf{B}}_i(\mathbf{x}) I_i \qquad (31)$$

where $\overline{\mathbf{B}}_i(\mathbf{x})$ consists of the three current-independent components of the magnetic field for each source. If we define the $3 \times n$ matrix $\overline{\mathbf{B}}(\mathbf{x})$ as $$\overline{\mathbf{B}}(\mathbf{x}) = \{\overline{\mathbf{B}}_1(\mathbf{x}) \mid \overline{\mathbf{B}}_2(\mathbf{x}) \mid \cdots \mid \overline{\mathbf{B}}_n(\mathbf{x})\} \qquad (32)$$

and we write the currents as the $n$-element column vector $\mathbf{I}$, then Eqs. (31) and (32) can be combined to form the matrix relationship $$\mathbf{b}(\mathbf{x}, \mathbf{I}) = \overline{\mathbf{B}}(\mathbf{x}) \mathbf{I} \qquad (33)$$

Note that $n > 3$ is assumed in order for an optimization to be made for a desired magnetic field $\mathbf{b}$ (which consist of three components). If $n < 3$ (i.e., two actuators or less), the system is over constrained and no solution exists unless there is a degeneracy in Eq. (33). If $n = 3$, then the solution to the currents, $\mathbf{I}_\bullet$, is given by $\mathbf{I}_\bullet = \overline{\mathbf{B}}^{-1}(\mathbf{x}_\bullet) \mathbf{b}$.

We now focus our attention on the current metric defined as $$z(\mathbf{I}) = \sum_{i=1}^{n} I_i^2 = \mathbf{I}^\mathrm{T} \mathbf{I} \qquad (34)$$

While the metric does not specifically limit the individual currents, it does serve as a means of penalizing those solutions that are associated with strong currents. The problem of finding an optimal set of currents (for $n > 3$ sources) may now be stated in the form of Eq. (22) for which there are $m = 3$ equality constraints:

$$\left.\begin{array}{ll} \text{Maximize} & z(\mathbf{I}) = -\mathbf{I}^T \mathbf{I} \\ \text{Subject to} & \overline{\mathbf{B}}(\mathbf{x}_o)\mathbf{I} = \mathbf{b} \end{array}\right\} \tag{35}$$

It is noted that we could just as easily minimize the current metric above without loss of generality; however, writing the problem in the form of Eq. (35) is convenient given the previous notation of Eqs. (22)-(26). Since the metric of Eq. (35) is a concave function, the solution for the currents follows from Eq. (24):

$$\begin{Bmatrix} \mathbf{I}_o \\ \lambda_o \end{Bmatrix} = \begin{Bmatrix} -2\mathbf{I}_D & \overline{\mathbf{B}}(\mathbf{x}_o)^T \\ \overline{\mathbf{B}}(\mathbf{x}_o) & 0 \end{Bmatrix}^{-1} \begin{Bmatrix} 0 \\ \mathbf{b} \end{Bmatrix} \tag{36}$$

where $\mathbf{I}_D$ is the identity matrix. While Eq. (25) could be used to determine the curvature of the solution, inspection of Eq. (35) reveals that only one extremum (and hence, the global maximum) of the negative current metric can occur.

B. Minimization of the Current Metric Subject to Current Limits

While the current metric is sufficient in restricting the currents to small values in most cases, it does not minimize them. It is possible that a larger metric results when smaller currents are distributed over several sources. For example, say the desired field for a four source system corresponds to the optimal set of currents $\mathbf{I}_o^T = \{10 \quad 80 \quad 10 \quad 80\}(A)$ for which $z(\mathbf{I}_o) = 13000 \, A^2$. If the individual currents must be less than 75 A, a more useful solution would correspond to $\mathbf{I}_o^T = \{60 \quad 70 \quad 60 \quad 70\}(A)$, for which $z(\mathbf{I}_o) = 17000 \, A^2$, providing the currents generate the same magnetic field. Including the $k$ linear current limits $\mathbf{DI} \geq \mathbf{e}$ into Eq. (35), our general $n$-source, linearly constrained problem is stated as $$\left.\begin{array}{ll} \text{Maximize} & z = -\mathbf{I}^T\mathbf{I} \\ \text{Subject to} & \overline{\mathbf{B}}(\mathbf{x}_o)\mathbf{I} = \mathbf{b} \\ & \mathbf{DI} \geq \mathbf{e} \end{array}\right\} \quad (37)$$

Since it is more commonly found that the $n$ actuators possess upper and lower limits according to $|I_i| \leq I_{max}$ ($i = 1, \ldots, n$), the constraints form a closed and bounded set providing the specification of $\mathbf{B}$ still holds for the range of allowed currents. The problem becomes $$\left.\begin{array}{ll} \text{Maximize} & z(\mathbf{I}) = -\mathbf{I}^T\mathbf{I} \\ \text{Subject to} & \overline{\mathbf{B}}(\mathbf{x}_o)\mathbf{I} = \mathbf{b} \\ & \begin{Bmatrix} \mathbf{I}_D \\ -\mathbf{I}_D \end{Bmatrix}\mathbf{I} \geq -\begin{Bmatrix} \mathbf{I}_{max} \\ \mathbf{I}_{max} \end{Bmatrix} \end{array}\right\} \quad (38)$$

where $k = 2n$ inequality constraints with $I_{max,i} = I_{max}$ for $i = 1, \ldots, n$ have been introduced. From Eq. (27), the conditions that must be satisfied in order for maximum to exist are given by $$\left.\begin{array}{l} -2\mathbf{I}_o + \boldsymbol{\mu}_o^T\begin{Bmatrix} -\mathbf{I}_D \\ \mathbf{I}_D \end{Bmatrix} + \boldsymbol{\lambda}_o^T\overline{\mathbf{B}}(\mathbf{x}_o) = 0 \\ \boldsymbol{\mu}_o^T\left(\begin{Bmatrix} -\mathbf{I}_D \\ \mathbf{I}_D \end{Bmatrix}\mathbf{I}_o + \begin{Bmatrix} \mathbf{I}_{max} \\ \mathbf{I}_{max} \end{Bmatrix}\right) = 0 \\ \overline{\mathbf{B}}(\mathbf{x}_o)\mathbf{I}_o = \mathbf{b} \\ -\mathbf{I}_{max} \leq \mathbf{I}_o \leq \mathbf{I}_{max} \\ \boldsymbol{\mu}_o \geq 0 \end{array}\right\} \quad (39)$$

The possible $2^{2n} = 4^n$ solutions of the above set of equations follow from Eq. (29) where individual constraints are activated among the $2n$ inequality conditions. As was previously discussed, when the activated constraints combined with the equality constraints outnumber the degrees of freedom, the system of equations become over specified and no solution need be calculated. For those cases in which the system of equations is exactly specified, the solution must be checked against the inequality constraints to deem it viable. There remain $4^n - \sum_{i=n-3}^{2n} \dfrac{2n!}{(2n-i)!\, i!}$ of the $4^n$ cases which can be solved (assuming a solution exists). Those solutions that satisfy the constraints are saved and the set that results in the maximum value of $z(\mathbf{I_o}) = -\mathbf{I_o^T}\mathbf{I_o}$ [or minimum of $z(\mathbf{I_o}) = \mathbf{I_o^T}\mathbf{I_o}$] is reported as the optimal solution.

C. Consideration of Magnetic Force

It is sometimes useful to restrict the magnetically generated force on a small permanent moment. For example, quasi-static systems such as magnetic suspensions and the Magnetic Stereotaxis System (discussed below) can profit from an inclusion of force constraints if higher currents are acceptable. The force at $\mathbf{x_o}$, $\mathbf{f}(\mathbf{x_o})$, generated on a small permanent magnetic moment, $\mathbf{m}$, due to a magnetic field, $\mathbf{b}$, is given by[12]

$$\mathbf{f}(\mathbf{x_o}) = \nabla(\mathbf{m^T}\mathbf{b}(\mathbf{x}))\big|_{\mathbf{x}=\mathbf{x_o}} \tag{40}$$

An easier notation for the present purposes involves writing the three component of the force as $$f_i(\mathbf{x_o}) = \mathbf{m^T}\dfrac{\partial \mathbf{b}}{\partial x_i}(\mathbf{x_o}) \quad (i=1,2,3) \tag{41}$$

For those problems in which the moment is allowed to align with the magnetic field [i.e., $m = \frac{\|m\|}{\|b\|}b(x_o)$], Eq.(41) is transformed into $$f_i(x_o) = \frac{\|m\|}{\|b(x_o)\|}b(x_o)^T\left(\frac{\partial b(x)}{\partial x_i}\right)\bigg|_{x=x_o} \quad (i=1,2,3) \quad (42)$$

where the strength of the moment $\|m\|$ is known. Combining the results of Eq. (42) with Eq. (33), a somewhat complicated problem arises for those cases in which the orientation of the magnetic field at $x_o$ is unrestricted. This can be seen in the nonlinear form of $$f_i(x_o, I) = \|m\| \frac{I^T \overline{B}(x_o)^T\left(\frac{\partial \overline{B}}{\partial x_i}(x_o)\right)I}{\sqrt{I^T \overline{B}(x_o)^T \overline{B}(x_o)I}} \quad (i=1,2,3) \quad (43)$$

For the present purposes, only those cases that rely on a specified magnetic field are considered.

Using the current dependence of the magnetic sources and a predetermined magnetic field b where $b = \overline{B}(x_o)I$, Eq. (42) can be written in two forms. The linear and quadratic forms are given by, respectively, $$f_i(x_o, I) = \frac{\|m\|}{\|b\|}b^T\left(\frac{\partial \overline{B}}{\partial x_i}(x_o)\right)I \quad (i=1,2,3) \quad (44)$$

and $$f_i(x_o, I) = \frac{\|m\|}{\|b\|}I^T \overline{B}(x_o)^T\left(\frac{\partial \overline{B}}{\partial x_i}(x_o)\right)I \quad (i=1,2,3) \quad (45)$$

While the form of Eq. (44) may appear more useful, at least seven actuators must be present in order to overcome the six constraints due to the specification of the magnetic field and force. If it is important that both the force and field be specified and if there are a sufficient number of actuators, then the work follows from Eqs. (35)-(39) with the three additional force constraints being included into the field constraints. If there are exactly six actuators, then there exists a unique solution to the problem at $$\mathbf{I}_o = \left\{ \begin{array}{c} \frac{\|\mathbf{m}\|}{\|\mathbf{b}\|} \nabla(\mathbf{b}^T \overline{\mathbf{B}}(\mathbf{x}))\big|_{\mathbf{x}=\mathbf{x}_o} \\ \overline{\mathbf{B}} \end{array} \right\}^{-1} \left\{ \begin{array}{c} \mathbf{f} \\ \mathbf{b} \end{array} \right\} \qquad (46)$$

providing the operating matrix is invertible and the currents are unbounded.[25]

More often than not, the experimenter is more concerned with either minimizing a component of the force or the strength of the force with respect to a limited range of currents and a desired magnetic field rather than specifying a specific value of the force. If examining a component of the force, Eq. (45) is generalized so that the force along the unit vector $\mathbf{u}$ ($\|\mathbf{u}\| = 1$) is minimized. The force component of interest becomes $\mathbf{u}^T \mathbf{f}(\mathbf{x}_o, \mathbf{I})$ and the problem is written as $$\left. \begin{array}{ll} \text{Maximize} & z(\mathbf{I}) = -\mathbf{u}^T \mathbf{f}(\mathbf{x}_o, \mathbf{I}) = -\frac{\|\mathbf{m}\|}{\|\mathbf{b}\|} \left( \sum_{i=1,2,3} u_i \, \mathbf{I}^T \, \overline{\mathbf{B}}(\mathbf{x}_o)^T \left( \frac{\partial \overline{\mathbf{B}}}{\partial x_i}(\mathbf{x}_o) \right) \mathbf{I} \right) \\ \text{Subject to} & \overline{\mathbf{B}}(\mathbf{x}_o) \mathbf{I} = \mathbf{b} \\ & \left\{ \begin{array}{c} \mathbf{I}_D \\ -\mathbf{I}_D \end{array} \right\} \mathbf{I} \geq -\left\{ \begin{array}{c} \mathbf{I}_{max} \\ \mathbf{I}_{max} \end{array} \right\} \end{array} \right\} \qquad (47)$$

Likewise, if the force strength is to be minimized, a quadratic form is obtained for the objective function by squaring the force components of Eq. (44):

$$\left. \begin{array}{ll} \text{Maximize} & z(\mathbf{I}) = -\mathbf{f}(\mathbf{x}_o, \mathbf{I})^T \mathbf{f}(\mathbf{x}_o, \mathbf{I}) = -\left( \frac{\|\mathbf{m}\|}{\|\mathbf{b}\|} \right)^2 \left( \sum_{i=1,2,3} \mathbf{I}^T \left( \frac{\partial \overline{\mathbf{B}}^T}{\partial x_i}(\mathbf{x}_o) \right) \mathbf{b}\mathbf{b}^T \left( \frac{\partial \overline{\mathbf{B}}}{\partial x_i}(\mathbf{x}_o) \right) \mathbf{I} \right) \\ \text{Subject to} & \overline{\mathbf{B}}(\mathbf{x}_o) \mathbf{I} = \mathbf{b} \\ & \left\{ \begin{array}{c} \mathbf{I}_D \\ -\mathbf{I}_D \end{array} \right\} \mathbf{I} \geq -\left\{ \begin{array}{c} \mathbf{I}_{max} \\ \mathbf{I}_{max} \end{array} \right\} \end{array} \right\} \qquad (48)$$

If it is desired that the force be maximized rather than minimized, then the negative sign to the objective function is left off in Eqs. (47) and (48). The conditions that establish the existence of a minimum or maximum follow from Eq. (27). Note that only for force minimizations may the currents be left unbounded.

IV. Magnetic Stereotaxis System as an Example

A. Introduction to the Magnetic Stereotaxis System

The Magnetic Stereotaxis System (MSS) originated from the hopes that a less-invasive methodology could be developed which would allow neurosurgeons to operate in previously inaccessible regions of the brain. By introducing a small permanent magnetic implant into the brain through a small "burr hole" drilled into the skull prior to the operation, large superconducting coils could be used in conjunction with a pushing mechanism to magnetically guide the implant and overlaying catheter through the brain's parenchyma, all the while avoiding the important structures of the brain. The operational methodology of the MSS was, and continues to be, expected to be less destructive to the tissues of the brain than the shunts, straight tubes, and other devices associated with conventional techniques in neurosurgery.[13]

The first MSS was conceptually developed in 1984 as the Video Tumor Fighter (VTF), a system specifically focused on the eradication of deep-seated brain tumors via hyperthermia-based treatment.[14,15] It was envisioned that the magnetic coils of the VTF would guide a small (~3 mm diameter) magnetic thermosphere through the brain into a tumor. Rastering the implant throughout the volume of the growth, the tumor cells could be destroyed by inductively heating the implant with radio-frequency radiation.[16-17]

Further studies revealed that the reality of a magnetomotive based system used to direct a small implant promised numerous applications other than the hyperthermia-based treatment of brain tumors by induction.[17,18-20] These included: biopsy, pallidotomy, delivery of precision radiation therapy, magnetically placed implants that deliver chemotherapy to otherwise inaccessible tumor locations, and (by attaching a semi-permeable catheter to the implant) the delivery of chemicals to specific sites in the brain without the need for penetrating the blood-brain barrier which has complicated contemporary systemic chemical delivery.[21,22] This means of chemical delivery seemed particularly hopeful in the treatment of Parkinson's disease, where the catheter could be used to deliver dopamine to the affected regions of the brain with minimal indiscriminate distribution of the neurotransmitter to the surrounding tissue, thereby lessening attendant side effects. It was in the light of these possible broadened applications of the VTF that the system became known as the MSS.

The six superconducting coils of the most recent MSS apparatus are located in a rectangular box. With the z-axis defined in the direction of the axial component of the head, the x- and y- coil axes are rotated 45° from the sagital plane of the head, symmetrically located such that the horizontal extension away from patient's body is minimized (see Fig. 1). Because the lower edge of the treatable part of the brain is typically located 10 cm above the shoulder line for an average adult, the z-coils (located on the body-axis of the supine patient) were compressed to allow for a maximum extension of the head into the helmet.

The vision component of the MSS consists of a superposition of pre-operative MRI images referenced by biplanar fluoroscopy cameras linked to a real-time host system. Both cameras are calibrated to the MSS six-coil helmet design. Using x-ray visible fiducial markers located on the skull of the conscious patient, the coordination of the implant's position inside the cranial volume to the helmet's reference system (and hence the corresponding MRI scan) is done through a series of coordinate transformations executed by a host system and displayed for the surgeon on a workstation.

The central problem to the inductively-based guidance of a magnetic implant pertains to the inverse problem of electromagnetism as influenced by Earnshaw's theorem.[23,24] The conventional problem of electromagnetism centers on the evaluation of the gradient and magnetic field given established magnetomotive sources. For the MSS, however, the situation is reversed in that the magnetic field is specified at a point in space while the strengths of the six actuators are to be determined. Control of the implant would be difficult in the MSS, given the fundamental instability of a non-diamagnetic moment in a static or quasi-static magnetic field as related to Earnshaw's theorem for static/quasi-static magnetic fields, if it were not for the resistive nature of the parenchyma. In early tests, small cylindrical (up to 5 mm in length and 5 mm in diameter) permanently magnetized NdBFe objects were used. The relatively strong moment of these objects (0.016 A-m$^2$ to more than 0.04 A-m$^2$) facilitated the creation of the necessary aligning torque without the requirement of a strong magnetizing field, resulting in lower current values.

The permanent magnetization of the implant requires a predetermined magnetic field in order to ensure that the implant is oriented in the desired direction. While it is possible to generate a magnetic force to displace the implant, it is found that the requirement of specific force and field alignment result in unobtainable currents (as high as thousands of amperes).[25] It was also found that even for viable solutions, the equilibrium state was sometimes unstable to such an extent that the implant tended to be difficult to control. For these reasons, discrete displacements occurred along the predetermined path by generating a "push" via an electric motor connected to a wire while orienting the implant's moment with a guiding magnetic field (see Fig. 2).

B. Minimization of the Current Metric for the MSS

Since the magnetic field must be oriented in the desired direction with minimal currents distributed among the coils, minimization of the current metric occurs via Eq. (38). While it may not appear practical to leave the currents unconstrained, it is found that in no circumstance do the coil currents exceed 52A for an aligning field of 0.3T generated at the magnetic implant for a sampling of the space that would be occupied by the patient's brain in the helmet cryostat (see Fig. 3). Given that this field is sufficient to align the implant without violating a current limit of 70A, it is acceptable for the present purposes to neglect current constraints in the minimization of the current metric. Only for fields greater than 0.4T should current limits be considered.

Figure 3 reveals that the average force has a value of 0.044N with a standard deviation of 0.019N. The maximum current magnitude remains below 52A for the sampled positions. The average value is found to be 34.2A with a standard deviation of 4.8A. Examining the square root of the current metric (i.e., the root-mean-square current), an average current of 21.4A is found with a standard deviation of 2.1A. Note that in none of the 13+ million cases does this value exceed 35A. Interestingly, the force-field angle favors 90° on average, with a standard deviation of 37.8°. It follows that the magnetically-generated force will tend to be oriented perpendicular to the direction of the applied field, and hence perpendicular to the desired implant displacement. Only if the force magnitude remains small compared to the rupture force of the parenchyma can this effect be neglected if the current metric is to be used as the method of generating solutions.

The reader may be inclined to believe that scaling down the currents or reducing the magnetic moment of the implant would remove this threat to implant displacement since the force would also be reduced ( recall that the magnetic force is linear with respect to both the currents and the magnetic moment). However, either of these approaches would only serve to reduce the torque generated on the magnetic moment and, hence, result in less accurate guidance and possibly unfavorable implant displacements. Fortunately, the forces encountered in early experiments with the MSS have produced no noticeable ill effects on implant motion since the individual implant displacements remain on the order of 3mm to 5mm, a value small enough to make course corrections between displacements. However, investigation is presently being conducted to evaluate the effects of using the force metric of Eqs. (47) and (48) to calculate the currents in order to provide more precise and reliable implant-catheter navigation.

If higher fields are desired with the current metric or if a force metric is to be used as the objective function to the constrained maximization, then it becomes necessary that current limits be included into the constraints. If a maximum current magnitude is specified for each coil (i.e., an upper and lower current limit), then we must include twelve inequality constraints in addition to the three constraints imposed by the magnetic field. There result a total of $2^{12} = 4096$ possible combinations of the Lagrange multipliers. Of these, $2^{12} - \sum_{i=4}^{12} \frac{12!}{(12-i)!\, i!} = 3797$ are over specified and can be thrown out. Furthermore, $\frac{12!}{(12-3)!\, 3!} = 220$ cases can be associated with the equality constraints, leaving 79 cases which must be addressed by the quadratic optimization routines.

VI. Conclusions

As has been shown, the optimization of linearly constrained quadratic object functions can be expressed in analytical form. Those quadratics that are subjected to equality linear constraints may be reduced to a set of linear equations by the use of Lagrange multipliers. By constructing the Hessian, the nature of the extremum many be discerned, be it a global maximum, a global minimum, or a saddle point. In the case of inequality constraints, Kuhn-Tucker theory allows us to construct a set of conditions that must be satisfied in order for a maximum (or minimum) to exist. By activating combinations of the constraints, possible solutions are generated which, by comparison with the Kuhn-Tucker conditions, provide the global maximum (or minimum). It was also shown that the application of such problems holds great promise in magnetostatics. Given the nature of the magnetic problem, optimizations may be made for an unconstrained or a linearly constrained current metric, force component, or force magnitude.

ACKNOWLEDGMENTS

The authors would like to thank Stereotaxis Inc. for supporting this work and for providing the example of the Magnetic Stereotaxis System.

References

[1] W. H. Press, S. A. Teukolsky, W. T. Vetterling, B. P. Flannery, *Numerical Recipes in C*, 2nd ed. (Cambridge University Press, New York, 1992).

[2] P. E. Gill, W. Murray, M. H. Wright, *Practical Optimization* (Academic Press, London, 1981).

[3] M. R. Hestenes, *Optimization Theory* (John Wiley and Sons, New York, 1975).

[4] J. E. Marsden, A. J. Tromba, *Vector Calculus*, 3rd ed. (W. H. Freeman and Co., New York, 1988).

[5] M. J. Panik, *Classical Optimization: Foundations and Extensions* (American Elsevier Publishing Co, Inc., New York, 1976).

[6] P. M. Pardalos, J. B. Rosen, *Lecture Notes in Computer Science* (Springer-Verlag, New York, 1987).

[7] G. R. Walsh, *Methods of Optimization* (John Wiley and Sons, New York, 1975).

[8] A. S. Deif, *Advanced Matrix Theory for Scientists and Engineers* (John Wiley and Sons, New York, 1982).

[9] L. Cooper, *Applied Nonlinear Programming* (Aloray, New Jersey, 1974).

[10] H. Anton, *Elementary Linear Algebra*, 5th ed. (John Wiley and Sons, New York, 1987).

[11] H. W. Kuhn, A. W. Tucker "Nonlinear Programming" in *Proceedings of the Second Berkeley Symposium on Mathematical Statistics and Probability* edited by J. Neyman (University of California Press, Berkeley, CA, 1951) pp. 481-492.

[12] J. D. Jackson, *Classical Electrodynamics*, 2nd ed. (New York: Wiley, 1975).

[13] R. G. McNeil, R. C. Ritter, B. Wang, M. A. Lawson, G. T. Gillies, K. G. Wika, E. G. Quate, M. A. Howard III, and M. S. Grady, "Functional Design Features and Initial Performance Characteristics of a Magnetic-Implant Guidance System for Stereotactic Neurosurgery," IEEE Trans. Biomed. Engr. 42, no. 8, 793-801 (1995).

[14] M. A. Howard, M. S. Grady, R. C. Ritter, G. T. Gillies, E. G. Quate, J. A. Molloy, "Magnetic Movement of a Brain Thermoceptor," Neurosurg. 24, 444-448 (1989).

[15] M. A. Howard III, R. C. Ritter, M. S. Grady, "Video Tumor Fighting System," U. S. Patent 4 869 247 (Sept. 26, 1989).

[16] M. S. Grady, M. A. Howard, W. C. Broaddus, H. R. Winn, J. A. Jane, R. C. Ritter, G. T. Gillies, E. G. Quate, J. A. Molloy, "Initial Experimental Results with a New Stereotactic Hyperthermia System," Surg. For. 39, 507-509 (1988).

[17] M. S. Grady, M. A. Howard, J. A. Molloy, R. C. Ritter, E. G. Quate, G. T. Gillies, "Preliminary Experimental Investigation of *in vivo* Magnetic Manipulation: Results and Potential Applications in Hyperthermia," Med. Phys. 16, 263 - 272 (1989).

[18] M. S. Grady, M. A. Howard, J. A. Molloy, R. C. Ritter, E. G. Quate, G. T. Gillies, "Nonlinear Magnetic Stereotaxis: Three-Dimensional, *in vivo* Magnetic Manipulation of a Small Object in Canine Brain," Med. Phys. 17, 402-415 (1990).

[19] E. G. Quate, K. G. Wika, M. A. Lawson, G. T. Gillies, R. C. Ritter, M. S. Grady, M. A. Howard, "Goniometric Motion Controller for the Superconducting Coil in a Magnetic Stereotaxis System," IEEE Trans. Biomed. Engr. BME-38, no. 9, 899-905 (Sept. 1991).

[20] J. A. Molloy, R. C. Ritter, W. C. Broaddus, M. S. Grady, M. A. Howard, E. G. Quate, G. T. Gillies, "Thermodynamics of Moveable Inductively Heated Seeds for the Treatment of Brain Tumors," Med. Phys. 18, 794-803 (1991).

[21] G. T. Gillies, R. C. Ritter, W. C. Broaddus, M. S. Grady, M. A. Howard, R. G. McNeil, "Magnetic Manipulation Instrumentation for Medical Physics Research," Rev. Sci. Instrum. 65, no. 3, 533-562 (1994).

[22] R. C. Ritter, M. S. Grady, M. A. Howard, G. T. Gillies, "Magnetic Stereotaxis: Computer-Assisted, Image-Guided remote Movement of Implants in the Brain," Innov. Tech. Biol. Méd. 13, 437-449 (1992).

[23] S. Earnshaw "On the Nature of the Molecular Forces which Regulate the Constitution of the Luminiferous Ether" Trans. Cambridge Philos. Soc. 7, 97-112 (1842).

[24] J. C. Maxwell, *A Treatise on Electricity and Magnetism*, 3rd. ed. (Oxford, London: Clarendon Press, 1892).

[25] D. C. Meeker, E. H. Maslen, R. C. Ritter, F. M. Creighton, "Optimal Realization of Arbitrary Forces in a Magnetic Stereotaxis System", IEEE Trans. Magn. 32, 320-328 (1996).

Footnotes

\* $H_{L,rr}$ is obtained from $H_L$ by retaining only the first $r$ rows and $r$ columns. Likewise, $\nabla g_{mr}$ is obtained from $\nabla g$ by keeping the elements in the first $r$ columns while retaining the $m$ rows. It follows that $\nabla(g_{mr})^T = \nabla g^T_{rm}$.

† For those problems in which a minimum is sought, $f(\mathbf{x})$ is simply replaced by $-f(\mathbf{x})$.

‡ Note that constraints of the form $\mathbf{t}(\mathbf{x}) \le \mathbf{u}$ can be rewritten as $-\mathbf{t}(\mathbf{x}) \ge -\mathbf{u}$. Thus, when combined with the constraints $\mathbf{d}(\mathbf{x}) \ge \mathbf{c}$, we form the set $\overline{\mathbf{d}}(\mathbf{x}) \ge 0$ where $$\overline{\mathbf{d}}^T(\mathbf{x}) = \{-\mathbf{t}^T(\mathbf{x}) + \mathbf{u}^T, \mathbf{d}^T(\mathbf{x}) - \mathbf{c}^T\}.$$

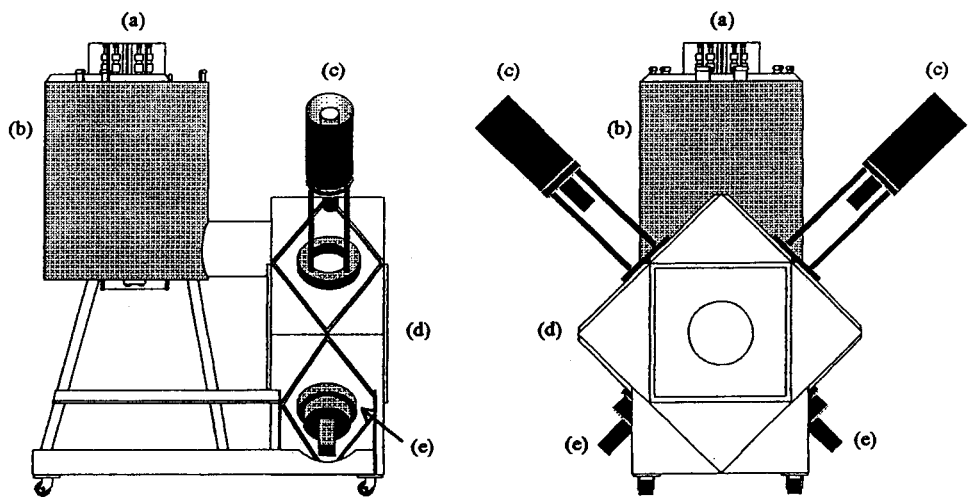
(a) Coil Leads from Power Supplies
(b) Dewar for Liquid Nitrogen and Liquid Helium
(c) Magnetic Shields (X-Ray Fluoroscopes Inside)
(d) Helmet Cryostat
(e) Charge-Coupled Device Cameras

Figure 1. Components of the Magnetic Stereotaxis System for magnetic neurosurgery.

Figure 2. MSS navigation is done by orienting the implant's moment (m) in the direction of a guiding magnetic field. A displacement is made by exerting a force at one end of the guide wire which is attached at the other end to the magnetic implant. The resulting motion occurs in small steps (~3mm), moving the implant deeper into the brain along a predetermined path. Surrounding the push wire and implant is a catheter which serves as a means of providing drug therapy or inserting biopsy and pallidotomy tools.

Figure 3. Histograms depicting the distributions of (a) the force for a moment of $0.04 \, A \cdot m^2$, (b) the maximum current element, (c) the root-mean-square current (equivalent to the square root of the current metric), and (d) the angle between the force and magnetic field for 13 125 000 cases (1000 random field orientations for 13 125 tabulated positions) and for a 0.3T field. In all cases, the positions were restricted according to $$-60 \text{ mm} < x < 60 \text{mm} \, , \, -60 \text{ mm} < y < 60 \text{mm} \, , \, -30 \text{ mm} < z < 70 \text{mm}$$

and incremented at 0.5 cm steps in all directions. The mean plus and minus one standard deviation (i.e., $\pm\sigma$) are indicated on each plot.

APPENDIX "C"

CHAPTER 3

GENERATION OF A MAGNETIC FIELD FOR A CIRCULAR COIL OF DISTRIBUTED CURRENT

The correct characterization of the magnetic field and the field derivatives (as generated by the coils of the MSS) is critical to the safe and successful operation of the control algorithms. This chapter details the calculation of the magnetic field for the volume of interest in the MSS as well as the formalism with which the mathematical model is constructed. The behavior of the magnetic field only requires high accuracy over the region occupied by the brain in order for the implant-guidance algorithms (discussed in Chapters 5 and 6) to operate correctly. For the purposes of the MSS, a 20 cm diameter sphere located at the center of the helmet-cryostat is more than sufficient in this regard.

3-1 Solitary Filamentary Coil

The accurate description of the magnetic field for a coil of distributed current, assuming that the field is not measured so far away from the coil that the dipole approximation adequately predicts the magnetic field, is obviously dependent on the physical dimensions of the coil. As was previously stated in Chapter 2, the six coils of the MSS consist of two designs. Four coils form the x- and y- coil pairs and can be said to be identical. The remaining two coils make up the z-coil pair and are identical only to each other. Figure 3-1 depicts the coil arrangement in the MSS. As can be seen from the physical parameters

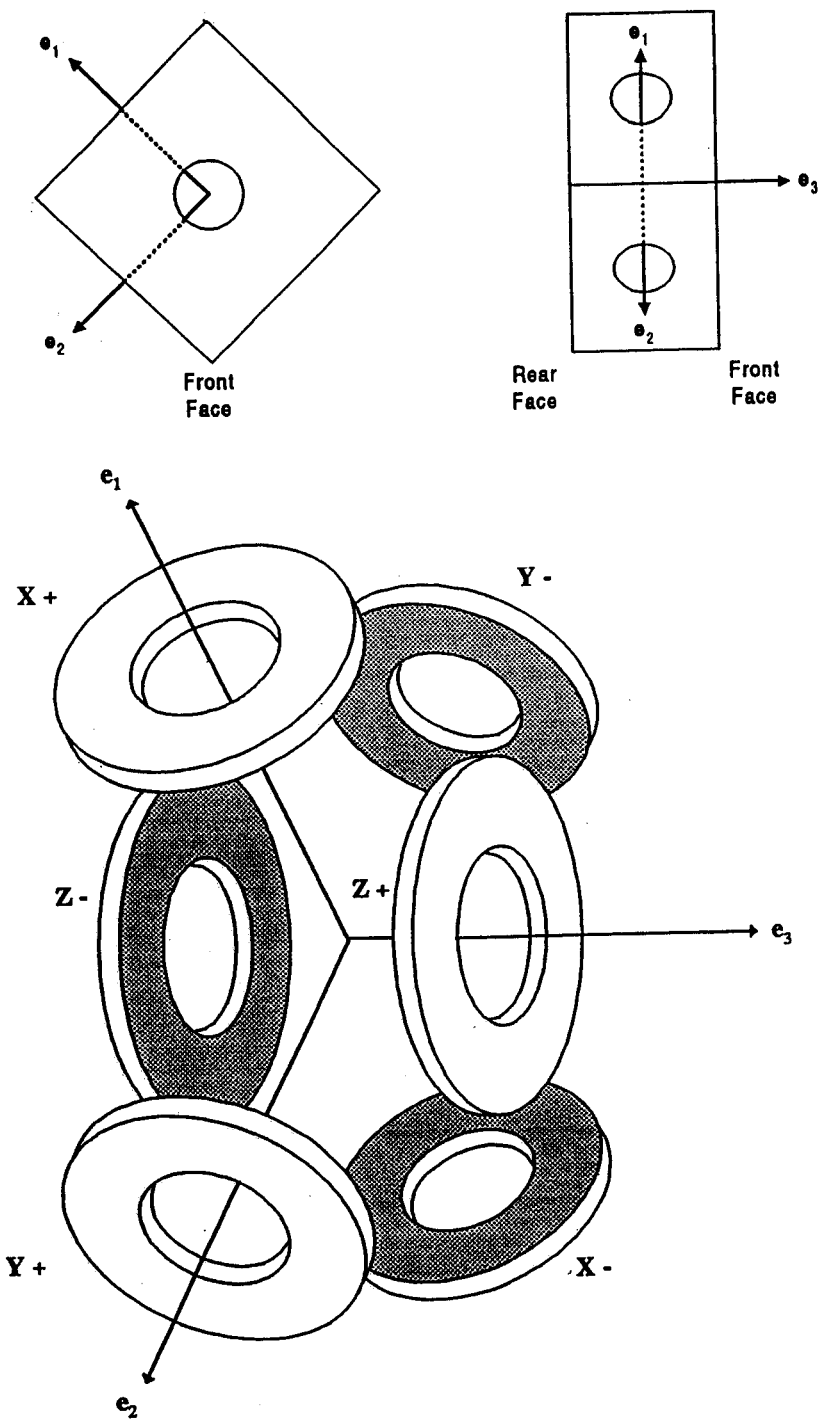
FIG. 3-1. Relationship between the coil locations and helmet coordinates, where helmet coordinates is denoted by $e_1$, $e_2$, and $e_3$. Note that the origin of helmet coordinates is located at the intersection of midplane axes for the x-, y-, and z- coil pairs.

listed in Table 2-1, the coils possess a finite cross-sectional area made up of thousands of copper encased (i.e., thermally lagged) NbTi filaments. Each actuating coil can therefore be seen as carrying an approximately uniform current density throughout the cross-sectional area.

We begin by considering the case of a solitary filament as given by Hart [51]. Constructing the current-independent (i.e., units of T/A ) radial and axial field components (i.e., $b_\rho$ and $b_\ell$, respectively) for a circular loop, we find from the Biot-Savart law that $$\left.\begin{aligned} b_\rho &= -\frac{\mu_o}{2\pi} \int_0^\pi \frac{\ell R \cos\phi}{\left(R^2 + \rho^2 + \ell^2 - 2R\rho \cos\phi\right)^{3/2}} d\phi \\ b_\ell &= \frac{\mu_o}{2\pi} \int_0^\pi \frac{\left(R^2 - R\rho \cos\phi\right)}{\left(R^2 + \rho^2 + \ell^2 - 2R\rho \cos\phi\right)^{3/2}} d\phi \end{aligned}\right\} \quad (3\text{-}1)$$

where $\mu_o$ is the permeability of free space and $\ell$, $\phi$, $R$, and $\rho$ are defined in Fig. 3-2. Since the induction is linear with respect to the $I$, the radial and axial magnetic field components, $B_\ell$ and $B_\rho$, are given by $$\left.\begin{aligned} B_\rho &= I\, b_\rho \\ B_\ell &= I\, b_\ell \end{aligned}\right\} \quad (3\text{-}2)$$

While forms other than those of Eq. (3-1) can be found for $b_\rho$ and $b_\ell$ which make use of the azimuthal symmetry of the loop, no closed form solutions exist for off-axis points. It is a matter of convenience that the form of the magnetic field in Eq. (3-1) is used in the numerical integration routines, for which it is better suited than other forms.

For the case of on-axis field evaluation (i.e., $\rho = 0$), the components of Eq. (3-1) reduce to

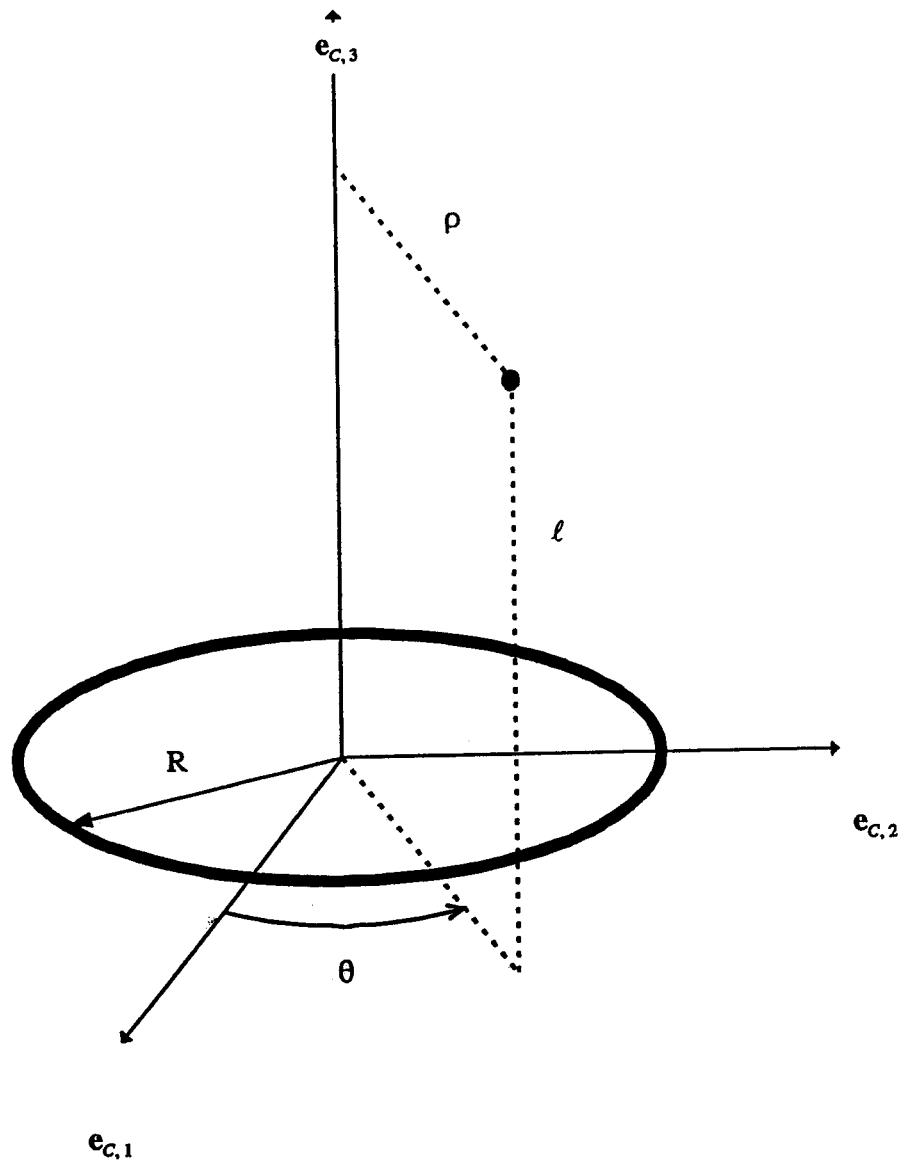
FIG. 3-2. Filamentary circular coil in cylindrical coordinates with respect to a Cartesian reference frame (denoted by the unit vectors $e_{c,1}$, $e_{c,2}$, and $e_{c,3}$).

Table 3-1. On-Axis Calculations of Axial Magnetic Induction*

| $\ell$ (cm) | Numerically-Integrated $B_\ell(T)$ | Exact $B_\ell(T)$ |
|---|---|---|
| 0.0 | 3.1416 | 3.1416 |
| 10.0 | 2.2479 | 2.2479 |
| 20.0 | 1.1107 | 1.1107 |
| 30.0 | 0.5362 | 0.5362 |
| 40.0 | 0.2810 | 0.2810 |
| 50.0 | 0.1609 | 0.1609 |
| 60.0 | 0.0993 | 0.0993 |
| 70.0 | 0.0651 | 0.0651 |
| 80.0 | 0.0448 | 0.0448 |
| 90.0 | 0.0321 | 0.0321 |

*Note that the numerically-integrated fields are calculated from Eq. (3-1) with $\rho = 0$ and are compared with the exact values as calculated from Eq.(3-3). In all cases, the radius of the filament is taken to be 20 cm and the current set to $10^6$ A. The numerical integration is executed via Simpson's method with 50 iterations [52]. Also note that for $\ell = 0$, $B_\ell = \pi$ (in Tesla).

$$\left. \begin{array}{l} b_\rho = 0 \\ b_\ell = \dfrac{\mu_o}{2} \dfrac{R^2}{\left(R^2 + \ell^2\right)^{3/2}} \end{array} \right\} \qquad (3\text{-}3)$$

While the value of the field given by Eq. (3-3) can be calculated exactly, the more general off-axis case is best solved numerically. Thus, Eq. (3-3) offers a quick check to the computed field for the on-axis case. (See Table 3-1.)

Having established a test case for the numerical-integration techniques that are applied in Table 3-1, more general cases can be considered. Table 3-2 reports several such cases where the filament radius is set to 20 cm, the current is set to $10^6$ A, and the number of numerical-integration iterations is set to 50. Of all the table entries, thirteen of the calculated field components are in exact agreement with Hart. The discrepancy for two of the three remaining entries can be accounted for by round-off error in the numerical integration routines. For example, in the case of the position (5.0 cm, 10.0 cm), $B_\rho$ is calculated at 0.354143 T for 25 iterations of the numerical integration. At 5000

Table 3-2. Comparison of Generated Fields for Off-Axis Points of a Filament Coil Against Published Data.*

| Position ($p$, $\ell$) (cm) | Calc. $B_p$ (T) | Calc. $B_\ell$ (T) | Hart $B_p$ (T) | Hart $B_\ell$ (T) |
|---|---|---|---|---|
| ( 10.0 , 0.0 ) | 0.0000 | 3.9132 | 0.0000 | 3.9132 |
| ( 16.0 , 0.0 ) | 0.0000 | 7.2675 | 0.0000 | 7.2676 |
| ( 25.0 , 0.0 ) | 0.0000 | -2.4802 | 0.0000 | -2.4802 |
| ( 5.0 , 10.0 ) | 0.3542 | 2.2439 | 0.3542 | 2.2440 |
| ( 10.0 , 10.0 ) | 0.8084 | 2.1729 | 0.8084 | 2.1729 |
| ( 25.0 , 10.0 ) | 1.1783 | 0.0222 | 1.1783 | 0.0222 |
| ( 5.0 , 20.0 ) | 0.2060 | 1.0711 | 0.2064 | 1.0711 |
| ( 10.0 , 20.0 ) | 0.3944 | 0.9477 | 0.3944 | 0.9477 |

*Published data is taken from Hart [51]. For all cases, the filament radius is 20 cm and the fields are evaluated at $10^6$ A. For the numerical integration, the number or iterations for field calculation is set to 50.

iterations, the field is found to be 0.354163 T, a difference of only 0.006%. However, rounding to four significant figures yields 0.3541 T for 25 iterations and 0.3542 T for 5000 iterations, a difference of 0.03%.

It is interesting to note the discrepancy in $B_p$ for the position (5.0 cm, 20 cm) which is nearly 0.1%. Increasing the iterations for the numerical-integration algorithms used in the evaluation of Eq. (3-1) to 5000 yields no significant convergence to the value reported by Hart. Assuming that the discrepancy might be accounted for by the machine compiler or the computer code containing the integration routines, a HP-48G scientific calculator was used as an independent check to the calculated field values. For the case at hand, the HP-48G agreed with the calculated values (at 5000 iterations) to eleven decimal places. Since it is unlikely that two independent sources could possess the same coding bug, the value reported by Hart should be assumed to be incorrect at that level of precision. Table 3-3 details the rise in accuracy of the calculated values as the iterations are increased at the sample position (5.0 cm, 10.0 cm).

Table 3-3. Comparison Between Number of Iterations and Field Inaccuracy*

| Iterations | Calculated $B_\rho$ (T) | Calculated $B_\ell$ (T) | Inaccuracy ($B_\rho$) | Inaccuracy ($B_\ell$) |
|---|---|---|---|---|
| 10 | 0.35153201 | 2.24161326 | 0.74% | 0.1% |
| 20 | 0.35384768 | 2.24364313 | 0.09% | 0.01% |
| 200 | 0.35416228 | 2.24392741 | 0.0001% | < 0.0001% |
| 2000 | 0.35416259 | 2.24392770 | < 0.0001% | < 0.0001% |
| 20000 | 0.35416259 | 2.24392769 | < 0.0001% | < 0.0001% |

*All calculations are done for the point $(\rho, \ell) = (5.0 \text{ cm}, 10.0 \text{ cm})$. Inaccuracy is defined with respect to the "exact" value. For the present purposes, exact fields are assumed to be generated by 60,000 numerical iterations.

3-2 Field Evaluation for a Distributed Current

Having detailed the calculation of the magnetic field for a single filament coil, we turn our attention to the field generated by the coils of the MSS. Unlike the filament coil, the superconducting actuators of the MSS possess definite thickness and width (see Table 2-1). Incorporating these physical aspects of the coils into Eq. (3-1) proves to be straightforward providing we approximate the current density, $J$, as being evenly distributed over the cross-sectional width of the coil, which is valid considering that the electromagnetic coil is composed of thousands of insulated windings (see Fig. 3-3). We recall that the relationship between $I$ and $J$ is given by $$N I = \int_s \mathbf{J} \cdot \mathbf{n} \, da = J \int_s da = J A \tag{3-4}$$

where $\mathbf{J}$ is oriented in the direction of the current, $N$ is the number of filament windings, and $A$ is the cross-sectional area of the coil as listed in Table 2-1. From Eq. (3-4), it follows that $$J = \frac{N I}{A} \tag{3-5}$$

Using Eq. (3-5), Eq. (3-1) can be modified to incorporate the width of the coil, $W$, and the

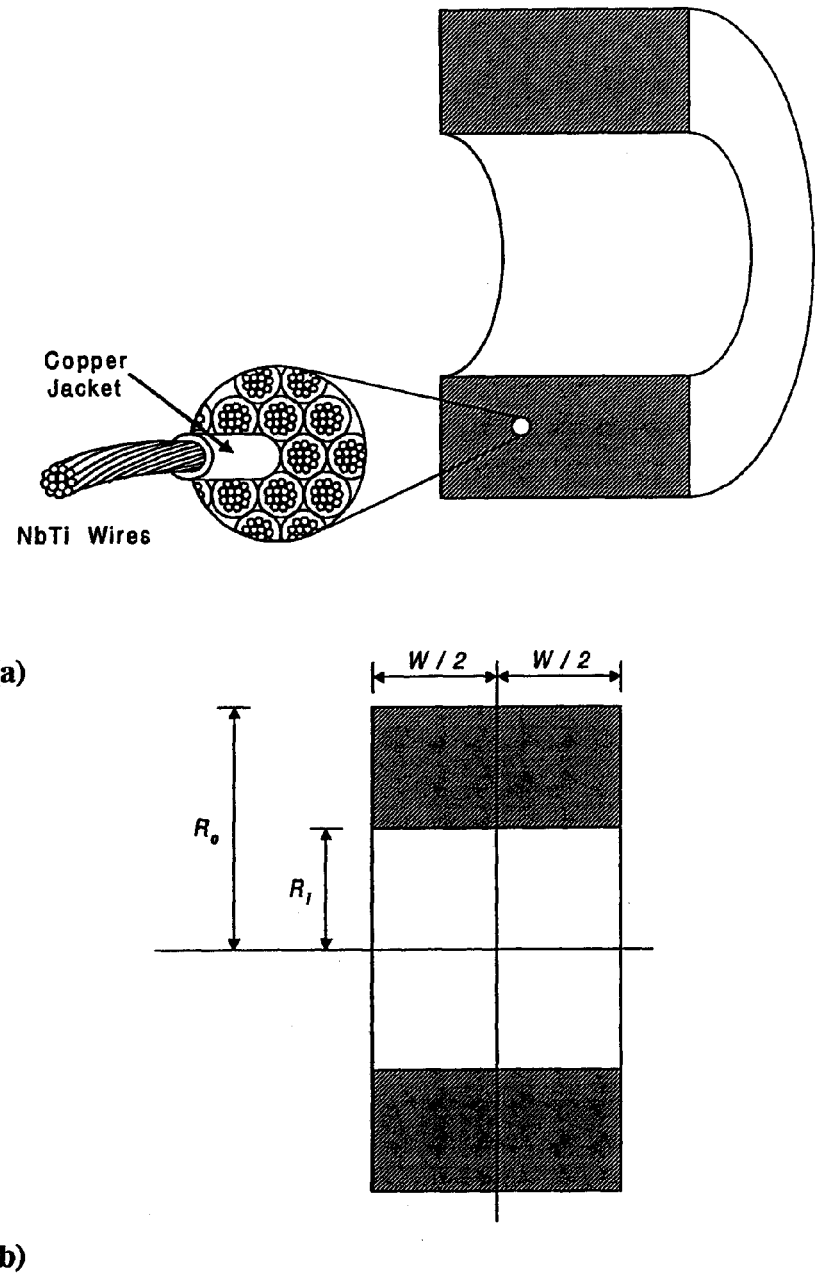

FIG. 3-3. Depiction of (a) the cross section (shaded) and (b) the width, $W$, and inner and outer radii, $R_i$ and $R_o$, respectively, of a circular coil. Figure (a) also depicts a cross-sectional element consisting of the copper encased (i.e., thermally-lagged) NbTi windings that carry the current. The relatively high number of windings allows the current density to be approximated as being uniform.

Using Eq. (3-5), Eq. (3-1) can be modified to incorporate the width of the coil, $W$, and the inner and outer radii of the coil, $R_i$ and $R_o$, respectively:

$$\left. \begin{aligned} b_p &= -\frac{\mu_o}{2\pi A} \int_{R_i}^{R_o} dr \int_{\ell-W/2}^{\ell+W/2} d\ell' \int_0^\pi \frac{\ell' r \cos\phi}{\left(r^2 + \rho^2 + \ell'^2 - 2r\rho\cos\phi\right)^{3/2}} d\phi \\ b_\ell &= \frac{\mu_o}{2\pi A} \int_{R_i}^{R_o} dr \int_{\ell-W/2}^{\ell+W/2} d\ell' \int_0^\pi \frac{\left(r^2 - r\rho\cos\phi\right)}{\left(r^2 + \rho^2 + \ell'^2 - 2r\rho\cos\phi\right)^{3/2}} d\phi \end{aligned} \right\} \quad (3\text{-}6)$$

Furthermore, the cross-sectional area is given by $$A = W(R_o - R_i) \quad (3\text{-}7)$$

Equation (3-6) can be somewhat simplified by carrying out the integration with respect to $r$ and $\ell'$, reducing it to $$b_p = -\frac{\mu_o}{2\pi A} \int_0^\pi \cos\phi \left[ \sqrt{r^2 + \rho^2 + \ell'^2 - 2r\rho\cos\phi} \right]_{\ell'=\ell-W/2}^{\ell'=\ell+W/2} \Bigg|_{r=R_i}^{r=R_o} d\phi$$

$$-\frac{\mu_o}{2\pi A} \int_0^\pi \left[ \rho \cos^2\phi \, \sinh^{-1}\!\left( \frac{r - \rho\cos\phi}{\sqrt{\ell'^2 + \rho^2 \sin^2\phi}} \right) \right]_{\ell'=\ell-W/2}^{\ell'=\ell+W/2} \Bigg|_{r=R_i}^{r=R_o} d\phi \quad (3\text{-}8a)$$

$$b_\ell = \frac{\mu_o}{2\pi A} \int_0^\pi \left[ \ell' \sinh^{-1}\!\left( \frac{r - \rho\cos\phi}{\sqrt{\ell'^2 + \rho^2 \sin^2\phi}} \right) \right]_{\ell'=\ell-W/2}^{\ell'=\ell+W/2} \Bigg|_{r=R_i}^{r=R_o} d\phi$$

$$-\frac{\mu_o}{2\pi A} \int_0^\pi \left[ \frac{\rho}{\sin\phi} \tan^{-1}\!\left( \frac{\ell'}{\rho\sin\phi} \frac{r - \rho\cos\phi}{\sqrt{r^2 + \rho^2 + \ell'^2 - 2r\rho\cos\phi}} \right) \right]_{\ell'=\ell-W/2}^{\ell'=\ell+W/2} \Bigg|_{r=R_i}^{r=R_o} d\phi \quad (3\text{-}8b)$$

A special case of Eq. (3-8) is for on-axis field evaluations (i.e. $\rho = 0$) for which Eqs. (3-8a) and (3-8b) reduce to $$\left. \begin{array}{l} b_p = 0 \\ b_t = \dfrac{\mu_o}{2A} \ell' \sinh^{-1}\left(\dfrac{r}{\ell'}\right)\Big|_{\ell'=\ell-W/2}^{\ell'=\ell+W/2}\Big|_{r=R_i}^{r=R_f} \end{array} \right\}$$ (3-9)

Though Eq. (3-8b) is superior to other forms for numerical integration, it remains problematic at the singularities $\phi = 0$ and $\phi = \pi$. One possible means of avoiding these singularities is to integrate $b_t$ in Eq. (3-6) with respect to either $r$ or $\ell'$ such that the singularity no longer remains, which leaves a double integral to evaluate numerically. However, it is generally true that numerical integration of functions of several variables (i.e., functions of dimension greater than one) are theoretically and computationally difficult [52]. The region of integration in the $N$-dimensional space is defined by a potentially complicated $N$-1 dimensional boundary. In contrast to this, the boundary of a one-dimensional integral consists of only an upper and lower boundary. Another penalty of multiple numerical integrations is in the increased time of computation. For every iteration with respect to one integral, the remaining integral must compute through all of its designated iterations. As an example, if each integral set at 1000 iterations, the double integration results in $(1000)^2$ computations. Translated into time of processing, the double integration takes 1000 times longer to compute than a single integration.

As another approach, we turn our attention to the current distribution over the coil's cross-sectional area, approximating the current density as being composed of discrete filaments, each regularly spaced from one another and sharing the same current density [36]. It is important to note that the filaments merely approximate the distributed current and are not necessarily identified as the actual coil windings of the actuators. For example, if a coil possesses 1000 windings and the cross-sectional area is approximated to consist of 10 filaments, then each filament represents 100 windings providing the filaments are evenly spaced. While it may seem logical to equate the filaments with the windings, it is shown that far fewer filaments are more than sufficient to describe the magnetic induction.

By approximating the cross-sectional area by filament coils, we need only to reformulate Eq. (3-8b) since there are no singularities in Eq. (3-8a):

$$b_\ell = \frac{\mu_o}{2\pi} \sum_n \left( \int_0^\pi \frac{(R_n^2 - R_n \rho \cos\phi)}{\left(R_n^2 + \rho^2 + (\ell + \Delta\ell_n)^2 - 2R_n \rho \cos\phi\right)^{3/2}} d\phi \right) \qquad (3\text{-}10)$$

In Eq. (3-10), $n$ is summed over all the filaments, $R_n$ is identified as each filament's radius, and $\Delta\ell_n$ is the axial location of each filament's midplane with respect to the coil's midplane. Figure 3-4 depicts several examples of a current distribution approximated by filament loops.

Table 3-4 shows that for off-axis positions, the discrepancy in $b_\ell$ is at most 0.18% from those values predicted by Hart for a coil approximated by four loops and four turns (i.e., $n = 16$) in Eq. (3-10). However, the evaluation of $b_\rho$ via Eq. (3-8a), in which a filament approximation is not necessary, yields nearly exact matches to Hart up to four decimal places in Table 3-4. Table 3-5 details the calculation of $B_\ell$ for on-axis locations.

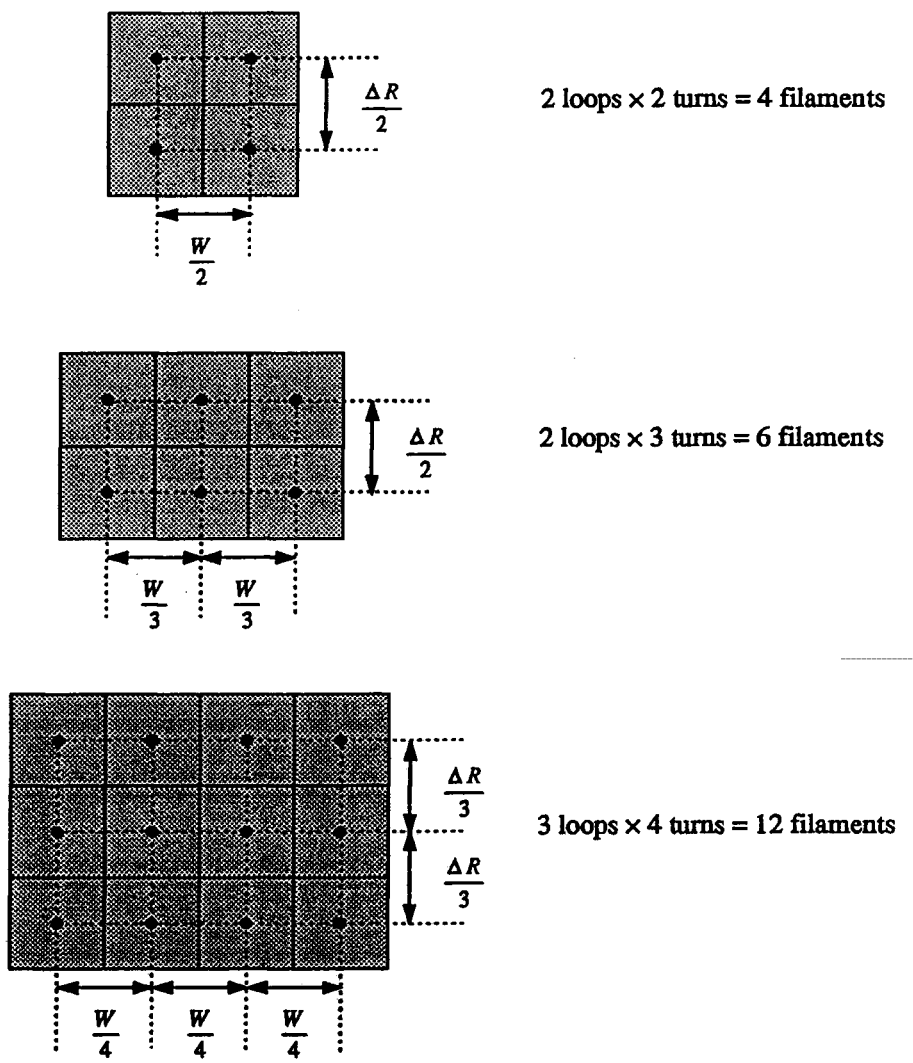

FIG. 3-4. Filament approximation for circular coils. The shaded region represents the cross-sectional area of each coil, which is approximated by a uniform current density and where the area's normal vector is in the direction of the current. Each coil has a width $W$ and a thickness $\Delta R$, where $\Delta R$ is the difference between inner and outer coil radii. The approximating filaments are depicted as the black dots in the shaded regions and are regularly spaced. While the filaments approximate a square area of identical current density in the cases above, other shaped areas may be assigned to more accurately approximate the geometry of the coils in question.

Table 3-4. Comparison of Off-Axis Fields with Hart for a Distributed Current*

| Position (ρ,ℓ) (cm) | Calc. $B_ρ$(T) | Calc. $B_ℓ$(T) | Hart $B_ρ$(T) | Hart $B_ℓ$(T) |
|---|---|---|---|---|
| (5.0,0.0) | 0.0000 | 1.4320 | 0.0000 | 1.4316 |
| (5.0,5.0) | 0.1375 | 1.2640 | 0.1376 | 1.2638 |
| (5.0,10.0) | 0.1685 | 0.9139 | 0.1685 | 0.9140 |
| (5.0,15.0) | 0.1299 | 0.6024 | 0.1298 | 0.6025 |
| (5.0,20.0) | 0.0850 | 0.3911 | 0.0850 | 0.3912 |
| (5.0,25.0) | 0.0532 | 0.2586 | 0.0532 | 0.2587 |
| (5.0,30.0) | 0.0335 | 0.1760 | 0.0335 | 0.1760 |
| (10,0.0) | 0.0000 | 1.7328 | 0.0000 | 1.7320 |
| (10.0,5.0) | 0.3842 | 1.4056 | 0.3842 | 1.4053 |
| (10.0,10.0) | 0.3875 | 0.8589 | 0.3875 | 0.8591 |
| (10.0,15.0) | 0.2574 | 0.5201 | 0.2574 | 0.5203 |
| (10.0,20.0) | 0.1582 | 0.3325 | 0.1582 | 0.3325 |
| (10.0,25.0) | 0.0974 | 0.2224 | 0.0974 | 0.2224 |
| (10.0,30.0) | 0.0613 | 0.1543 | 0.0613 | 0.1543 |

*For comparison with Hart, the coil has an inner radius of 15 cm, an outer radius of 20 cm and a width of 10 cm. The actuating current is $10^6$ A and the iteration number for numerical integration was set to 50. $B_ρ$ is calculated via Eq. (3-8a). For $B_ℓ$, the current density is approximated by 16 filament coils, four loops and four turns, and is calculated by Eq. (3-10).

Table 3-5. Comparison of On-Axis Fields with Hart for a Distributed Current*

| Position (ρ,ℓ) (cm) | Calc. $B_ℓ$(T) | Hart $B_ℓ$(T) | Exact $B_ℓ$(T) |
|---|---|---|---|
| (0.0,0.0) | 1.3546 | 1.3543 | 1.3543 |
| (0.0,5.0) | 1.2202 | 1.2200 | 1.2200 |
| (0.0,10.0) | 0.9202 | 0.9203 | 0.9203 |
| (0.0,15.0) | 0.6253 | 0.6254 | 0.6254 |
| (0.0,20.0) | 0.4105 | 0.4106 | 0.4106 |
| (0.0,25.0) | 0.2713 | 0.2713 | 0.2713 |

*For comparison with Hart, the coil has the same coil and iteration specifications as that of Table 3-4. Equation (3-9) is used in the calculations of $B_ℓ$ where $B_ρ$ = 0 at all points. The exact values of the field are calculated for 10,000 iterations of the numerical integration.

These values are not calculated from the filament approximation scheme since Eq. (3-9) remains valid. The off-axis error in $B_ℓ$ is, undoubtedly, a result of approximating the current distribution as finite current filaments. We note that in Table 3-5, the error at 50 iterations with Hart is up to 0.18%; however, the calculated values are in much closer agreement with those values taken to be exact. In fact, the calculated values are no more than 0.025% from the exact value whereas Hart differs by nearly 0.2%.

It is interesting to note that increasing the number of approximating filaments does little to reduce the discrepancy with the fields as given by Hart. For instance, increasing the number of filaments such that there are 11 loops and 11 turns (i.e., 121 filaments) yields an error slightly less than 0.05%, which is not significantly better than that of a 16 filament approximation.

Table 3-6 details a case analysis of the effect of increasing the number of approximating filaments and the number of iterations versus the inaccuracy of $B_t$. Table 3-7 details the effect of increasing the number of iterations with respect to the inaccuracy, where the filament approximation is not necessary for the calculation of $B_p$. Note that the inaccuracy levels out for the $B_t$ component (Table 3-6), whereas the inaccuracy for $B_p$ Table 3-6. Comparison Between Number of Iterations and the Inaccuracy in $B_t$ for Filament Approximation*

| (Loops x Turns) | Iterations | Calc. $B_t(T)$ | Inaccuracy ($B_t$) |
|---|---|---|---|
| (3x3) | 10 | 0.91298020 | 0.1% |
|  | 20 | 0.91379100 | 0.02% |
|  | 200 | 0.91390425 | 0.005% |
|  | 2000 | 0.91390443 | 0.005% |
| (7x7) | 10 | 0.91290152 | 0.1% |
|  | 20 | 0.91371262 | 0.03% |
|  | 200 | 0.91382587 | 0.01% |
|  | 2000 | 0.91382623 | 0.01% |
| (35x35) | 10 | 0.91228134 | 0.2% |
|  | 20 | 0.91309152 | 0.04% |
|  | 200 | 0.91320780 | 0.05% |
|  | 2000 | 0.91320745 | 0.05% |

*All field values are compared for the point $(\rho, \ell) = (5.0 \text{ cm}, 10.0 \text{ cm})$ where inaccuracy is defined with respect to the "exact" value. For the present purposes, exact fields are assumed to be generated by 10,000 numerical iterations at a (35x35) filament approximation.

Table 3-7. Comparison Between Number of Iterations and the Inaccuracy in $B_\rho$ for Filament Approximation*

| Iterations | Calc. $B_\rho$ (T) | Inaccuracy ($B_\rho$) |
|---|---|---|
| 10 | 0.16740611 | 0.7% |
| 20 | 0.16838184 | 0.08% |
| 200 | 0.16851377 | 0.02% |
| 2000 | 0.16851404 | 0.002% |

*All field values compared for the point $(\rho, \ell)$ = (5.0 cm, 10.0 cm) where inaccuracy is defined with respect to the exact value as in Table 3-6.

decreases continually as the number of iterations are increased (Table 3-7). This difference between the inaccuracy of the two field components is due to the fact that for $B_\ell$, the filament coils become the dominate source of error. Since the filament approximation is not necessary for $B_\rho$, no such error is expected to occur.

As can be seen in Table 3-6, the inaccuracy can always be decreased for a fixed number of iterations by increasing the number of approximating filaments. Going from 9 filaments (i.e., a 3x3 filament approximation) to 49 (7x7) decreases the inaccuracy by a factor of 16. Going from 49 (7x7) filaments to 121 (11x11) decreases the inaccuracy by a factor of 2. Unfortunately, the cost of higher accuracy is longer computation time. For high accuracy, the processing time will be proportional to the square of the increase in accuracy. However, given that the accuracy of an (11x11) filament-approximated cross section is sufficient in the field calculations, the effective processing time is about a factor of 10 faster at 1000 iterations than numerically evaluating the double integral of Eq. (3-6).

3-3 Calculation of Field Gradients

The calculation of the gradients of the magnetic field can be performed by one of two methods. The first approach is to differentiate Eq. (3-6) with respect to $\rho$ and $\ell$ and then to integrate numerically over the cross-sectional area. If singularities arise in the evaluation of the derivatives, as they did for $b_\ell$, then the current density should again be approximated by individual filaments.

The other approach to the problem is to construct a table that maps out a data plane for the two types of coils. This plane would tabulate values of $\ell$ versus $\rho$ at regularly spaced intervals in the plane (see Fig 3-5). Since the derivatives can be specified at the plane's boundaries, the magnetic field can be found at any point in the region via a two-dimensional bi-cubic spline interpolation [52]. From the spline information, the derivatives can be constructed up to third order. The third order terms are, however, the limit of the spline approximation since they are assumed to be constant between any two tabulated points. The reader is encouraged to consult *Numerical Recipes in C* by Press *et al.* for a more detailed description on the mechanics of spline-interpolation.

The choice between the two methods is dictated by the importance of processing time versus accuracy. If speed is of the essence and only terms up to second order need to be considered, then the bi-cubic spline-interpolation method promises adequate results in a time interval that is, generally, much faster than carrying out the numerical integrations for the field and field-derivative terms. The only requirement of the spline is the construction of the data table. Depending on the degree of accuracy in the tabulated magnetic field

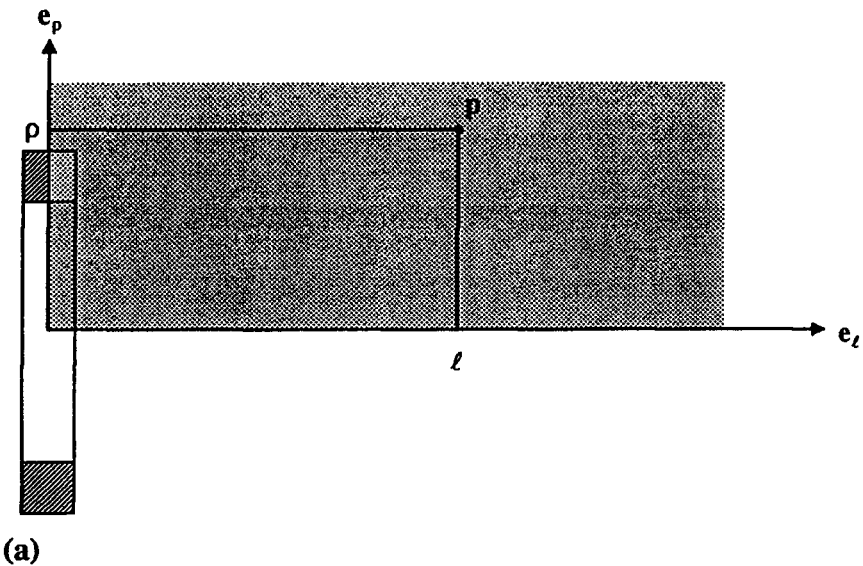
(a)
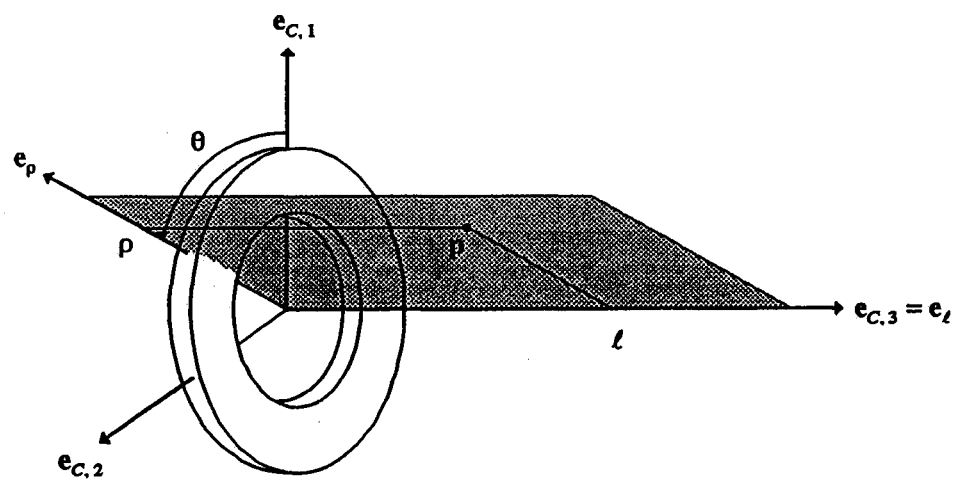
(b)
FIG. 3-5. Depiction of the data plane (shaded) in which the field and field partials are generated. The field information is calculated in cylindrical coordinates as shown in (a). In (b), the data plane (with the coil's midplane centered at the origin) is related to coil coordinates (discussed in Chapter 4). $e_{c,1}$, $e_{c,2}$, $e_{c,3}$, $e_\rho$, and $e_\ell$ are unit vectors in both figures.

components, the construction of the table can take a significant amount of time. However, once created and written to a file, there is no need for recalculating the table for future field evaluations. The information can be read from a stored table and then interpolated to give the field and field derivatives at any position contained within the table. However, if a high degree of theoretical accuracy is desired or derivatives greater than second order are necessary, then numerical integration is required for all the pertinent integral equations for the point in question.

The bi-cubic spline interpolation scheme has been adopted by the MSS, proving to be a fast and reliable means of calculating the field information over the region of interest. Since the interpolation is built upon magnetic field data tables for the two coil types, the range of the interpolation is limited to the sampling size of the data tables. Outside this range, the spline-interpolation machinery breaks down. Thus, the data tables are large enough to accommodate the entire volume of the brain, but do not describe the magnetic field outside this volume. Currently, the MSS accurately generates all pertinent field information for a 20 cm diameter sphere located at the center of the cryostat, which is more than sufficient to enclose the volume of the typical adult brain. To describe the magnetic field, the force, and the change in gradient at a specific implant position inside the helmet (all of which are required for implant control), only fields through the second-order derivatives are required for the MSS. Figures 3-6 through 3-11 detail the behavior of the magnetic field and the directional derivatives for the two coil types as functions of

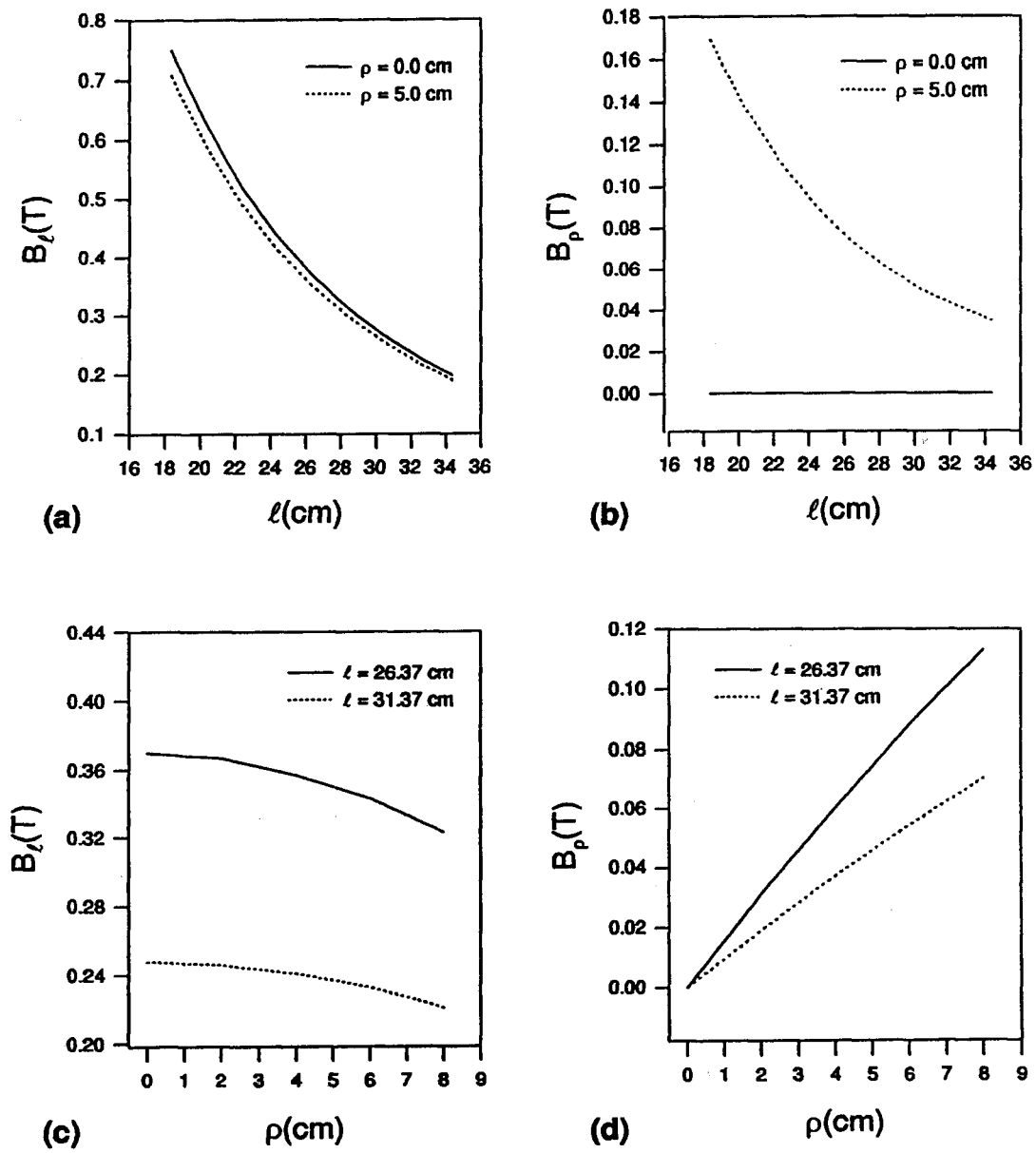
FIG. 3-6. Variation of the magnetic field terms with respect to the axial and radial components of the data plane for the type-1 coil (i.e., the x- and y-coil pairs).

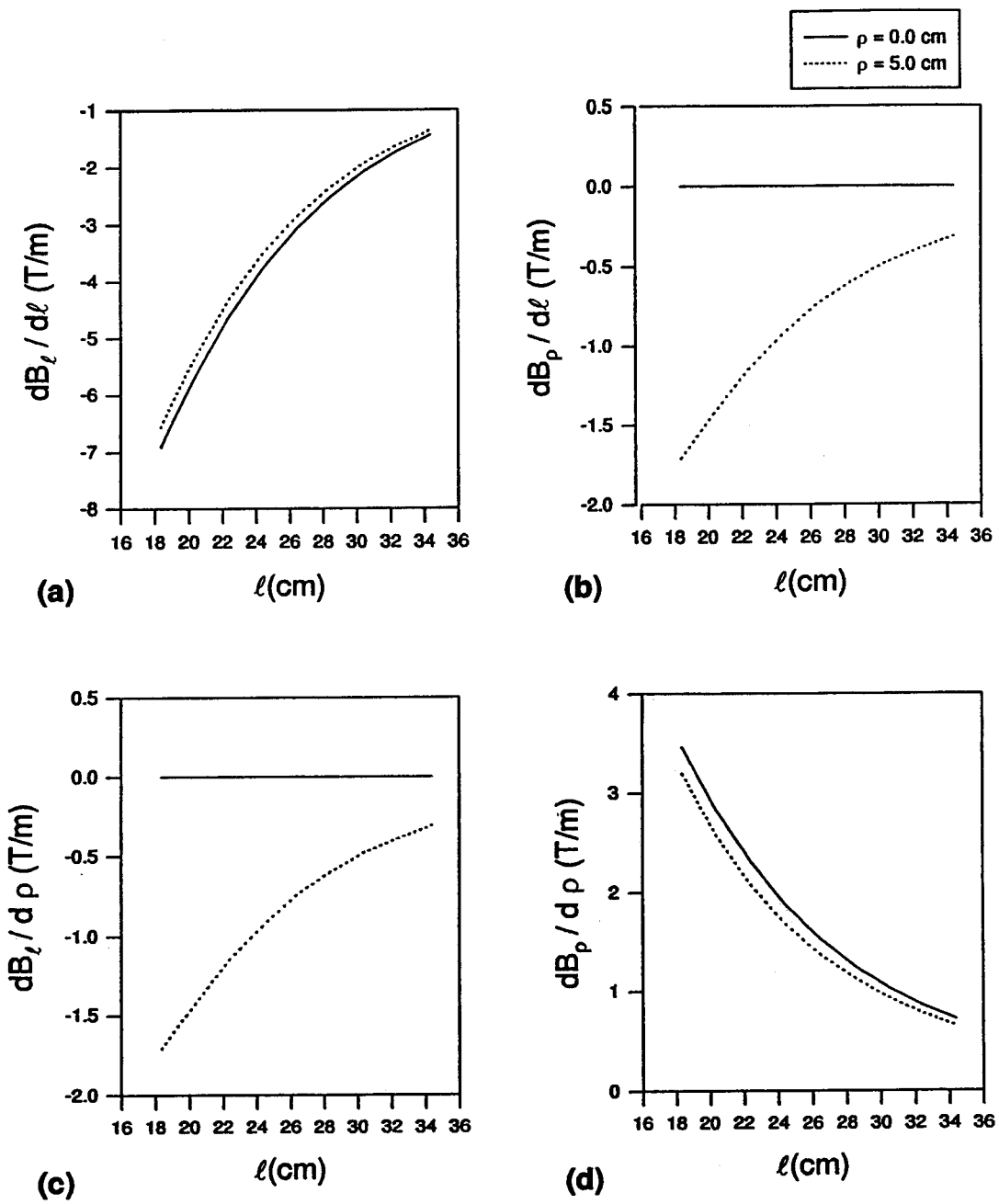
FIG. 3-7. Variation of the directional field derivatives with respect to the axial component of the data plane for the type-1 coil (i.e., the x- and y-coil pairs). Note that graphs (b) and (c) are identical.

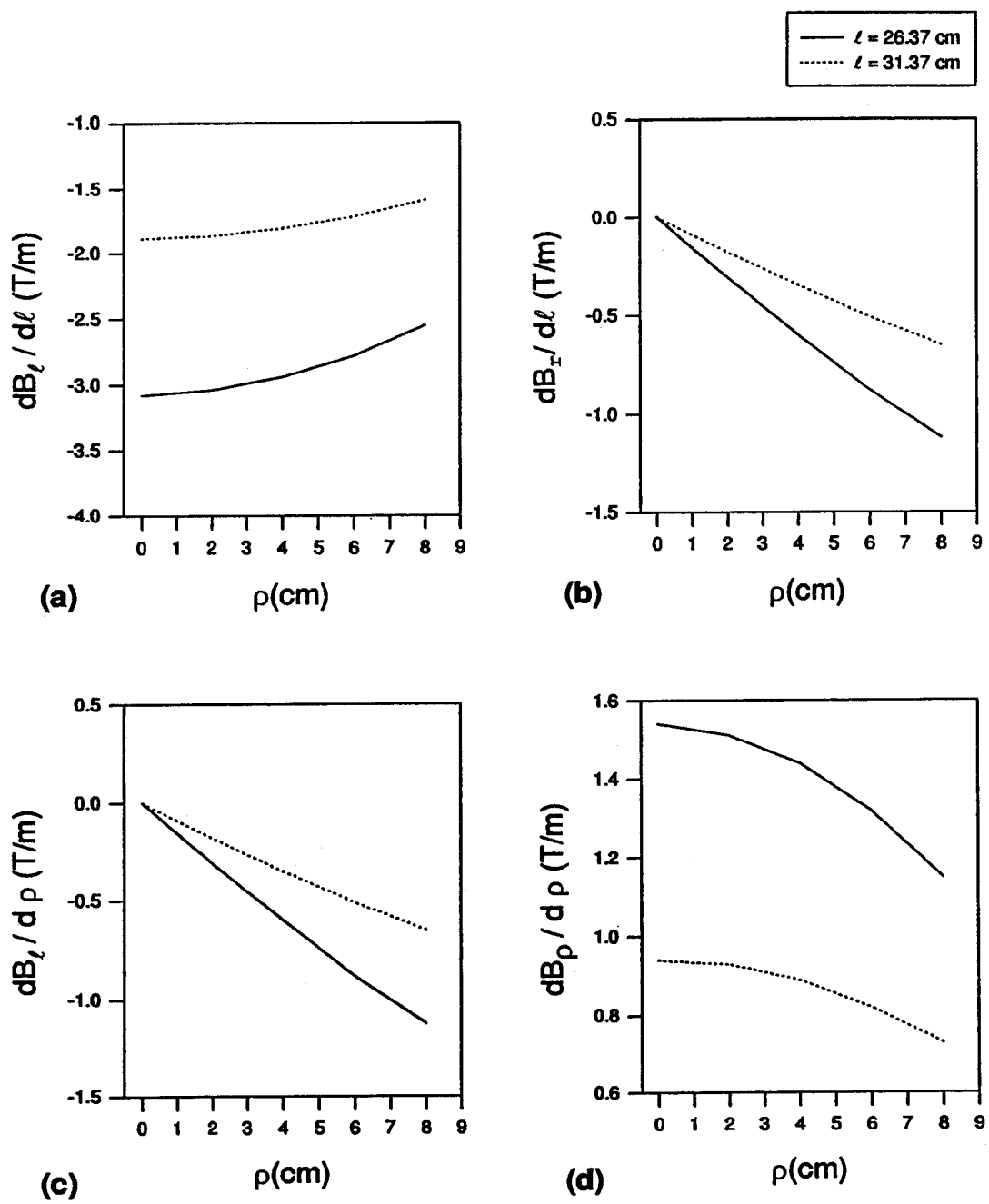
FIG. 3-8. Variation of the directional field derivatives with respect to the radial component of the data plane for the type-1 coil (i.e., the x- and y-coil pairs). Note that graphs (b) and (c) are identical.

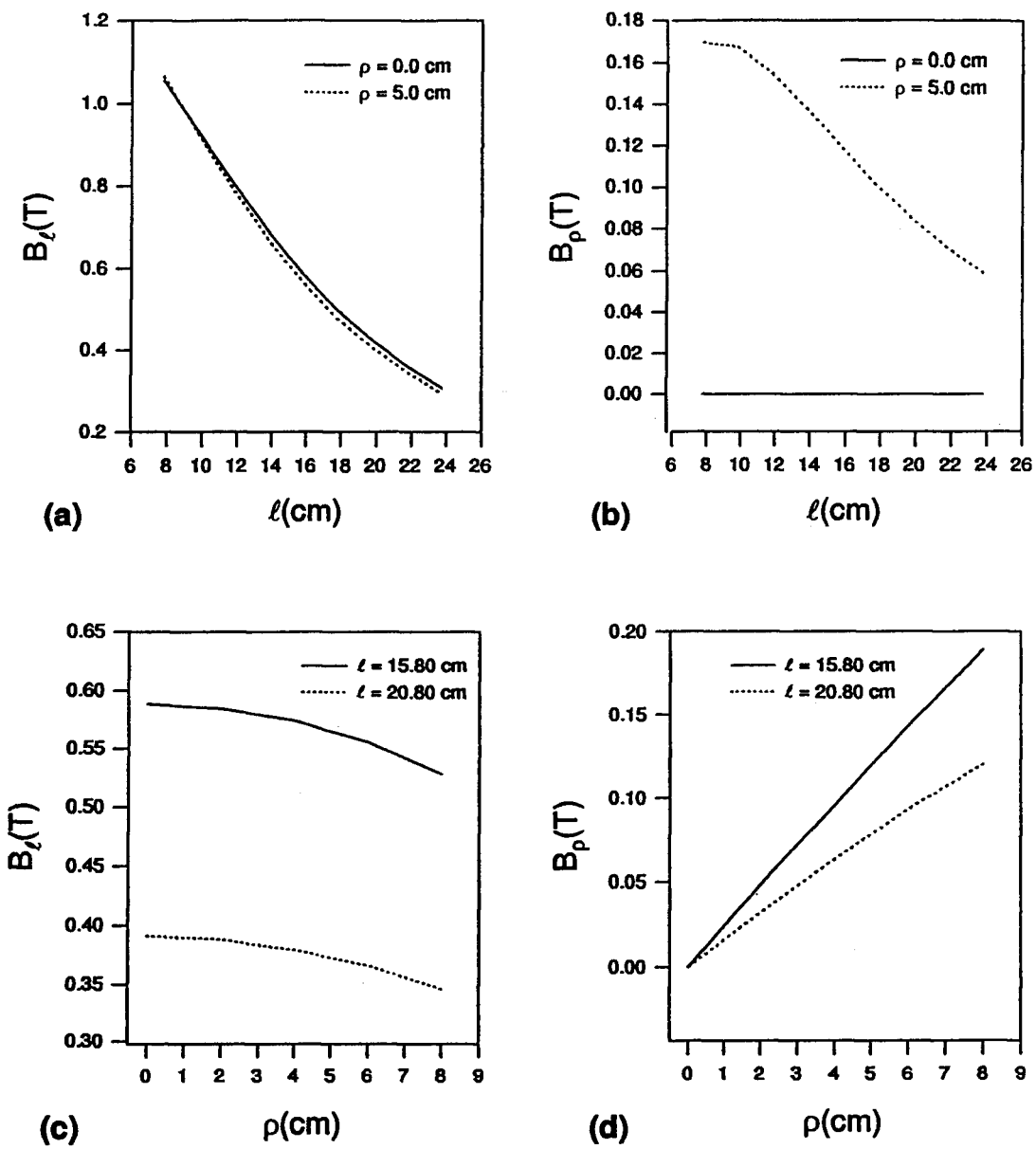
FIG. 3-9. Variation of the magnetic field terms with respect to the axial and radial components of the data plane for the type-2 coil (i.e., the z-coil pair).

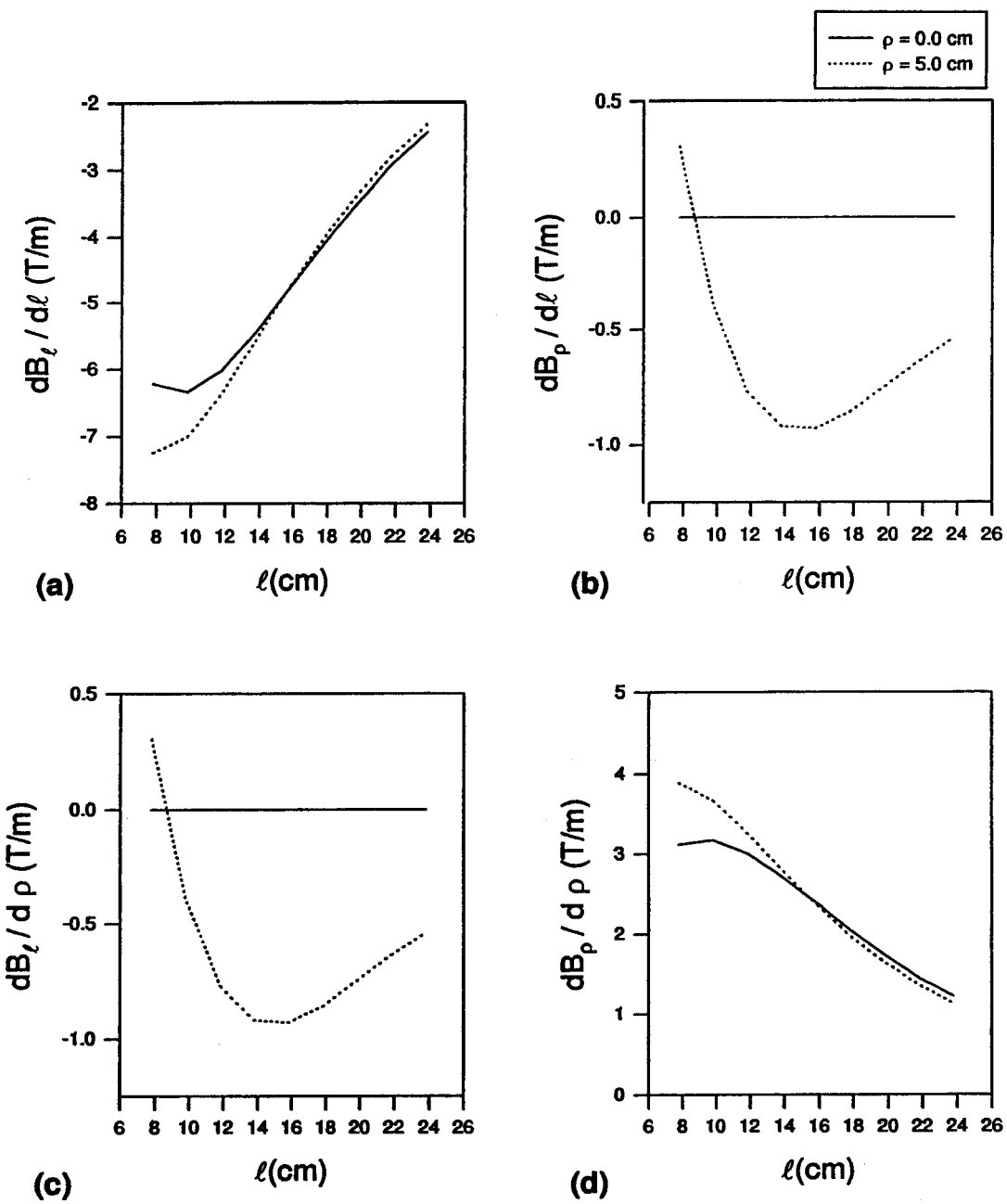
FIG. 3-10. Variation of the directional field derivatives with respect to the axial component of the data plane for the type-2 coil (i.e., the z-coil pair). Note that graphs (b) and (c) are identical.

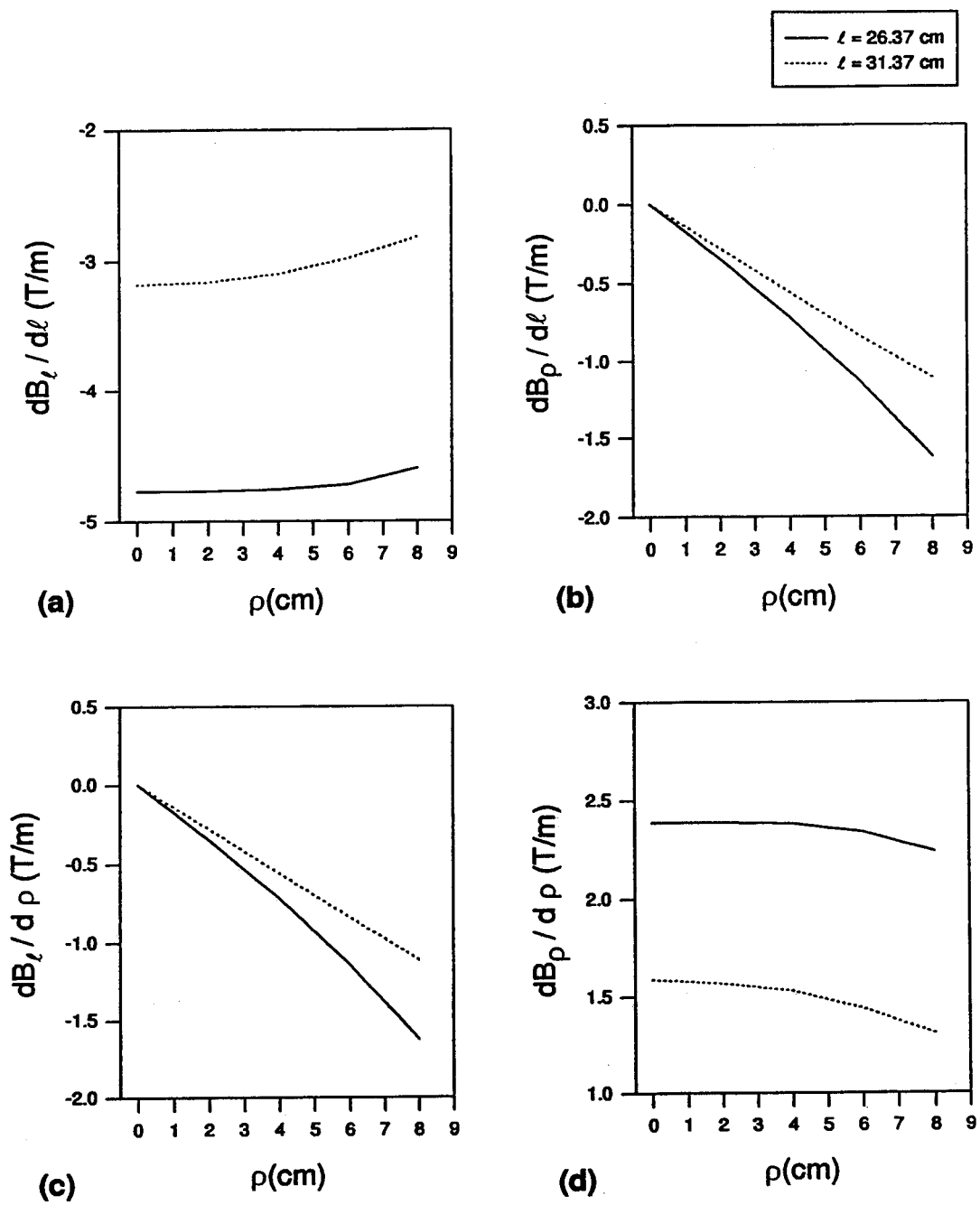
FIG. 3-11. Variation of the directional field derivatives with respect to the radial component of the data plane for the type-2 coil (i.e., the z-coil pair). Note that graphs (b) and (c) are identical.

the axial and radial components of the data plane. All of the depicted fields and field derivatives are calculated within the limit of the spline's data tables.

3-4 Comparison of Predicted to Measured Fields in the MSS

As an initial verification of the computed fields, measurements of the axial field produced by the two coil types, taken with a gaussmeter, were compared to the calculated values [1]. Figures 3-12 and 3-13 depict the calculated axial field and gradient against their measured values for the two coil types encased in the MSS helmet where the field measurements were made with a RFL Model 912 Gaussmeter and an axial Hall probe. A support frame mounted in the interior of the access holes (see Fig. 3-14) was used to locate the probe within the helmet. Construction of the "measured" gradient from the observed magnetic field is done via finite difference, $$\frac{\partial B_\ell(\ell)}{\partial \ell} \approx \frac{B_\ell(\ell+h) - B_\ell(\ell-h)}{2h} \qquad (3\text{-}11)$$

where $B_\ell(\ell)$ is the axial magnetic field measured at the axial position $\ell$ and $h$ is the distance to the neighboring axial positions at which the field is also measured.

Measurement of the magnetic fields produced by the superconducting coils of the MSS proves to be of some difficulty since the coils' exact locations are hidden in the helmet structure. (See Fig. 2-4.) While the precision fabrication techniques used in machining the coils' internal mounting structure provided good parallelism between opposing coils and good orthogonality between the coil axes, the external framing sheet metal (to which the imaging equipment is attached) was not fabricated to as high a degree

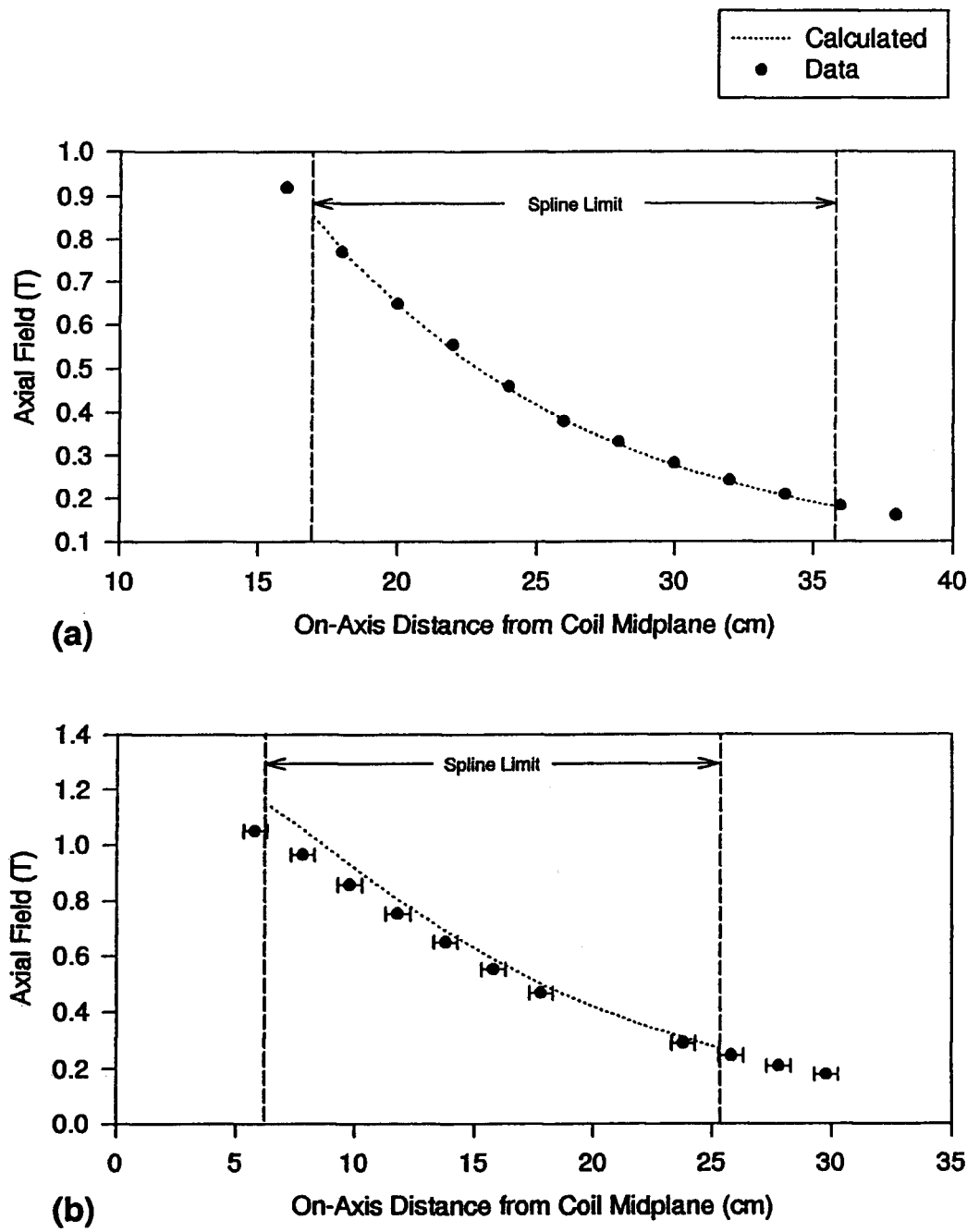

FIG. 3-12. Plots of axial magnetic field versus on-axis distance generated by the (a) type-1 coil at 51.5 A and the (b) type-2 coil at 39.5 A. Calculated values are compared to field data. The calculated values are spline interpolated from a data table whose construction is based upon the specifications of the MSS coils and the numerical integration of Eqs. (3-8a) and (3-10). The spline limit (denoted by the dotted lines) corresponds to the sampling limit of the magnetic field data tables.

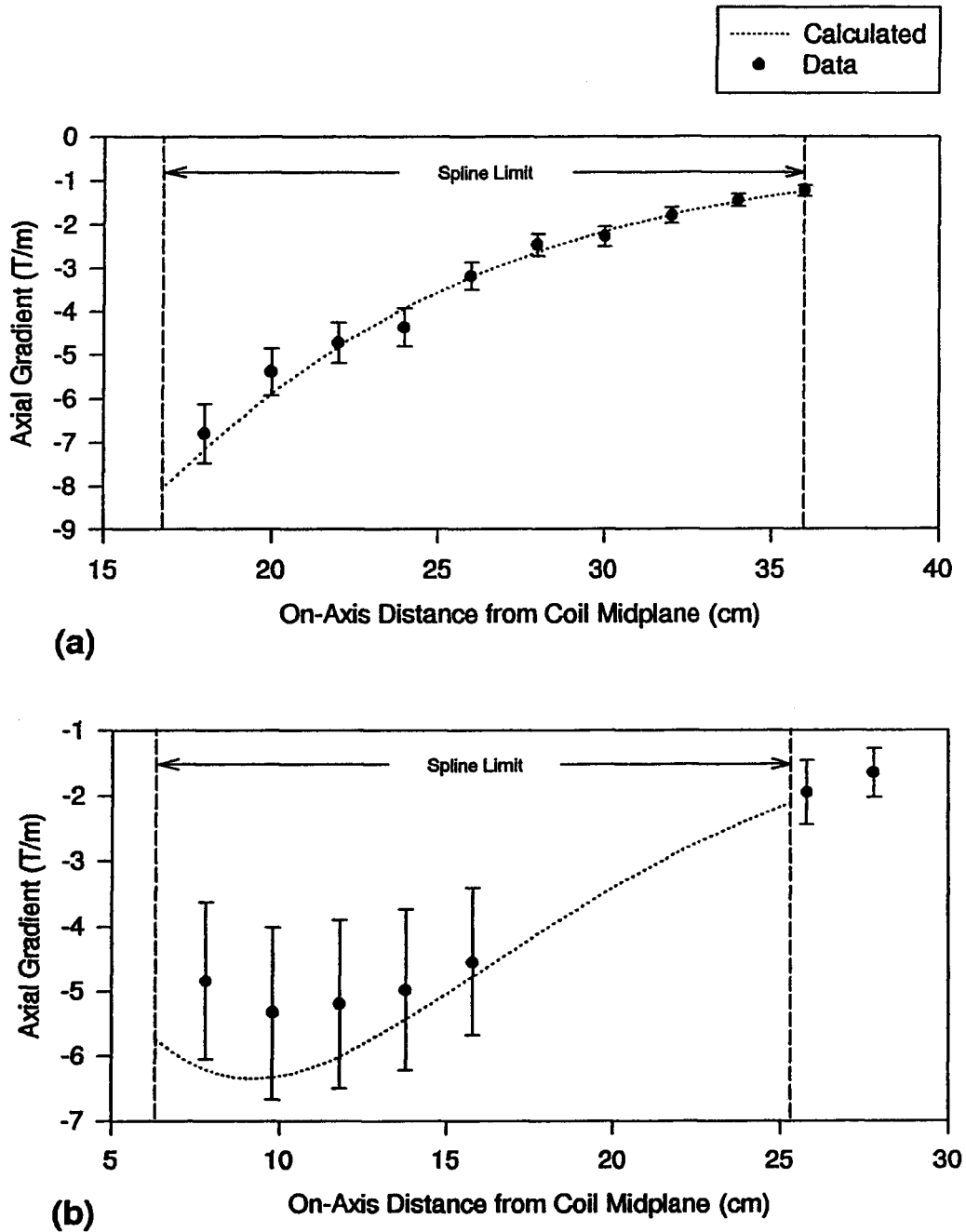

FIG. 3-13. Plots of axial gradient versus on-axis distance generated by the (a) type-1 coil at 51.5 A and the (b) type-2 coil at 39.5 A. Calculated values are compared to field data. The measured values are calculated by finite difference from the magnetic field data depicted in Fig. 3-12, thus approximating the actual derivative. The calculated values are found by taking the first-derivative of the spline-interpolated magnetic field. The spline limit corresponds to the sampling limit of the magnetic field data tables.

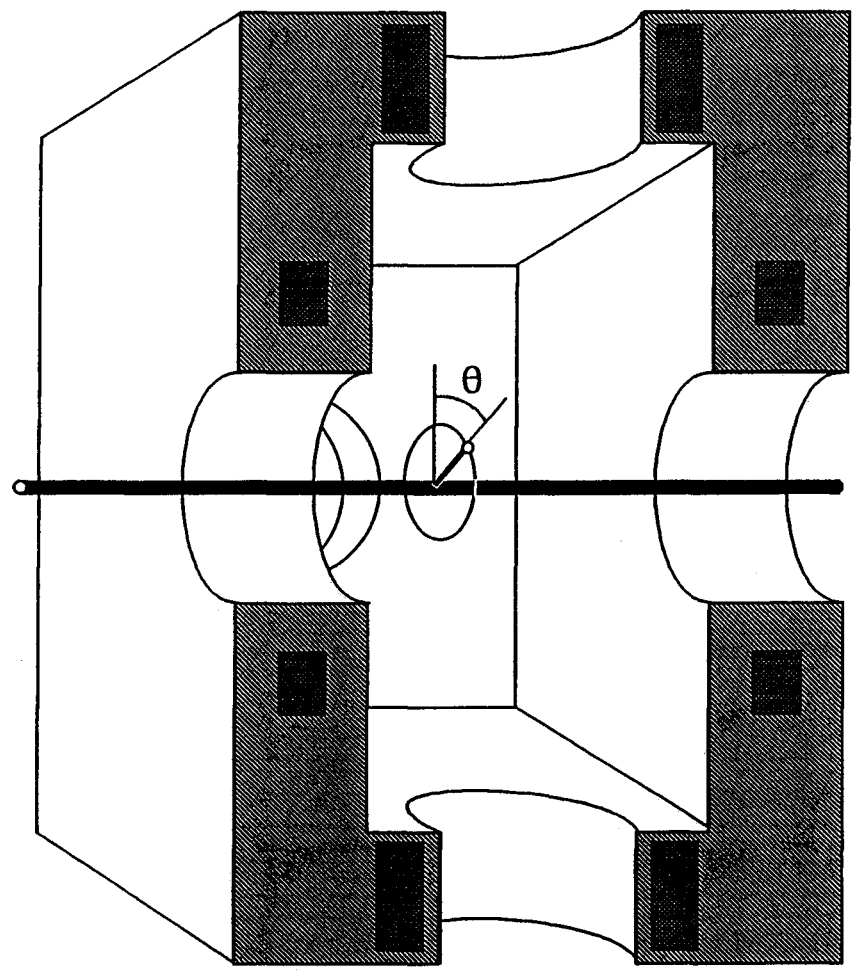

FIG. 3-14. Sketch depicting the cross section of the helmet cryostat with the z-coils located on the horizontal extension and the x- and y- coils located on the vertical and far extensions. The coil cross sections are roughly drawn as the solid blocks located inside the helmet body (hatched). Also displayed is the gaussmeter probe, attached to a long rod fixed along the axis connecting the z-coils. The probe is located 2 cm radially out from the rod and is varied by the angle θ over 360° at 60° increments.

of precision. Thus, error in the location of the coils has been introduced with respect to the surrounding frame. For instance, it was found that precise field measurements for the type-1 coils (located on the side faces) reflected a systematic error associated with the coil's midplane position with respect to the blueprints and the gaussmeter probe, which was estimated at 2 cm. The plots of Figs. 3-12 and 3-13 incorporate this shift for the type-1 coils. Due to difficulties in mounting the support frame in the access holes of the front and rear faces, only crude measurements could be made of the axial magnetic field for the type-2 coils, which explains the increased error for the type-2 coil in both figures.

The gaussmeter probe used in the measurement of the magnetic field could not be located on the axis of the coils since the meter's support rod ran the length of the axis. Measurement of the axial field consisted of the average of six field measurements at (2 cm ± 1 mm) away from the axis, where the measurements were taken at sixty degree increments around the axis. The probe was moved along the axis for subsequent field evaluations. The error associated with the axial displacement of the probe was estimated at 2 mm and constitutes the predominant source of error for the type-1 coil in Fig. 3-13.

As mentioned, the relatively large error in the gradient for the type-2 coil (Fig. 3-13b) is due to the crudeness of the measurements of the magnetic field. The effects on the experiment are tolerable given that gradients remain in fairly close agreement to one another for the region of interest (the dotted lines in Figs. 3-12 and 3-13). For the remaining four coils (one type-2, three type-1), sample points were taken at widely scattered locations for each coil to confirm the adherence of the generated field to the respective reference field. Future studies would profit from a more thorough investigation of the measured fields versus the calculated fields for each coil given that the data taken at the current time represents an incomplete verification of the physical location and magnetic behavior of the six superconducting coils.

APPENDIX "D"

CHAPTER 4

SUMMATION OF FIELD COMPONENTS FOR SINGLE AND MULTIPLE COILS

Having detailed the methods for calculating the magnetic field (as well as the necessary derivatives of the field) of a single coil with a specified geometry, we combine the individual magnetic fields and partial derivatives of the six superconducting coils to form the total magnetic field and total partial derivatives in a general, helmet-centered coordinate system. Additionally, the equalities formed between both the field components and the partial derivatives of the field are detailed, where the equalities result from Maxwell's equations and the quasi-static approximation.

4-1 Position Mapping Between Coordinate Systems

The magnetic implant is referenced in a right-handed, helmet-centered coordinate system whose $e_3$ axis is directed along the midline joining the front- and rear-face coils. The corresponding $e_1$ and $e_2$ components are along the axes connecting the two opposing, side-face coils (see Fig. 3-1). This coordinate system is termed "helmet coordinates" and positions located within the helmet are denoted by x. With the additional knowledge of the currents of the six superconducting coils, the total magnetic field and the total field partial derivatives can be derived.

Having established helmet coordinates as the general reference frame, x must be related to the components $\rho$ and $\ell$ of each coil's data plane (see Fig. 3-5). As was discussed in Chapter 3, no non-zero angular components exist due to the symmetrical nature of the magnetic field produced by a circular coil. Also detailed in Chapter 3 are the methods of calculating the magnetic field and the field's partial derivatives from knowledge of $\rho$ and $\ell$. An additional Cartesian coordinate system is introduced between helmet coordinates and that of the data plane to facilitate the coordinate and vector transformations between the two. As is drawn schematically in Fig. 3-5, this intermediate coordinate system, termed "coil" coordinates, has its origin located at the center of the coil's midplane and one axis, $e_{c,3}$, aligned with the coil's axis. The relationship between coil coordinates and helmet coordinates incorporates the relative locations of the six coils with respect to the helmet assembly (see Table 4-1).

The relationship between helmet coordinates and the coordinates of each coil are as follows: For the X and Y coils, $e_{c,1}$ lies in the $e_1$-$e_2$ plane, $e_{c,2}$ is along the $e_3$ direction, and $e_{c,3}$ is directed towards the origin (where coil coordinates are defined in a right- Table 4-1. Assignment of Coil Index to Superconducting Coils of the MSS*

| Coil Index | Coil Label | $d_1(cm)$ | $d_2(cm)$ | $d_3(cm)$ |
|---|---|---|---|---|
| 1 | X+ | +26.37 | 0.00 | 0.00 |
| 2 | X- | -26.37 | 0.00 | 0.00 |
| 3 | Y+ | 0.00 | +26.37 | 0.00 |
| 4 | Y- | 0.00 | -26.37 | 0.00 |
| 5 | Z+ | 0.00 | 0.00 | +15.80 |
| 6 | Z- | 0.00 | 0.00 | -15.80 |

* Labels and locations of the six superconducting actuators with respect to the coil index. The locations of the coils, denoted by d, are measured from the center of the helmet assembly to the midplane of each coil with respect to helmet coordinates.

Table 4-2 Relationship Between Helmet Coordinates and Coil Coordinates*

| Coil | $x_{C,1}$ | $x_{C,2}$ | $x_{C,3}$ |
|---|---|---|---|
| X+ | $-x_2$ | $x_3$ | $d_1(X+) - x_1$ |
| X- | $x_2$ | $x_3$ | $-d_1(X-) + x_1$ |
| Y+ | $x_1$ | $x_3$ | $d_2(Y+) - x_2$ |
| Y- | $-x_1$ | $x_3$ | $-d_2(Y-) + x_2$ |
| Z+ | $x_2$ | $x_1$ | $d_3(Z+) - x_3$ |
| Z- | $-x_2$ | $x_1$ | $-d_3(Z-) + x_3$ |

* $d_{1,2,3}$ denotes the distance of the coil's midplane from the origin of helmet coordinates as is specified in Table 4-1.

Table 4-3 Relationship Between Coil Coordinates and Data-Plane Coordinates*

| $\ell$ | $\rho$ | $\theta$ |
|---|---|---|
| $x_{C,3}$ | $\sqrt{x_{C,1}^2 + x_{C,2}^2}$ | $\tan^{-1}\left(\dfrac{x_{C,2}}{x_{C,1}}\right)$ |

* $\theta$ corresponds to the polar angle of the data plane relative to the coil coordinates. Its value is necessary for the transformation of the magnetic field and the field partial derivatives (calculated in the data plane) to coil coordinates.

handed coordinate system). For the Z coils, $e_{c,1}$ lies in the $e_2$-$e_3$ plane, $e_{C,2}$ is along the $e_1$ direction, and $e_{C,3}$ is directed towards the origin. These relationships are summarized in Table 4-2. Table 4-3 relates the coordinates of the data plane to coil coordinates where $\theta$ is the angle between the data plane and the $e_{C,1}$-$e_{C,2}$ plane.

4-2  General Formalism

As was introduced in Eq. (3-2), the magnetic field for coil $n$ of the six coils, $B_n$, can be written as the product of the coil's current, $I_n$, and the current-independent magnetic field, $b_n$, such that $$B_n(x, I) = I_n b_n(x) \qquad (4\text{-}1)$$

This is possible due to that fact that the magnetic field of a coil is linear with respect the current of the coil. Thus, $\mathbf{b}_n$ represents the magnetic field per amp (T/A) generated by the coil. It follows that since the magnetic fields from multiple magnetomotive sources add by linear superposition, then the total magnetic field is given by $$\mathbf{B}(\mathbf{x},\mathbf{I}) = \sum_{n=1}^{6} \mathbf{b}_n(\mathbf{x}) I_n = \mathbf{b}(\mathbf{x})\mathbf{I} \qquad (4\text{-}2)$$

where $$\mathbf{b}(\mathbf{x}) = \{\mathbf{b}_1 | \mathbf{b}_2 | \mathbf{b}_3 | \mathbf{b}_4 | \mathbf{b}_5 | \mathbf{b}_6\} \quad ; \quad \mathbf{b}_n = \begin{Bmatrix} b_{n,1} \\ b_{n,2} \\ b_{n,3} \end{Bmatrix} \qquad (4\text{-}3)$$

and $$\mathbf{I}^T = (I_1, I_2, I_3, I_4, I_5, I_6) \qquad (4\text{-}4)$$

In Eq. (4-3), all of the magnetic field terms (which are calculated in T/A) are evaluated in helmet coordinates at the location x. For simplicity of notation, the position dependence of the magnetic field is implied in the work that follows (e.g., $\mathbf{B}(\mathbf{x}) \to \mathbf{B}$). If we define the del operator, $\nabla$, as $$\left. \begin{aligned} \nabla_\lambda &= \frac{\partial}{\partial x_\lambda} \\ \nabla^2_{\lambda,\nu} &= \frac{\partial^2}{\partial x_\lambda \partial x_\nu} \\ &\vdots \end{aligned} \right\} \qquad (4\text{-}5)$$

where the subscripts ($\lambda$, $\nu$, ...) denote the three components of helmet coordinates, then it is a straightforward matter to construct the partial derivatives of the field $$\left.\begin{array}{l}\nabla_\lambda \mathbf{B} = (\nabla_\lambda \mathbf{b})\mathbf{I} \\ \nabla^2_{\lambda,\nu}\mathbf{B} = (\nabla^2_{\lambda,\nu}\mathbf{b})\mathbf{I} \\ \vdots \end{array}\right\} \qquad (4\text{-}6)$$

For the purposes of the present work, only partial derivatives up to second order need to be considered.

4-3  Transformation from the Data Plane to Coil Coordinates

After mapping the point of field evaluation from helmet coordinates to data-plane coordinates for each coil, the fields are calculated in the data plane as was detailed in Chapter 3. The magnetic field and its partials at the point ($\rho$, $\ell$) in the data plane will take the form $$\left.\begin{array}{l} \{b_\ell, b_\rho\} \\ \left\{\dfrac{\partial b_\ell}{\partial \ell}, \dfrac{\partial b_\ell}{\partial \rho}, \dfrac{\partial b_\rho}{\partial \ell}, \dfrac{\partial b_\rho}{\partial \rho}\right\} \\ \left\{\dfrac{\partial^2 b_\ell}{\partial \ell^2}, \dfrac{\partial^2 b_\ell}{\partial \ell \partial \rho}, \dfrac{\partial^2 b_\ell}{\partial \rho^2}, \dfrac{\partial^2 b_\rho}{\partial \ell^2}, \dfrac{\partial^2 b_\rho}{\partial \ell \partial \rho}, \dfrac{\partial^2 b_\rho}{\partial \rho^2}\right\} \\ \vdots \end{array}\right\} \qquad (4\text{-}7)$$

With the assistance of Fig. 3-5, we map the field terms of Eq. (4-7) from data-plane coordinates to coil coordinates for each coil. Temporarily leaving off the coil index, $n$, and defining the magnetic field for a single coil in coil coordinates as $\mathbf{b}_C$, we see that $$\left.\begin{array}{l} b_{C,1} = b_\rho \cos\theta \\ b_{C,2} = b_\rho \sin\theta \\ b_{C,3} = \ell \end{array}\right\} \qquad (4\text{-}8)$$

Tables 4-4 and 4-5 detail the first and second order partials of the magnetic field, respectively.

The partials of Eq. (4-8) with respect to coil coordinates yield the following equalities:

$$\frac{\partial b_{c,1}}{\partial x_{c,2}} = \frac{\partial b_{c,2}}{\partial x_{c,1}} \tag{4-9}$$

$$\frac{\partial^2 b_{c,1}}{\partial x_{c,2}^2} = \frac{\partial^2 b_{c,2}}{\partial x_{c,1} \partial x_{c,2}} \tag{4-10}$$

$$\frac{\partial^2 b_{c,2}}{\partial x_{c,1}^2} = \frac{\partial^2 b_{c,1}}{\partial x_{c,1} \partial x_{c,2}} \tag{4-11}$$

$$\frac{\partial^2 b_{c,1}}{\partial x_{c,3} \partial x_{c,2}} = \frac{\partial^2 b_{c,2}}{\partial x_{c,3} \partial x_{c,1}} \tag{4-12}$$

Two additional equalities are obtained via Maxwell's equations for electromagnetism. The non-existence of magnetic monopoles establishes the condition that $$\nabla \cdot \mathbf{b} = 0 \tag{4-13}$$

which, in the coordinates of the data plane, yields

Table 4-4  First Derivatives of Field Components in Coil Coordinates*

| | | |
|---|---|---|
| $\left(\frac{\partial b_{c,1}}{\partial x_{c,1}}\right) = \cos^2\theta\left(\frac{\partial b_\rho}{\partial \rho}\right) + \sin^2\theta\left(\frac{b_\rho}{\rho}\right)$ | $\left(\frac{\partial b_{c,2}}{\partial x_{c,1}}\right) = \sin\theta\cos\theta\left(\left(\frac{\partial b_\rho}{\partial \rho}\right) - \left(\frac{b_\rho}{\rho}\right)\right)$ | $\left(\frac{\partial b_{c,3}}{\partial x_{c,1}}\right) = \cos\theta\left(\frac{\partial b_\ell}{\partial \rho}\right)$ |
| $\left(\frac{\partial b_{c,1}}{\partial x_{c,2}}\right) = \sin\theta\cos\theta\left(\left(\frac{\partial b_\rho}{\partial \rho}\right) - \left(\frac{b_\rho}{\rho}\right)\right)$ | $\left(\frac{\partial b_{c,2}}{\partial x_{c,2}}\right) = \sin^2\theta\left(\frac{\partial b_\rho}{\partial \rho}\right) + \cos^2\theta\left(\frac{b_\rho}{\rho}\right)$ | $\left(\frac{\partial b_{c,3}}{\partial x_{c,2}}\right) = \sin\theta\left(\frac{\partial b_\ell}{\partial \rho}\right)$ |
| $\left(\frac{\partial b_{c,1}}{\partial x_{c,3}}\right) = \cos\theta\left(\frac{\partial b_\rho}{\partial \ell}\right)$ | $\left(\frac{\partial b_{c,2}}{\partial x_{c,3}}\right) = \sin\theta\left(\frac{\partial b_\rho}{\partial \ell}\right)$ | $\left(\frac{\partial b_{c,3}}{\partial x_{c,3}}\right) = \left(\frac{\partial b_\ell}{\partial \ell}\right)$ |

* The relationship between derivatives in coil coordinates and in data-plane coordinates is detailed in Fig. 3-5.

Table 4-5  Second Derivatives of Field Components in Coil Coordinates*

$$\left(\frac{\partial^2 b_{C,3}}{\partial x_{C,1}^2}\right) = \cos^2\theta\left(\frac{\partial^2 b_\ell}{\partial \rho^2}\right) + \frac{\sin^2\theta}{\rho}\left(\frac{\partial b_\ell}{\partial \rho}\right)$$

$$\left(\frac{\partial^2 b_{C,3}}{\partial x_{C,2}^2}\right) = \sin^2\theta\left(\frac{\partial^2 b_\ell}{\partial \rho^2}\right) + \frac{\cos^2\theta}{\rho}\left(\frac{\partial b_\ell}{\partial \rho}\right)$$

$$\left(\frac{\partial^2 b_{C,3}}{\partial x_{C,3}^2}\right) = \left(\frac{\partial^2 b_\ell}{\partial \ell^2}\right)$$

$$\left(\frac{\partial^2 b_{C,3}}{\partial x_{C,3}\partial x_{C,2}}\right) = \left(\frac{\partial^2 b_{C,3}}{\partial x_{C,2}\partial x_{C,3}}\right) = \sin\theta\left(\frac{\partial^2 b_\ell}{\partial \rho \partial \ell}\right)$$

$$\left(\frac{\partial^2 b_{C,3}}{\partial x_{C,1}\partial x_{C,2}}\right) = \left(\frac{\partial^2 b_{C,3}}{\partial x_{C,2}\partial x_{C,1}}\right) = \sin\theta\cos\theta\left(\left(\frac{\partial^2 b_\ell}{\partial \rho^2}\right) - \frac{1}{\rho}\left(\frac{\partial b_\ell}{\partial \rho}\right)\right)$$

$$\left(\frac{\partial^2 b_{C,3}}{\partial x_{C,3}\partial x_{C,1}}\right) = \left(\frac{\partial^2 b_{C,3}}{\partial x_{C,1}\partial x_{C,3}}\right) = \cos\theta\left(\frac{\partial^2 b_\ell}{\partial \rho \partial \ell}\right)$$

$$\left(\frac{\partial^2 b_{C,1}}{\partial x_{C,1}^2}\right) = \cos^3\theta\left(\frac{\partial^2 b_\rho}{\partial \rho^2}\right) + \frac{3\sin^2\theta\cos\theta}{\rho}\left(\left(\frac{\partial b_\rho}{\partial \rho}\right) - \frac{b_\rho}{\rho}\right)$$

$$\left(\frac{\partial^2 b_{C,1}}{\partial x_{C,2}^2}\right) = \sin^2\theta\cos\theta\left(\left(\frac{\partial^2 b_\rho}{\partial \rho^2}\right) - \frac{2}{\rho}\left(\frac{\partial b_\rho}{\partial \rho}\right) + \frac{2b_\rho}{\rho^2}\right) + \frac{\cos^3\theta}{\rho}\left(\left(\frac{\partial b_\rho}{\partial \rho}\right) - \frac{b_\rho}{\rho}\right)$$

$$\left(\frac{\partial^2 b_{C,1}}{\partial x_{C,3}^2}\right) = \cos\theta\left(\frac{\partial^2 b_\rho}{\partial \ell^2}\right)$$

$$\left(\frac{\partial^2 b_{C,1}}{\partial x_{C,3}\partial x_{C,1}}\right) = \left(\frac{\partial^2 b_{C,1}}{\partial x_{C,1}\partial x_{C,3}}\right) = \cos^2\theta\left(\frac{\partial^2 b_\rho}{\partial \rho \partial \ell}\right) + \frac{\sin^2\theta}{\rho}\left(\frac{\partial b_\rho}{\partial \ell}\right)$$

$$\left(\frac{\partial^2 b_{C,1}}{\partial x_{C,3}\partial x_{C,2}}\right) = \left(\frac{\partial^2 b_{C,1}}{\partial x_{C,2}\partial x_{C,3}}\right) = \sin\theta\cos\theta\left(\left(\frac{\partial^2 b_\rho}{\partial \rho \partial \ell}\right) - \frac{1}{\rho}\left(\frac{\partial b_\rho}{\partial \ell}\right)\right)$$

$$\left(\frac{\partial^2 b_{C,1}}{\partial x_{C,1}\partial x_{C,2}}\right) = \left(\frac{\partial^2 b_{C,1}}{\partial x_{C,2}\partial x_{C,1}}\right) = \sin\theta\cos^2\theta\left(\left(\frac{\partial^2 b_\rho}{\partial \rho^2}\right) - \frac{2}{\rho}\left(\frac{\partial b_\rho}{\partial \rho}\right) + \frac{2b_\rho}{\rho^2}\right) + \frac{\sin^3\theta}{\rho}\left(\left(\frac{\partial b_\rho}{\partial \rho}\right) - \frac{b_\rho}{\rho}\right)$$

$$\left(\frac{\partial^2 b_{C,2}}{\partial x_{C,1}^2}\right) = \sin\theta\cos^2\theta\left(\left(\frac{\partial^2 b_\rho}{\partial \rho^2}\right) - \frac{2}{\rho}\left(\frac{\partial b_\rho}{\partial \rho}\right) + \frac{2b_\rho}{\rho^2}\right) + \frac{\sin^3\theta}{\rho}\left(\left(\frac{\partial b_\rho}{\partial \rho}\right) - \frac{b_\rho}{\rho}\right)$$

$$\left(\frac{\partial^2 b_{C,2}}{\partial x_{C,2}^2}\right) = \sin^3\theta\left(\frac{\partial^2 b_\rho}{\partial \rho^2}\right) + \frac{3\sin\theta\cos^2\theta}{\rho}\left(\left(\frac{\partial b_\rho}{\partial \rho}\right) - \frac{b_\rho}{\rho}\right)$$

$$\left(\frac{\partial^2 b_{C,2}}{\partial x_{C,3}^2}\right) = \sin\theta\left(\frac{\partial^2 b_\rho}{\partial \ell^2}\right)$$

$$\left(\frac{\partial^2 b_{C,2}}{\partial x_{C,3}\partial x_{C,1}}\right) = \left(\frac{\partial^2 b_{C,2}}{\partial x_{C,1}\partial x_{C,3}}\right) = \sin\theta\cos\theta\left(\left(\frac{\partial^2 b_\rho}{\partial \rho \partial \ell}\right) - \frac{1}{\rho}\left(\frac{\partial b_\rho}{\partial \ell}\right)\right)$$

$$\left(\frac{\partial^2 b_{C,2}}{\partial x_{C,3}\partial x_{C,2}}\right) = \left(\frac{\partial^2 b_{C,2}}{\partial x_{C,2}\partial x_{C,3}}\right) = \sin^2\theta\left(\frac{\partial^2 b_\rho}{\partial \rho \partial \ell}\right) + \frac{\cos^2\theta}{\rho}\left(\frac{\partial b_\rho}{\partial \ell}\right)$$

$$\left(\frac{\partial^2 b_{C,2}}{\partial x_{C,1}\partial x_{C,2}}\right) = \left(\frac{\partial^2 b_{C,2}}{\partial x_{C,2}\partial x_{C,1}}\right) = \sin^2\theta\cos\theta\left(\left(\frac{\partial^2 b_\rho}{\partial \rho^2}\right) - \frac{2}{\rho}\left(\frac{\partial b_\rho}{\partial \rho}\right) + \frac{2b_\rho}{\rho^2}\right) + \frac{\cos^3\theta}{\rho}\left(\left(\frac{\partial b_\rho}{\partial \rho}\right) - \frac{b_\rho}{\rho}\right)$$

* The relationship between second derivatives in coil coordinates and in data-plane coordinates is detailed in Fig. 3-5.

$$\frac{\partial b_\ell}{\partial \ell} + \frac{\partial b_\rho}{\partial \rho} + \frac{b_\rho}{\rho} = 0 \qquad (4\text{-}14)$$

In coil coordinates, Eq. (4-13) is rewritten as $$\frac{\partial b_{c,1}}{\partial x_{c,1}} + \frac{\partial b_{c,2}}{\partial x_{c,2}} + \frac{\partial b_{c,3}}{\partial x_{c,3}} = 0 \qquad (4\text{-}15)$$

Since the fields in the MSS are slowly changing, we can make the static/quasi-static approximation which yields the condition that $$\nabla \times \mathbf{b} = 0 \qquad (4\text{-}16)$$

Rewriting Eq. (4-16) in terms of data-plane coordinates, we form the following relationships:

$$\frac{\partial b_\ell}{\partial \rho} = \frac{\partial b_\rho}{\partial \ell} \qquad (4\text{-}17)$$

$$\frac{\partial^2 b_\ell}{\partial \rho^2} = \frac{\partial^2 b_\rho}{\partial \rho \partial \ell} \qquad (4\text{-}18)$$

$$\frac{\partial^2 b_\rho}{\partial \ell^2} = \frac{\partial^2 b_\ell}{\partial \rho \partial \ell} \qquad (4\text{-}19)$$

In terms of coil coordinates, we find from Eq. (4-16) that $$\frac{\partial b_{c,3}}{\partial x_{c,1}} = \frac{\partial b_{c,1}}{\partial x_{c,3}} \qquad (4\text{-}20)$$

$$\frac{\partial b_{c,3}}{\partial x_{c,2}} = \frac{\partial b_{c,2}}{\partial x_{c,3}} \qquad (4\text{-}21)$$

$$\frac{\partial^2 b_{c,3}}{\partial x_{c,1}^2} = \frac{\partial^2 b_{c,1}}{\partial x_{c,3} \partial x_{c,1}} \qquad (4\text{-}22)$$

$$\frac{\partial^2 b_{c,3}}{\partial x_{c,2}^2} = \frac{\partial^2 b_{c,2}}{\partial x_{c,3} \partial x_{c,2}} \qquad (4\text{-}23)$$

$$\frac{\partial^2 b_{c,1}}{\partial x_{c,3}^2} = \frac{\partial^2 b_{c,3}}{\partial x_{c,3} \partial x_{c,1}} \qquad (4\text{-}24)$$

$$\frac{\partial^2 b_{c,2}}{\partial x_{c,3}^2} = \frac{\partial^2 b_{c,3}}{\partial x_{c,3} \partial x_{c,2}} \qquad (4\text{-}25)$$

$$\frac{\partial^2 b_{c,2}}{\partial x_{c,1} \partial x_{c,3}} = \frac{\partial^2 b_{c,1}}{\partial x_{c,2} \partial x_{c,3}} = \frac{\partial^2 b_{c,3}}{\partial x_{c,1} \partial x_{c,2}} \qquad (4\text{-}26)$$

4-4 Transformation from Coil Coordinates to Helmet Coordinates

The magnetic field and the field's partial derivatives for each coil are mapped into helmet coordinates as is summarized in Tables 4-2 and 4-6. To calculate the total magnetic field and partial derivatives, additional knowledge of the coil currents, I, is required. However, since the field terms Table 4-6 Field Transformation of Coil Coordinates to Helmet Coordinates*

| Coil | $b_1$ | $b_2$ | $b_3$ |
|---|---|---|---|
| X+ | $-b_{c,3}$ | $-b_{c,1}$ | $b_{c,2}$ |
| X- | $b_{c,3}$ | $b_{c,1}$ | $b_{c,2}$ |
| Y+ | $b_{c,1}$ | $-b_{c,3}$ | $b_{c,2}$ |
| Y- | $-b_{c,1}$ | $b_{c,3}$ | $b_{c,2}$ |
| Z+ | $b_{c,2}$ | $b_{c,1}$ | $-b_{c,3}$ |
| Z- | $b_{c,2}$ | $-b_{c,1}$ | $b_{c,3}$ |

* The partials are related to helmet coordinates from coil coordinates according to the coordinate transformations of Table 4-2.

$$\left.\begin{array}{c} b(x) \\ \nabla_\lambda b(x) \\ \nabla^2_{\lambda,v} b(x) \\ \vdots \end{array}\right\} \qquad (4\text{-}27)$$

require only one evaluation for each unique position x, different current sets can be combined according to Eq. (4-2) to investigate the nature of the magnetic field without the need of recalculating the components of Eq. (4-7). The flowchart in Fig. 4-1 details the complete process of generating the total magnetic field and the total field partial derivatives from knowledge of the position, x, in helmet coordinates and the coil currents.

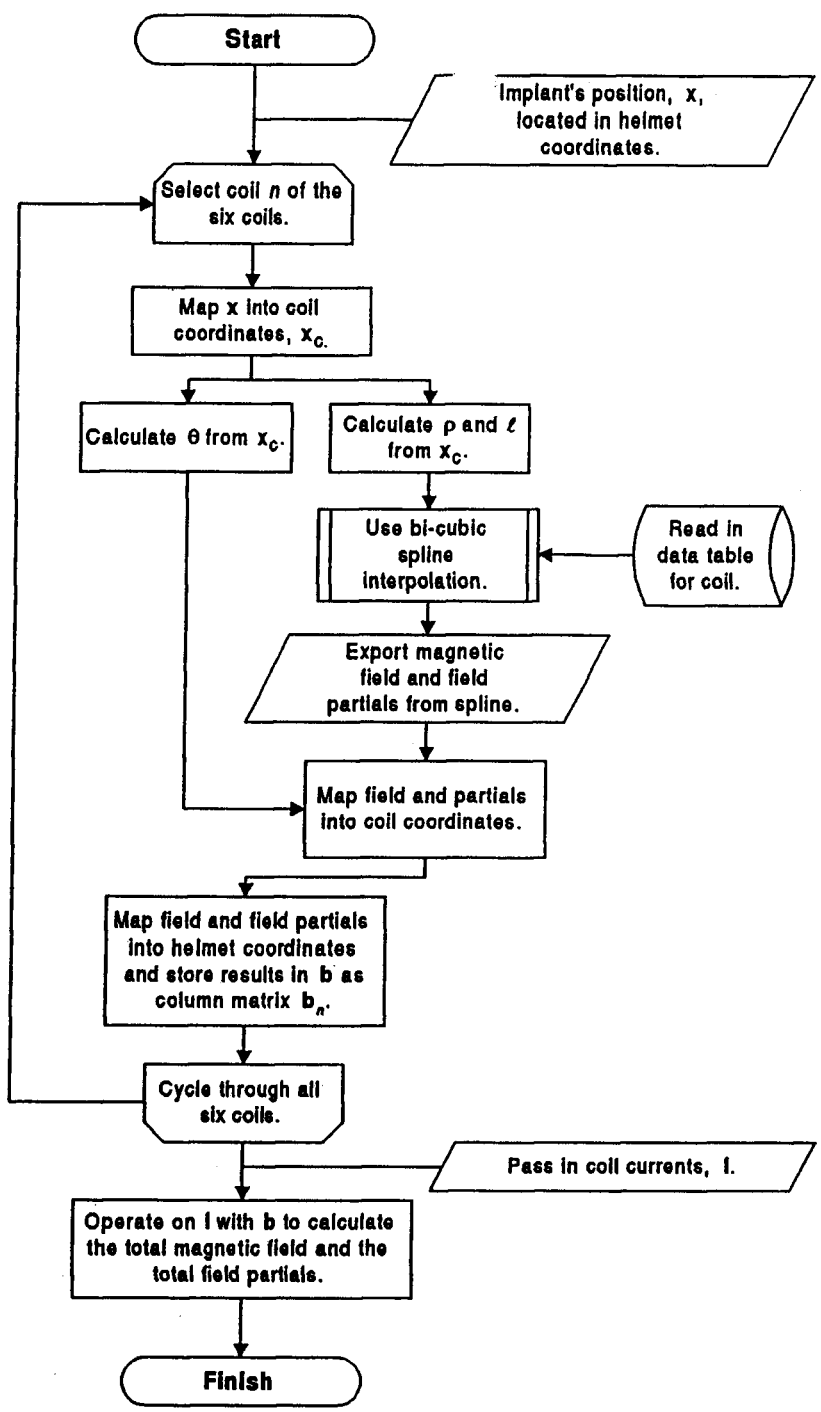

FIG. 4-1. Flowchart for the calculation of the total magnetic field and field partials from the position, x, in helmet coordinates and a set of currents, I. Subsequent current sets may be inserted into the algorithm to calculate the total magnetic field and total field partials without the need of recalculating the field or the field's derivatives, providing that x remains unchanged.